(12) United States Patent
Lin et al.

(10) Patent No.: US 12,042,788 B2
(45) Date of Patent: Jul. 23, 2024

(54) STRONGLY LEWIS ACIDIC METAL-ORGANIC FRAMEWORKS FOR CONTINUOUS FLOW CATALYSIS

(71) Applicant: The University of Chicago, Chicago, IL (US)

(72) Inventors: Wenbin Lin, Chicago, IL (US); Xuanyu Feng, Chicago, IL (US); Pengfei Ji, Chicago, IL (US)

(73) Assignee: The University of Chicago, Chicago, IL (US)

( * ) Notice: Subject to any disclaimer, the term of this patent is extended or adjusted under 35 U.S.C. 154(b) by 728 days.

(21) Appl. No.: 16/999,818

(22) Filed: Aug. 21, 2020

(65) Prior Publication Data

US 2021/0053042 A1 Feb. 25, 2021

Related U.S. Application Data

(60) Provisional application No. 62/889,871, filed on Aug. 21, 2019.

(51) Int. Cl.
| | |
|---|---|
| B01J 31/16 | (2006.01) |
| B01J 21/08 | (2006.01) |
| C07D 307/06 | (2006.01) |
| C07D 307/20 | (2006.01) |
| C07D 307/79 | (2006.01) |
| C07D 309/30 | (2006.01) |

(52) U.S. Cl.
CPC ........... *B01J 31/1691* (2013.01); *B01J 21/08* (2013.01); *C07D 307/06* (2013.01); *C07D 307/20* (2013.01); *C07D 307/79* (2013.01); *C07D 309/30* (2013.01); *B01J 2231/005* (2013.01); *B01J 2231/325* (2013.01); *B01J 2231/326* (2013.01); *B01J 2231/342* (2013.01); *B01J 2231/485* (2013.01); *B01J 2531/48* (2013.01); *B01J 2531/824* (2013.01)

(58) Field of Classification Search
None
See application file for complete search history.

(56) References Cited

PUBLICATIONS

Ji et al. "Strongly Lewis Acidic Metal-Organic Frameworks for Continuous Flow Catalysis" Journal of the American Chemical Society, 2019, vol. 141, No. 37, pp. 14878-14888.*
Ager et al., "1,2-Amino Alcohols and Their Heterocyclic Derivatives as Chiral Auxiliaries in Asymmetric Synthesis." Chem. Rev., vol. 96(2), pp. 835-876 (1996).
Alonso et al., "Bimetallic catalysts for upgrading of biomass to fuels and chemicals." Chem. Soc. Rev., vol. 41(24), pp. 8075-8098 (2012).
Barluenga et al., "[W(CO)5]-Catalyzed endo- or exo-Cycloisomerization Reactions of 1,1-Disubstituted 4-Pentyn-1-ols: Experimental and Theoretical Studies." Chem. Eur. J., vol. 11(19), pp. 5735-5741 (2005).
Blackwell et al., "A Chromatographic Study of the Lewis Acid-Base Chemistry of Zirconia Surfaces." J. Liq. Chromatogr., vol. 14(15), pp. 2875-2889 (1991).
Blunt et al., "Marine natural products." Nat. Prod. Rep., vol. 35(1), pp. 8-53 (2018).
Boiteau et al., "A New, Ring Closing Metathesis-Based Synthesis of (−)-Fumagillol." Org. Lett., vol. 3(17), pp. 2737-2740 (2001).
Chakraborti et al., "ZrCl4 as a new and efficient catalyst for the opening of epoxide rings by amines." Tetrahedron Lett., vol. 44(45), pp. 8315-8319 (2003).
Chen et al., "Boosting Chemical Stability, Catalytic Activity, and Enantioselectivity of Metal-Organic Frameworks for Batch and Flow Reactions." J. Am. Chem. Soc., vol. 139(38), pp. 13476-13482 (2017).
Comito et al., "Single-Site Heterogeneous Catalysts for Olefin Polymerization Enabled by Cation Exchange in a Metal-Organic Framework." J. Am. Chem. Soc., vol. 138(32), pp. 10232-10237 (2016).
Corma et al., "Lewis Acids as Catalysts in Oxidation Reactions: From Homogeneous to Heterogeneous Systems." Chem. Rev., vol. 102(10), pp. 3837-3892 (2002).
Corma et al., "Lewis Acids: From Conventional Homogeneous to Green Homogeneous and Heterogeneous Catalysis." Chem. Rev., vol. 103(11), pp. 4307-4366 (2003).
Corma et al., "Sn-Beta zeolite as diastereoselective water-resistant heterogeneous Lewis-acid catalyst for carbon-carbon bond formation in the intramolecular carbonyl-ene reaction." Chem. Commun., pp. 550-551 (2004).
Das et al., "Functional mixed metal-organic frameworks with metalloligands." Angew. Chem., Int. Ed., vol. 50, pp. 10510-10520 (2011).
Drake et al., "Site Isolation in Metal-Organic Frameworks Enables Novel Transition Metal Catalysis." Acc. Chem. Res., vol. 51(9), pp. 2129-2138 (2018).
Dzudza et al., "Lanthanide Triflate-Catalyzed Arene Acylation Relation to Classical Friedel-Crafts Acylation." J. Org. Chem., vol. 73(11), pp. 4004-4016 (2008).
Evans et al., "Crystal Engineering of NLO Materials Based on Metal-Organic Coordination Networks." Acc. Chem. Res., vol. 35, pp. 511-522 (2002).
Feng, et al., "Metal-Organic Framework Stabilizes a Low-Coordinate Iridium Complex for Catalytic Methane Borylation." J. Am. Chem. Soc. (2019).

(Continued)

*Primary Examiner* — Joseph R Kosack
(74) *Attorney, Agent, or Firm* — Jenkins, Taylor & Hunt, P.A.

(57) ABSTRACT

Lewis acidic metal-organic framework (MOF) materials comprising triflate-coordinated metal nodes are described. The materials can be used as heterogenous catalysts in a wide range of organic group transformations, including Diels-Alder reactions, epoxide-ring opening reactions, Friedel-Crafts acylation reactions and alkene hydroalkoxylation reactions. The MOFs can also be prepared with metallated organic bridging ligands to provide heterogenous catalysts for tandem reactions and/or prepared as composites with support particles for use in columns of continuous flow reactor systems. Methods of preparing and using the MOF materials and their composites are also described.

10 Claims, 17 Drawing Sheets

(56) References Cited

PUBLICATIONS

Frisch et al., Gaussian 09, revision E. 01. Pittsburgh PA: Gaussian. Inc: 2009.

Fukuzumi et al., "ESR Spectra of Superoxide Anion-Scandium Complexes Detectable in Fluid Solution." J. Am. Chem. Soc., vol. 121(7), pp. 1605-1606 (1999).

Furukawa et al., "The Chemistry and Applications of Metal-Organic Frameworks." Science, vol. 341, pp. 974-986 (2013).

Furukawa et al., "Water Adsorption in Porous Metal-Organic Frameworks and Related Materials." J. Am. Chem. Soc., vol. 136(11), pp. 4369-4381 (2014).

Gao et al., "Enzyme-Catalyzed Intramolecular Enantioselective Hydroalkoxylation." J. Am. Chem. Soc., vol. 139(10), pp. 3639-3642 (2017).

Guillerm et al., "Postsynthetic Selective Ligand Cleavage by Solid-Gas Phase Ozonolysis Fuses Micropores into Mesopores in Metal-Organic Frameworks." J. Am. Chem. Soc., vol. 140(44), pp. 15022-15030 (2018).

He et al., "A Versatile Metalloporphyrinic Framework Platform for Highly Efficient Bioinspired, Photo- and Asymmetric Catalysis." Angew. Chem. In. Ed. vol. 58(1), pp. 168-172 (2019).

Herrmann et al., "Zirconium and hafnium (1-pyridinio)imido complexes: functionalized terminal hydrazinediido analogues." Dalton Trans., No. 44, pp. 6231-6241 (2008).

Horike et al., "Size-Selective Lewis Acid Catalysis in a Microporous Metal-Organic Framework with Exposed Mn2+ Coordination Sites." J. Am. Chem. Soc., vol. 130(18), pp. 5854-5855 (2008).

Houk et al., "Lewis acid catalysis of Diels-Alder reactions." J. Am. Chem. Soc., vol. 95(12), pp. 4094-4096 (1973).

Jacobsen et al., "Asymmetric Catalysis of Epoxide Ring-Opening Reactions." Acc. Chem. Res., vol. 33(6), pp. 421-431 (2000).

Ji et al., "Transformation of Metal-Organic Framework Secondary Building Units into Hexanuclear Zr-Alkyl Catalysts for Ethylene Polymerization." J. Am. Chem. Soc., vol. 139(33), pp. 11325-11328 (2017).

Ji et al., "Trivalent Zirconium and Hafnium Metal-Organic Frameworks for Catalytic 1,4-Dearomative Additions of Pyridines and Quinolines." J. Am. Chem. Soc., vol. 139(44), pp. 15600-15603 (2017).

Ji et al., "Tuning Lewis Acidity of Metal-Organic Frameworks via Perfluorination of Bridging Ligands: Spectroscopic, Theoretical and Catalytic Studies." J. Am. Chem. Soc., vol. 140(33), pp. 10553-10561 (2018).

Kamal et al., "Copper(II) tetrafluoroborate-catalyzed ring-opening of epoxides by amines." Tetrahedron Lett., vol. 46(15), pp. 2675-2677 (2005).

Kesanli et al., "Chiral porous coordination networks: rational design and applications in enantioselective processes." Coord. Chem. Rev., vol. 246, pp. 305-326 (2003).

Kobayashi et al., "A Microencapsulated Lewis Acid. A New Type of Polymer-Supported Lewis Acid Catalyst of Wide Utility in Organic Synthesis." J. Am. Chem. Soc., vol. 120(12), pp. 2985-2986 (1998).

Kreno et al., "Metal Organic Framework Materials as Chemical Sensors." Chem. Rev., vol. 112, pp. 1105-1125 (2012).

Kristian et al., "Mechanism of the Reaction of Alkynes with a 'Constrained Geometry' Zirconaaziridine. PMe3 Dissociates More Rapidly from the Constrained Geometry Complex than from its Cp2 Analogue." Organometallics, vol. 28(2), pp. 493-498 (2009).

Lan et al., "A luminescent microporous metal-organic framework for the fast and reversible detection of high explosives." Angew Chem., Int. Ed., vol. 48, pp. 2334-2338 (2008).

Li et al., "Metal-organic frameworks for separations." Chem. Rev., vol. 112, pp. 869-932 (2012).

Li et al., "Rapid Ether and Alcohol C—O Bond Hydrogenolysis Catalyzed by Tandem High-Valent Metal Triflate + Supported Pd Catalysts." J. Am. Chem Soc., vol. 136(1), pp. 104-107 (2013).

Lohr et al., "Thermodynamically Leveraged Tandem Catalysis for Ester RC(O)O-R' Bond Hydrogenolysis. Scope and Mechanism." ACS Catalysis, vol. 5(6), pp. 3675-3679 (2015).

Lunsford et al., "An NMR study of acid sites on sulfated-zirconia catalysts using trimethylphosphine as a probe." Catal. Lett., vol. 27(3), pp. 305-314 (1994).

Miller et al., "Copper-Catalyzed Intramolecular Alkene Carboetherification: Synthesis of Fused-Ring and Bridged-Ring Tetrahydrofurans." J. Am. Chem. Soc., vol. 134(29), pp. 12149-12156 (2012).

Miller et al., "Kinetics and Mechanisms of Methyl Vinyl Ketone Hydroalkoxylation Catalyzed by Palladium(II) Complexes." Organometallics, vol. 20(21), pp. 4403-4412 (2001).

Momeni et al., "Structural Characterization of Pristine and Defective [Zr12(µ3—O)8(µ2—OH)8(µ2—OH)6]18+ Double-Node Metal-Organic Framework and Predicted Applications for Single-Site Catalytic Hydrolysis of Sarin." Chem. Mater., vol. 30(13), pp. 4432-4439 (2018).

Mondloch et al., "Destruction of chemical warfare agents using metal-organic frameworks." Nat. Mater., vol. 14, pp. 512 (2015).

Moon et al., "Instantaneous Hydrolysis of Nerve-Agent Simulants with a Six-Connected Zirconium-Based Metal-Organic Framework." Angew. Chem. Int. Ed., vol. 54(23), pp. 6795-6799 (2015).

Mori et al., "Hydroxyapatite-Bound Cationic Ruthenium Complexes as Novel Heterogeneous Lewis Acid Catalysts for Diels-Alder and Aldol Reactions." J. Am. Chem. Soc., vol. 125(38), pp. 11460-11461 (2003).

Moulton et al., "From molecules to crystal engineering: supramolecular isomerism and polymorphism in network solids." Chem. Rev., vol. 101, pp. 1629-1658 (2001).

Nakajima et al., "Nb2O5-nH2O as a Heterogeneous Catalyst with Water-Tolerant Lewis Acid Sites." J. Am. Chem. Soc., vol. 133(12), pp. 4224-4227 (2011).

Nicolaou et al., "The Diels-Alder Reaction in Total Synthesis." Angew. Chem. Int. Ed., vol. 41(10), pp. 1668-1698 (2002).

Ohkubo et al., "Quantitative Evaluation of Lewis Acidity of Metal Ions with Different Ligands and Counterions in Relation to the Promoting Effects of Lewis Acids on Electron Transfer Reduction of Oxygen." J. Org. Chem., vol. 68(12), pp. 4720-4726 (2003).

Park et al., "Continuous-Flow Production of Succinic Anhydrides via Catalytic β-Lactone Carbonylation by Co(CO)4⊂Cr-MIL-101." J. Am. Chem. Soc., vol. 140(34), pp. 10669-10672 (2018).

Procopio et al., "Highly efficient and versatile chemoselective addition of amines to epoxides in water catalyzed by erbium(III) triflate." Tetrahedron Lett., vol. 49(14), pp. 2289-2293 (2008).

Rehr et al., "Theoretical approaches to x-ray absorption fine structure." Rev. Mod. Phys., vol. 72(3), pp. 621-654 (2000).

Roman-Leshkov et al., "Activation of Carbonyl-Containing Molecules with Solid Lewis Acids in Aqueous Media." ACS Catal., vol. 1(11), pp. 1566-1580 (2011).

Sartori et al., Advances in Friedel-Crafts acylation reactions: catalytic and green processes. CRC Press, 2009.

Senkovska et al., "New highly porous aluminium based metal organic frameworks: Al(OH)(ndc) (ndc=2,6-naphthalene dicarboxylate) and Al(OH)(bpdc) (bpdc=4,4'-biphenyl dicarboxylate)." Microporous Mesoporous Mater, vol. 122(1), pp. 93-98 (2009).

Shinde et al., "Mild regiospecific alcoholysis and aminolysis of epoxides catalyzed by zirconium(IV) oxynitrate." Tetrahedron Lett., vol. 56(43), pp. 5916-5919 (2015).

Shustova et al., "Selective turn-on ammonia sensing enabled by high-temperature fluorescence in metal-organic frameworks with open metal sites." J. Am. Chem. Soc., vol. 135, pp. 13326-13329 (2013).

Sobanska et al., "Diagnostic Features of EPR Spectra of Superoxide Intermediates on Catalytic Surfaces and Molecular Interpretation of Their g and A Tensors." Top. Catal., vol. 58(12), pp. 796-810 (2015).

Tanaka et al., Acid-mediated reactions under microfluidic conditions: A new strategy for practical synthesis of biofunctional natural products. Beilstein J. Org. Chem., vol. 5, pp. 40 (2009).

Tang et al., "Post-synthesis of Zr-MOR as a robust solid acid catalyst for the ring-opening aminolysis of epoxides." New J. Chem., vol. 42(16), pp. 13503-13511 (2018).

Uemura et al., "Polymerization reactions in porous coordination polymers." Chem. Rev., vol. 38(5), pp. 1-9 (2009).

(56) References Cited

PUBLICATIONS

Utsunomiya et al., "Palladium-Catalyzed Equilibrium Addition of Acidic OH Groups across Dienes." Angew. Chem., vol. 115(47), pp. 5865-5868 (2003).

Vermoortele et al., "Electronic Effects of Linker Substitution on Lewis Acid Catalysis with Metal-Organic Frameworks." Angew. Chem. Int. Ed., vol. 51(20), pp. 4887-4890 (2012).

Walsh et al., "Recent Advances in Enzymatic Complexity Generation: Cyclization Reactions." Biochemistry, vol. 57(22), pp. 3087-3104 (2018).

Wiers et al., "A solid lithium electrolyte via addition of lithium isopropoxide to a metal-organic framework with open metal sites." J. Am. Chem. Soc., vol. 133, pp. 14522-14525 (2011).

Wolfe et al., "Stereoselective Synthesis of Tetrahydrofurans via the Palladium-Catalyzed Reaction of Aryl Bromides with γ-Hydroxy Alkenes: Evidence for an Unusual Intramolecular Olefin Insertion into a Pd(Ar)(OR) Intermediate." J. Am. Chem. Soc., vol. 126(6), pp. 1620-1621 (2004).

Yamamato, Lewis acids in organic synthesis. Wiley-VCH Verlag GmbH: vol. 1 (2000).

Yang, et al., "Structure and Dynamics of Zr6O8 Metal-Organic Framework Node Surfaces Probed with Ethanol Dehydration as a Catalytic Test Reaction." J. Am. Chem. Soc., vol. 140(10), pp. 3751-3759 (2018).

Yutaka et al., "One-electron Reduction of 1-Benzyl-3-carbamoylpyridinium as a NAD+ Model." Bull. Chem. Soc. Jpn., vol. 52(9), pp. 2674-2677 (1979).

Zeng et al., "Impregnation of metal ions into porphyrin-based imine gels to modulate guest uptake and to assemble a catalytic microfluidic reactor." J. Mater. Chem. A, vol. 4(21), pp. 8328-8336 (2016).

Zhang et al., "Emerging porous materials in confined spaces: from chromatographic applications to flow chemistry." Chem. Soc. Rev., vol. 48(9), pp. 2566-2595 (2019).

Zhao et al., "Highly Selective Catalytic Conversion of Phenolic Bio-Oil to Alkanes." Angew. Chem. Int. Ed., vol. 48(22), pp. 3987-3990 (2009).

Atsushi et al., "Friedel-Crafts Reactions Catalyzed by Rare Earth Metal Trifluoromethanesulfonates." Bull. Chem. Soc. Jpn., vol. 73(10), pp. 2325-2333 (2000).

Elliot, "Saturated Oxygen Heterocycles." J. Chem. Soc., Perkin Trans. 1, No. 21, pp. 2301-2323 (2002).

Gorzynski et al., "Synthetically Useful Reactions of Epoxides." Synthesis, vol. 1984(08), pp. 629-656 (1984).

Hachiya et al., "Hafnium(IV) Trifluoromethanesulfonate, An Efficient Catalyst for the Friedel-Crafts Acylation and Alkylation Reactions." Bull. Chem. Soc. Jpn., vol. 68(7), pp. 2053-2060 (1995).

Lee et al., "Metal-organic framework materials as catalysts." Chem. Soc. Rev., vol. 38(5), pp. 1450-1459 (2009).

Ravel et al., "Athena, Artemis, Hephaestus: data analysis for X-ray absorption spectroscopy using IFEFFIT." J. Synchrotron. Rad., vol. 12(4), pp. 537-541 (2005).

Woodard et al., "Total Synthesis of Steroids." J. Am. Chem. Soc., vol. 74(17), pp. 4223-4251 (1952).

\* cited by examiner

STRONGLY LEWIS ACIDIC METAL-ORGANIC FRAMEWORKS FOR CONTINUOUS FLOW CATALYSIS

RELATED APPLICATIONS

The presently disclosed subject matter claims the benefit of U.S. Provisional Patent Application Ser. No. 62/889,871, filed Aug. 21, 2019; the disclosure of which is incorporated herein by reference in its entirety.

STATEMENT OF GOVERNMENT SUPPORT

This invention was made with government support under grant number CHE-1464941 awarded by the National Science Foundation. The government has certain rights in this invention.

TECHNICAL FIELD

The presently disclosed subject matter relates to Lewis acidic metal-organic framework (MOF) materials, their preparation, and their use as heterogenous catalysts for organic transformations, including as catalysts in continuous flow reactor systems and as catalysts for tandem or cascade catalysis.

Abbreviations

° C.=degrees Celsius
%=percentage
Å=angstroms
μg=microgram
μL=microliter
μmol=micromole
Al=aluminum
Al$_2$O$_3$=alumina
bpy=2,2'-bipyridine
BTC=trimesic acid
dcbpy=2,2'-bipyridine-5,5'-dicarboxylic acid
DFT=discrete Fourier transform
DMF=dimethylformamide
DMSO=dimethylsulfoxide
DUT=Dresden University of Technology
EPR=electron paramagnetic resonance
EXAFS=extended x-ray absorption fine structure
GC-MS=gas chromatography-mass spectrometry
h=hour
Ir=iridium
kcal=kilocalories
M=molar
mg=milligram
min=minute
mL=milliliter
mm=millimeter
mM=millimolar
mmol=millimole
MOF=metal-organic framework
mol=mole
nm=nanometers
NMA=N-methylacridone
NMR=nuclear magnetic resonance
OTf=triflate (trifluoromethanesulfonate)
Pd=palladium
PXRD=powder x-ray diffraction
Ru=ruthenium
SBU=secondary building units
SEM=scanning electron microscopy
SiO$_2$=silicon dioxide
TEM=transmission electron microscopy
TFA=trifluoroacetic acid
TiO$_2$=titania
TON=turnover number
XANES=X-ray absorption near edge structure
Zr=zirconium

BACKGROUND

Metal-organic frameworks (MOFs) are an emerging class of porous molecular materials assembled from organic linkers and metal ions or metal cluster nodes.[1-10] They find application in gas storage (e.g., hydrogen, carbon dioxide, and methane storage), molecule separation, and drug delivery. MOFs can also provide a highly tunable platform to engineer heterogeneous catalysts for chemical reactions, including asymmetric organic transformations and/or transformations that cannot be achieved with traditional porous inorganic materials.[11]

However, there remains an ongoing need in the art for additional heterogeneous catalysts for catalysis. In particular, there is an ongoing need for additional Lewis acid heterogeneous catalysts.

SUMMARY

In some embodiments, the presently disclosed subject matter provides a method for preparing a catalyst, said method comprising: (a) providing a parent metal-organic framework (MOF), wherein the parent MOF comprises periodic repeats of a coordination complex comprising (i) an organic bridging ligand and (ii) a metal-containing secondary building unit (SBU), wherein said metal-containing SBU comprises a metal oxo cluster comprising a metal ion M and one or more terminal or bridging OH or OH$_2$ ligands; and (b) reacting the parent MOF with a silyl triflate to replace one or more of the one or more terminal or bridging OH or OH$_2$ ligands with a triflate ligand. In some embodiments, the SBU is selected from the group comprising an Zr-oxo cluster, an Fe-oxo cluster, a Cr-oxo cluster, and an A-oxo cluster. In some embodiments, the organic bridging ligand is substituted with one or more carboxylate, pyridine, and/or phosphonate moieties. In some embodiments, the organic bridging ligand is trimesic acid (BTC).

In some embodiments, the parent MOF is provided by contacting a parent precursor MOF with a strong acid, wherein the parent precursor MOF comprises periodic repeats of a coordination complex comprising: (i) the organic bridging ligand and (ii) a metal-containing SBU comprising a metal oxo cluster comprising the metal ion M and a monocarboxylate ligand; and wherein contacting the parent precursor MOF with the strong acid replaces the monocarboxylate ligand with an OH or OH$_2$ ligand.

In some embodiments, the organic bridging ligand comprises a nitrogen-containing aryl or arylene group that can coordinatively bond to a metal ion. In some embodiments, the parent MOF is provided by contacting a parent precursor MOF with ozone, wherein the parent precursor MOF comprises coordination complexes between a metal-containing SBU comprising a metal oxo cluster, and at least two different organic bridging ligands, wherein one of the organic bridging ligands is 2,2'-bipyridine-5,5'-dicarboxylate (dcbpy) and the other organic bridging ligand is 1,4-benzenediacrylic acid; and wherein contacting the parent precursor MOF with the ozone replaces a coordinative bond between a 1,4-benzenediacrylic acid ligand and metal ion M of the SBUs with a coordinative bond between the metal ion M of the SBU and a hydroxide ligand. In some embodiments, the method further comprises contacting the MOF with a metal complex comprising a second metal ion $M_2$, thereby metalating the nitrogen-containing aryl or arylene group of the organic bridging ligand with the second metal ion $M_2$.

In some embodiments, the catalyst is provided as a catalytic composite material and providing the parent MOF comprises providing a parent composite material by: (a1) contacting (i) one or more organic bridging ligand, (ii) a metal salt comprising a metal ion M, and (iii) silicon dioxide ($SiO_2$), alumina ($Al_2O_3$), or titania ($TiO_2$) particles in a mixture of N,N-dimethylformamide and a monocarboxylic acid to form a parent precursor composite material, wherein the parent precursor composite material comprises particles of a parent precursor MOF attached to a surface of the $SiO_2$, $Al_2O_3$, or $TiO_2$ particles, wherein said parent precursor MOF comprises periodic repeats of a coordination complex comprising the one or more organic bridging ligand and metal-containing secondary building units (SBUs), wherein the metal-containing SBUs each comprise a metal oxo cluster comprising the metal ion M and further comprising a monocarboxylate ligand; and (a2) reacting the parent precursor composite material with a strong acid to replace the monocarboxylate ligand with a hydroxide ligand, thereby forming the parent composite material comprising the parent MOF; and wherein reacting the parent MOF with a silyl triflate comprises reacting the parent composite material with a silyl triflate, thereby replacing the hydroxide ligand with a triflate ligand.

In some embodiments, the catalyst is provided as a catalytic composite material and providing the parent MOF comprises providing a parent composite material by: (a1) contacting 2,2'-bipyridine-5,5'-dicarboxylate (dcbpy), 1,4-benzenediacrylic acid, and an aluminum salt in the presence silicon dioxide ($SiO_2$), alumina ($Al_2O_3$), or titania ($TiO_2$) particles to form a parent precursor composite material, wherein the parent precursor composite material comprises particles of a parent precursor MOF attached to a surface of the $SiO_2$, $Al_2O_3$, or $TiO_2$ particles, wherein said parent precursor MOF comprises coordination complexes between an Al-oxo cluster secondary building unit (SBU) and both the dcbpy and the 1,4-benzenediacrylic acid, and (a2) reacting the parent precursor composite material with ozone, to replace coordinative bonds between the 1,4-benzenediacrylic acid and Al ions of the SBU with coordinative bonds between the Al ions and a hydroxide ligand, thereby forming a parent composite material comprising the parent MOF; and wherein reacting the parent MOF with a silyl triflate comprises reacting the parent composite material with (i) a silyl triflate, thereby replacing the hydroxide ligand with a triflate ligand; and (ii) a metal complex thereby metalating the bipyridine group of the dcbpy ligand.

In some embodiments, the presently disclosed subject matter provides a MOF catalyst prepared by a method comprising: (a) providing a parent MOF, wherein the parent MOF comprises periodic repeats of a coordination complex comprising (i) an organic bridging ligand and (ii) a metal-containing SBU, wherein said metal-containing SBU comprises a metal oxo cluster comprising a metal ion M and one or more terminal or bridging OH or $OH_2$ ligands; and (b) reacting the parent MOF with a silyl triflate to replace one or more of the one or more terminal or bridging OH or $OH_2$ ligands with a triflate ligand.

In some embodiments, the presently disclosed subject matter provides a MOF catalyst, wherein the MOF catalyst comprises periodic repeats of a coordination complex comprising: (a) an organic bridging ligand; and (b) a metal-containing SBU, wherein the SBU comprises a metal ion M and one or more metal ion ligands, wherein one or more of the metal ion ligands comprises a triflate ligand. In some embodiments, the organic bridging ligand comprises a nitrogen-containing aryl or arylene group complexed to a second metal ion $M_2$, optionally wherein $M_2$ is a Pd, Ir, or Ru ion.

In some embodiments, the presently disclosed subject matter provides a heterogenous catalyst comprising a modified $SiO_2$ material, wherein the modified $SiO_2$ catalyst material comprises $SiO_2$ particles, and wherein one or more $SiO_2$ particles comprise a surface wherein one or more MOF particles are attached, wherein said one or more MOF particles each comprise periodic repeats of a coordination complex comprising (i) an organic bridging ligand, and (ii) a metal-containing SBU, wherein said SBU comprises a metal oxo cluster of a metal ion M and one or more triflate ligands. In some embodiments, the organic bridging ligand comprises a nitrogen-containing aryl or arylene group coordinated to a second metal $M_2$.

In some embodiments, the presently disclosed subject matter provides a method for performing an organic group transformation, the method comprising contacting a substrate capable of forming a product by catalytic transformation with a MOF catalyst, wherein said MOF catalyst comprises periodic repeats of a coordination complex comprising: (a) an organic bridging ligand; and (b) a metal-containing secondary building unit (SBU), wherein the SBU comprises a metal ion M and one or more metal ion ligands, wherein one or more of the metal ion ligands comprises a triflate ligand, or a catalytic composite material thereof wherein the MOF catalyst is attached to the surface of a silcon dioxide particle, a titania particle, or an alumina particle. In some embodiments, the catalytic transformation is selected from the group comprising a Diels-Alder reaction, an epoxide ring-opening amination, a Friedel Crafts acylation reaction, and an alkene hydroalkoxylation reaction. In some embodiments, the catalytic transformation is conducted in a batch reactor, a continuous flow reactor, or in a supercritical fluid reactor.

In some embodiments, the catalytic transformation is a tandem C—O bond cleavage reaction, wherein said MOF catalyst comprises an organic bridging ligand comprising a nitrogen-containing aryl or arylene group metallated with a second metal $M_2$, and wherein the substrate is selected from an ether, an alcohol, a carboxylic acid, and an ester, thereby performing a tandem hydrodeoxygenation reaction, a tandem Lewis acid and photoredox catalysis of a decarboxylolefination of a carboxylic acid, or a reductive coupling of an alkenylpyridine with an aldehyde or imine. In some embodiments, the substrate is an intermediate or product of a biomass conversion process.

Accordingly, it is an object of the presently disclosed subject matter to provide methods of preparing MOF catalysts comprising metal ion triflate ligands, and methods of preparing composite materials thereof, as well as to provide the MOF catalysts, related composites, and methods of performing organic group transformations, such as tandem C—O bond cleavage reactions, using the MOF catalysts and composites.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

DETAILED DESCRIPTION

Figure 1:
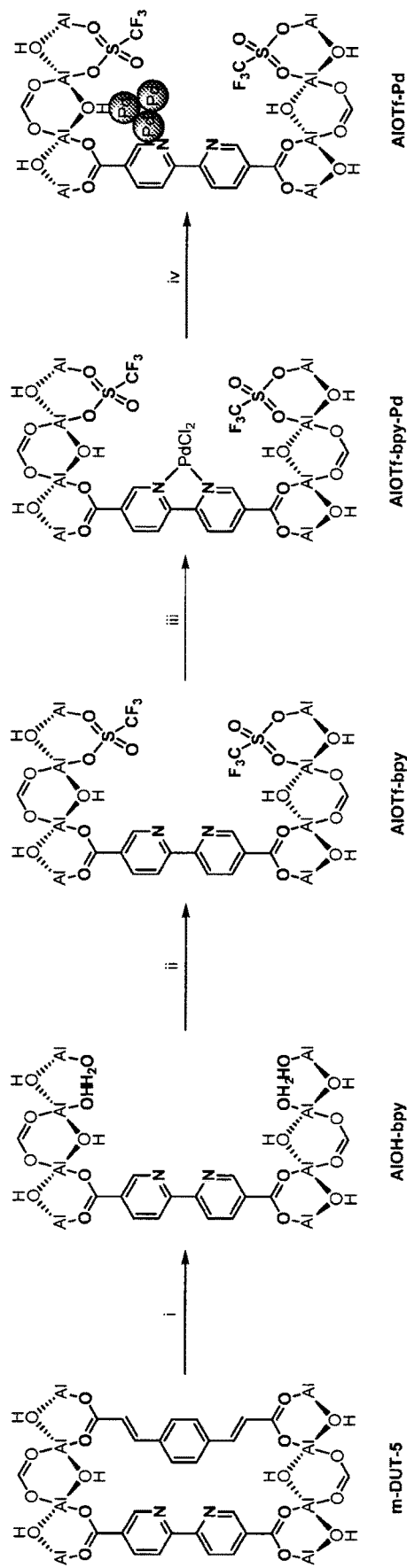
FIG. 1 is a schematic drawing showing step-by-step post-synthetic transformations of a metal-organic framework (MOF) comprising aluminum metal centers and 2,2'-bipyridine-5,5'-dicarboylic acid (dcbpy) bridging ligands, referred to as m-DUT-5, to provide a MOF comprising triflate metal ligands and metalated bridging ligands, referred to as AlOTf-Pd. The reaction conditions include: i) zone ($O_3$) treatment followed by washing with a mixture of hydrochloric acid (HCl) in dimethylformamide (DMF) (i.e., 1 molar (M) HCl in DMF); ii) trimethylsilyl triflate ($(CH_3)_3$SiOTf) in toluene, room temperature (r.t.), overnight; iii) bis(acetonitrile)dichloro palladium(II) ($PdCl_2(CH_3CN)_2$) in tetrahydrofuran (THF), r.t., overnight; and iv) in situ hydrogen ($H_2$) treatment.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example±20% or 10%, in another example±5%, in another example±1%, and in still another example±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. For example, nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "aralkylene" refers to a bivalent aralkyl group. The aralkylene group can optionally be substituted with one or more alkyl or aryl group substituents and/or include one or more heteroatoms.

The term "olefin" refers to a compound with a carbon-carbon double bond.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "amine" refers to compounds or ligands for metals having the formula $N(R)_3$ wherein each R is independently H, alkyl, substituted alkyl, aryl, substituted aryl, aralkyl, or substituted aralkyl.

The terms "halo", "halide", or "halogen" as used herein refer to fluoro, chloro, bromo, and iodo groups.

The terms "hydroxyl" and "hydroxyl" refer to the —OH group.

The term "alkoxy" refers to the —OR group, where R is alkyl or substituted alkyl.

The term "aryloxy" refers to the —OR group where R is aryl or substituted aryl.

The terms "mercapto" or "thiol" refer to the —SH group.

The terms "carboxylate" and "carboxylic acid" can refer to the groups —C(=O)O⁻ and —C(=O)OH, respectively. In some embodiments, "carboxylate" can refer to either the —C(=O)O— or —C(=O)OH group.

The term "phosphonate" refers to the —P(=O)(OR)$_2$ group, wherein each R can be independently H, alkyl, substituted alkyl, aralkyl, substituted aralkyl, aryl, substituted aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

As used herein, the term "metal-organic matrix material" refers to a solid material comprising both metal and organic components, wherein the organic components include at least one, and typically more than one carbon atom. In some embodiments, the material is crystalline. In some embodiments, the material is porous. In some embodiments, the metal-organic matrix material is a coordination polymer, which comprises repeating units of coordination complexes comprising a metal-based secondary building unit (SBU), such as a metal ion, metal cluster, or metal complex, and a bridging polydentate (e.g., bidentate) organic ligand. In some embodiments, the material contains more than one type of metal ion. In some embodiments, the material can contain more than one type of organic bridging ligand.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles. In some embodiments, in addition to binding to at least two metal ions or complexes in an MOF, the bridging ligand can also bind to a further metal ion or complex, e.g., to provide a catalytic moiety.

As used herein, turnover number (TON) refers to the number of moles of substrate that a mole of catalyst can convert before being inactivated.

As used herein, the term "stable" refers to a characteristic of a MOF of the presently disclosed subject matter. A "stable" MOF refers to a MOF that retains its framework structure during the catalytic reaction; such stability can be manifested by the retention of the powder X-ray diffraction pattern after the catalytic reaction. In some embodiments, the term "stable" refers to the characteristic that the MOF does not leach metal to a measurable extent, e.g., during a catalytic reaction. In some embodiments, the term "stable" refers to the characteristic that the MOF comprises a O-metal bond that is stable wherein the O-metal bond is present in a SBU of a MOF, but would disproportionate if not present in the MOF.

The terms "Lewis acid" and "Lewis acidic" refer to groups or species able to accept an electron pair from an electron pair donor (i.e., a "Lewis" base) to form an adduct.

The term "strong acid" refers to an acid that completely dissociates in water, e.g., HCl, HBr, HI, $HNO_3$, $HClO_4$, and $H_2SO_4$.

II. General Considerations

Lewis acids efficiently catalyze many different types of organic reactions by withdrawing electron density from functional groups to make them susceptible to nucleophilic attacks.[12-14] In Diels-Alder reactions, for example, coordination of a dienophile to a Lewis acid significantly decreases its LUMO energy to facilitate its reaction with a diene.[15] Catalytic Diels-Alder reactions allow for efficient synthesis of functionalized cyclic compounds that have found widespread use as pharmaceutical ingredients, artificial flavors, fragrances, and agrochemicals.[16] Lewis acids are also used to catalyze the formation of epoxides and aromatic ketones and regioselective ring opening of epoxides to yield alcohols.

Early Lewis acid catalysts were typically based on main group or early transition metal halides. However, these Lewis acidic metal salts tend to have low solubility in nonpolar organic solvents, are sensitive to moisture, and have short lifetimes during catalysis. Thus, researchers have devoted significant efforts to developing heterogeneous Lewis acid catalysts such as zeolites, metal oxides and resins over the past few decades. Solid acid catalysts can be readily separated from reaction mixtures for reuse and are compatible with flow catalysis,[17-19] but they have moderate Lewis acidity, low active site density, and non-uniform active sites.[20-21]

Metal-organic frameworks (MOFs) have recently emerged as porous material platforms for designing homogeneously inaccessible catalysts by taking advantage of their regular framework structures and site isolation effects.[22-27] In particular, metal centers in MOF nodes have afforded single-site solid catalysts with unique electronic properties and steric environments that are not accessible via conventional homogeneous chemistry or heterogenization approaches. Although MOF nodes have been used as Lewis acidic sites to catalyze organic transformations, such as cyclization reactions,[28] C—H iodinations,[29] hydrolysis,[30-31] and dehydrations,[32] using activated substrates, Lewis acidity of these metal sites is significantly lower than the homogeneous benchmark $Sc(OTf)_3$.[33]

The present disclosed subject matter provides metal-organic frameworks (MOFs) comprising metal-containing secondary building units (SBUs) and organic bridging ligand, where the SBUs have been post-synthetically modified, e.g., via replacement of a terminal OH or $OH_2$ ligand with a triflate ligand (i.e., $CF_3SO_3$—), to provide Lewis acidic heterogenous catalysts. For example, the MOFs act as highly active solid Lewis acid catalysts for a broad range of organic transformations, including Diels-Alder reactions, epoxide ring-opening reactions, Friedel-Crafts acylations, and alkene hydroalkoxylation reactions. As described in the Examples below, the Lewis acidity of the MOF active sites can be quantitative measured, for example, through electron paramagnetic resonance (EPR) spectroscopy of MOF-bound superoxide ($O_2$*$^-$) or fluorescence spectroscopy of MOF-bound N-methylacridone (NMA).[29] In some embodiments, the presently disclosed Lewis acid MOF catalysts have higher Lewis acidity than $Sc(OTf)_3$ and outperforms $Sc(OTf)_3$ by providing higher catalytic activity and longer catalyst lifetime.

In some embodiments, the MOFs further comprise a metallated organic bridging ligand and can be used to perform tandem reactions, including tandem C—O bond cleavage reactions, e.g., hydrodeoxygenation reactions. See Example 1, below. In some embodiments, the organic bridging ligand can be metallated with a group that can act as a photosensitizer, e.g., an Ir or Ru atom with bipyridine or phenylpyridine ligands, and the MOF can be used in tandem Lewis acid/photoredox reactions.

Thus, in some embodiments, the presently disclosed subject matter provides a method of preparing a catalyst comprising a MOF, wherein the MOF comprises a SBU, e.g., an aluminum, chromium, iron, or zirconium oxocluster, with a triflate ligand. In some embodiments, the presently disclosed subject matter provides the MOF catalysts themselves. The presently disclosed subject matter further provides composite materials, e.g., for use in continuous flow reactors, wherein the Lewis acidic MOFs are present on the surface of particles such as $SiO_2$, $Al_2O_3$, or $TiO_2$ particles. In some embodiments, the presently disclosed subject matter relates to methods of using the catalysts or composite materials.

III. Lewis Acidic MOF Catalysts, Catalytic Composite Materials and Method of Preparation In some embodiments, the presently disclosed subject matter provides a method for preparing a catalyst comprising a Lewis acidic MOF comprising a metal-containing secondary building unit (e.g., a metal oxo cluster) comprising a triflate-coordinated metal ion. In some embodiments, the method comprises post-synthetically modifying a "parent" MOF comprising an SBU comprising a metal oxo cluster comprising a metal ion M and one or more terminal or bridging OH of $OH_2$ ligands. For instance, in some embodiments, the method comprises: (a) providing a "parent" MOF, wherein the parent MOF comprises periodic repeats of a coordination complex comprising (i) an organic bridging ligand and (ii) a metal-containing secondary building unit (SBU), wherein said metal-containing SBU comprises a metal oxo cluster comprising a metal ion M and one or more terminal or bridging OH or $OH_2$ ligands; and (b) reacting the parent MOF with a silyl triflate to replace one or more of the one or more terminal or bridging OH or $OH_2$ ligands with a triflate ligand, thereby providing a MOF comprising periodic repeats of a coordination complex comprising the organic bridging ligand and an SBU comprising a metal oxo cluster comprising the metal ion M and one or more triflate ligand. In some embodiments, the triflate ligand in the product MOF is coordinated to two different metal ions in the SBU via two different oxygen atoms of the triflate ligand.

Any suitable silyl triflate can be used. Generally, silyl triflates have the formula $R_3Si-O-S(=O)_2-CF_3$, where each R is independently alkyl, substituted alkyl, aralkyl, substituted aralkyl, aryl or substituted aryl. In some embodiments, each R is independently alkyl (e.g., C1-C6 straight or branched alkyl), aralkyl (e.g., benzyl) or aryl (e.g., phenyl). Exemplary silyl triflates include, but are not limited to, trimethylsilyl triflate, triethylsilyl triflate, triisopropylsilyl triflate, t-butyldimethylsilyl triflate, or t-butyldiphenylsilyl triflate. In some embodiments, the silyl triflate is trimethylsilyl triflate.

The MOF SBU can comprise any metal oxo cluster. In some embodiments, the MOF SBU is an oxo cluster of a transition metal or of aluminum (Al). For instance, the SBU can be selected from the group comprising Hf-oxo clusters, Zr-oxo clusters, Zn-oxo clusters, Al-oxo clusters, a Cr-oxo clusters, a Fe-oxo clusters and Ti-oxo clusters. In some embodiments, the SBU is a Zr-oxo cluster, an Al-oxo cluster, a Cr-oxo cluster, or a Fe-oxo cluster. Thus, in some embodiments, M is selected from Zr, Al, Cr, and Fe. In some embodiments, M is Zr or Al.

The organic briding ligand can be any suitable organic briding ligand. For example, the organic bridging ligand can comprise one or more metal chelating groups, such as carboxylate, pyridine, or phosphate moieties. However, the organic briding ligands are not limited to these metal chelating groups. Other suitable metal chelating groups that can be included as substituents or as parts of the organic bridging ligand include, but are not limited to, nitro (—$NO_2$), amino (—$NH_3$), hydroxyl (e.g., phenol), thio, thioalkyl, —$B(OH)_2$, —$SO_3H$, phosphonate, and heterocycles other than pyridine. Generally, the organic bridging ligand is a polydentate metal chelator, i.e., an organic ligand comprising two or more metal chelating groups, which can be the same or different. Thus, the organic briding ligand can coordinatively bond to metal ions in two different SBUs. In some embodiments, the organic briding ligand includes two, three, or four metal chelating groups (e.g., carboxylate, pyridine, and/or phosphate groups) In some embodiments, the organic bridging ligand is a dicarboxylate, a tricarboxylate, or at tetracarboxylate.

The organic bridging ligand can further include an alkylene, aralkylene, or arylene group on which the metal chelating groups are substituted. In some embodiments, the organic briding ligand further comprises an aryl or arylene group. For example, in some embodiments, the organic briding ligand comprises a phenyl, pyridine, biphenyl, bipyridine, naphthyl, phenanthrenyl, or terphenyl group substituted by at least two metal chelating groups (e.g., carboxylate, phosphate, etc.). In some embodiments, the organic bridging ligand comprises a nitrogen-containing aryl or arylene group (i.e., a nitrogen-containing heteroaryl or heteroarylene group) that can coordinatively bond to a metal ion (e.g., an additional metal ion not associated with a SBU of the MOF), such as, but not limited to, bipyridine, phenanthroline, terpyridine, salicylaldiminie, pyridylphenyl, 1,3-diketimine (NacNac), bis(oxazoline), and the like, wherein the nitrogen-containing aryl or arylene group is substituted by one or more metal chelating groups (e.g., carboxylate, phosphate, etc.).

In some embodiments, the organic briding ligand is trimesic acid (BTC), also known as benzene-1,3,5-tricarboxylic acid. In some embodiments, the organic bridging ligand is 2,2'-bipyridine-5,5'-dicarboxylate (dcbpy).

In some embodiments, the MOF comprises more than one type of organic bridging ligand. In some embodiments, at least one organic briding ligand comprises a nitrogen-containing aryl or arylene group that can coordinatively bond to a metal ion, such as, but not limited to, bipyridine, phenanthroline, terpyridine, salicylaldiminie, pyridylphenyl, 1,3-diketimine (NacNac), and bis(oxazoline). In some embodiments, the MOF comprises at least one organic briding ligand comprising a nitrogen-containing aryl or arylene group and at least one organic ligand that does not comprise such a group (e.g., that comprises an aryl or arylene group that does not comprise a heteroatom). In some embodiments, the MOF comprises a mixture of organic briding ligands comprising dcbpy and 1,4-benzenediacrylic acid. In some embodiments, the ratio of dcbpy and 1,4-benzenediacrylic acid is about 4:1 dcbpy:1,4-benzenediacrylic acid.

In some embodiments, the parent MOF is provided by contacting a parent precursor MOF with a strong acid to replace a moncarboxylate metal ligand of an SBU with a OH or $OH_2$ ligand. Thus, for example, the parent precursor MOF can be a MOF that comprises periodic repeats of a coordination complex comprising (i) the organic briding ligand and (ii) a metal-containing SBU comprising a metal oxo cluster comprising the metal ion M and a monocarboxylate ligand. In some embodiments, the monocarboxylate ligand is a formate or trifluoroacetate ligand. In some embodiments, the strong acid is HCl.

In some embodiments, the parent MOF is provided by contacting a parent precursuor MOF with ozone. For example, in some embodiments, the parent precursor MOF comprises coordination complexes between a metal-containing SBU comprising a metal oxo cluster and at least two different organic bridging ligands, wherein one of the organic bridging ligands is 1,4-benzenediacrylic acid (or another ozone-reactive organic bridging ligand); and wherein contacting the parent precursor MOF with the ozone replaces a coordinative bond between a ligand (e.g., the 1,4-benzenediacrylic acid ligand) and metal ion M of the SBUs with a coordinative bond between the metal ion M of the SBU and a hydroxide ligand. In some embodiments, the SBU of the parent precursor MOF comprises an Al-oxo cluster. In some embodiments, one of the organic bridging ligands is 2,2'-bipyridine-5,5'-dicarboxylate (dcbpy) or another organic bridging ligand comprising a nitrogen-containing aryl or arylene group and the other organic bridging ligand is 1,4-benzenediacrylic acid. In some embodiments, the ratio of dcbpy to 1,4-benzenediacrylic acid is about 4:1.

In some embodiments, when the MOF comprises an organic bridging ligand that comprises a nitrogen-containing aryl or arylene group that can coodinatively bond to a metal, the method further comprises contacting the MOF (i.e., the MOF comprising the triflate ligand) with a metal complex comprising a second metal ion $M_2$, thereby metalating the nitrogen-containing aryl or arylene group of the organic bridging ligand with the second metal ion $M_2$. The second metal ion can have catalytic activity. Thus, the further metallated MOF can comprises two different catalytic activities, one from the Lewis acidic site on the SBU and one from the second metal ion $M_2$. In some embodiments, the metal complex comprising $M_2$ is a palladium, iridium, or ruthenium metal complex. In some embodiments, the metal complex comprising $M_2$ is selected from $PdCl_2(CH_3CN)_2$, Ir(2-phenylpyridine)$_2$Cl, or Ru(2,2'-bipyridine)Cl$_2$.

In some embodiments, the presently disclosed subject matter provides a MOF catalyst prepared according to a method as described above, i.e., a MOF catalyst prepared by post-synthetically replacing a SBU OH or $OH_2$ ligand with a triflate ligand by reacting a MOF comprising a SBU with a terminal OH or $OH_2$ ligand with a silyl triflate.

In some embodiments, the presently disclosed subject matter provides a MOF catalyst wherein the MOF catalyst comprises: (a) an organic bridging ligand; and (b) a metal-containing secondary building unit (SBU), wherein the SBU comprises a metal ion M and one or more metal ion ligands, wherein one or more of the metal ion ligands comprises a triflate ligand. In some embodiments, M is selected from Al and a transition metal. In some embodiments, M is selected from Al, Zr, Cr, and Fe. In some embodiments, M is Al or Zr. The organic bridging ligand can be any suitable organic bridging ligand as described hereinabove, such as an aryl or arylene substituted by two, three, or four metal chelating groups (e.g., carboxylate groups). In some embodiments, the MOF catalyst can comprise more than one type of organic bridging ligand. In some embodiments, the MOF catalyst comprises at least one organic bridging ligand selected from BTC and dcbpy. In some embodiments, at least one organic bridging ligand comprises a nitrogen-containing aryl or arylene group (e.g., a bipyridine group) complexed to a second metal ion $M_2$. In some embodiments, $M_2$ is selected from a Pd, Ir, or Ru ion.

The presently disclosed subject matter further provides composites comprising the MOFs. For instance, in some embodiments, the MOF catalyst is provided as a catalytic composite material comprising 1) the MOF comprising one or more SBU metal triflate ligand and 2) another, generally non-catalytic support material. In some embodiments, the presently disclosed subject matter provides a method of making a composite material comprising a Lewis acidic MOF of the presently disclosed subject matter. For example, the composite material can comprise inactive support particles modified with the Lewis acidic MOF (e.g., having Lewis acidic MOF particles associated with the surface of the support particles). Exemplary support particles comprise materials such as, but not limited to silicon dioxide ($SiO_2$) particles, alumina ($Al_2O_3$) particles, and titania ($TiO_2$) particles or any other particle that can be used as a packing material for a column of a continuous flow reactor. In some embodiments, the support particles can be added to a reaction mixture during the preparation of a parent MOF or parent precursor MOF of the presently disclosed Lewis acidic MOFs.

For instance, in some embodiments, with respect to the method of preparing a catalyst described hereinabove, when the catalyst is provided as a catalytic composite material, providing the parent MOF can comprise providing a parent composite material comprising the parent MOF. In some embodiments, providing the parent composite material comprises: (a1) contacting (i) one or more organic bridging ligand, (ii) a metal salt comprising a metal ion M, and (iii) silicon dioxide ($SiO_2$), alumina ($Al_2O_3$), or titania ($TiO_2$) particles in a mixture of a solvent (e.g., N,N-dimethylformamide (DMF)) and a monocarboxylic acid, to form a parent precursor composite material, wherein the parent precursor composite material comprises particles of a parent precursor MOF attached to a surface of the $SiO_2$, $Al_2O_3$, or $TiO_2$ particles, wherein said parent precursor MOF comprises periodic repeats of a coordination complex comprising the one or more organic bridging ligand and metal-containing secondary building units (SBUs), wherein the metal-containing SBUs each comprise a metal oxo cluster comprising the metal ion M and further comprising a monocarboxylate ligand; and (a2) reacting the parent precursor composite material with a strong acid to replace the monocarboxylate ligand with a hydroxide ligand, thereby forming a parent composite material comprising the parent MOF. In some embodiments, reacting the parent MOF with a silyl triflate comprises reacting the parent composite material with a silyl triflate, thereby replacing the hydroxide ligand with a triflate ligand and providing a catalytic composite material comprising a Lewis acidic MOF.

The one or more organic bridging ligands can be any organic bridging ligand as described hereinabove. In some embodiments, the one or more organic bridging ligand is an aryl polycarboxylate, such as an aryl di- or tricarboxylate. In some embodiments, the one or more organic bridging ligands comprise BTC. In some embodiments, M is Al or a transition metal (e.g., Zr, Cr, or Fe). In some embodiments, the metal salt is $ZrOCl_2$.

In some embodiments, the monocarboxylic acid is selected from formic acid and trifluoroacetic acid. Thus, in some embodiments, the monocarboxylate ligand can be a formate or trifluoroacetate ligand. In some embodiments, the strong acid in step (a2) is HCl. In some embodiments, the silyl triflate is trimethylsilyl triflate.

In some embodiments, the catalytic composite material can be prepared by mixing the support particles in a mixture comprising a metal salt, at least two organic bridging ligands, one of which comprises a nitrogen-containing aryl or arylene group and the other being a ligand that has a group (e.g., a double bond) that can react with ozone, such as 1,4-benzenediacrylic acid to provide a parent precursor material that can be reacted with ozone to replace the ozone reactive organic briding ligand with SBU terminal OH or OH$_2$ groups, which can themselves be replaced by triflate ligands. The composite can also be post-synthetically metallated at the nitrogen-containing aryl or arylene group to provide a second catalytic site.

Accordingly, in some embodiments, the parent composite material can be prepared by: (a1) contacting 2,2'-bipyridine-5,5'-dicarboxylate (dcbpy), 1,4-benzenediacrylic acid, and an aluminum salt in the presence silicon dioxide (SiO$_2$), alumina (Al$_2$O$_3$), or titania (TiO$_2$) particles to form a parent precursor composite material, wherein the parent precursor composite material comprises particles of a parent precursor MOF attached to a surface of the SiO$_2$, Al$_2$O$_3$, or TiO$_2$ particles, wherein said parent precursor MOF comprises coordination complexes between an Al-oxo cluster secondary building unit (SBU) and both the dcbpy and the 1,4-benzenediacrylic acid; and (a2) reacting the parent precursor composite material with ozone, to replace coordinative bonds between the 1,4-benzenediacrylic acid and Al ions of the SBU with coordinative bonds between the Al ions and a hydroxide ligand, thereby forming a parent composite material. In some embodiments, the parent composite material can be reacted with (i) a silyl triflate, thereby replacing the hydroxide ligand with a triflate ligand; and (ii) a metal complex, thereby metalating the bipyridine group of the dcbpy ligand. In some embodiments, the silyl triflate is trimethylsilyl triflate. In some embodiments, the metal complex is a transition metal complex. In some embodiments, the metal complex is a palladium, iridium, or ruthenium metal complex, such as, but not limited to, PdCl$_2$(CH$_3$CN)$_2$, Ir(2-phenylpyridine)$_2$Cl, and Ru(2,2'-bipyridine)Cl$_2$.

In some embodiments, the presently disclosed subject matter provides a catalytic composite material prepared according to a method as described herein. In some embodiments, the presently disclosed subject matter provides a heterogenous catalyst comprising a modified silica, titania, or alumina material, wherein the modified material comprises silica, titania, or alumina particles that comprise a surface modified by one or more MOF particles attached thereto, wherein said one or more MOF particles each comprise periodic repeats of a coordination complex comprising (i) an organic bridging ligand (e.g., BTC or dcbpy), and (ii) a metal-containing secondary building unit (SBU), wherein said SBU comprises a metal oxo cluster of a metal ion M (e.g., Al or a transition metal, such as Zr, Cr, or Fe) and one or more triflate ligands. In some embodiments, the heterogenous catalyst comprises a modified SiO$_2$ material, wherein the modified SiO$_2$ catalyst material comprises SiO$_2$ particles, and wherein one or more SiO$_2$ particles comprise a surface wherein one or more MOF particles are attached, wherein said one or more MOF particles each comprise periodic repeats of a coordination complex comprising (i) an organic bridging ligand (e.g., BTC or dcbpy), and (ii) a metal-containing secondary building unit (SBU), wherein said SBU comprises a metal oxo cluster of a metal ion M (e.g., Al, Zr, Cr, or Fe) and one or more triflate ligands. In some embodiments, the organic briding ligand comprises a nitrogen-containing aryl or arylene group. In some embodiments, the organic bridging ligand comprises dcbpy. In some embodiments, the organic briding ligand is a nitrogen-contining aryl or arylene group coordinated to a second metal M$_2$. In some embodiments, M$_2$ is a Pd, Ir, or Ru ion.

IV. Catalytic Reactions

The presently disclosed Lewis acidic MOF catalysts and their composite materials find use as heterogenous catalysts for a variety of organic group transformations that can be catalyzed by a Lewis acid, such as, but not limited to Diels-Alder reactions, epoxide ring-opening amination reactions, Friedel Crafts acylation reactions, and alkene hydroalkoxylation reactions, either in batch or continuous flow mode. In some embodiments, when the MOF catalyst comprises a second metal ion M$_2$, the catalyst and their composites can be used to catalyze tandem reactions, e.g., tandem hydrodeoxygenation reactions, tandem Lewis acid/photoredox catalyzed decarboxylolefinations of carboxylic acids, and reductive coupling reactions of alkenylpyridines with aldehydes or imines.

Accordingly, in some embodiments, the presently disclosed subject matter provides a method for performing an organic group transformation, the method comprising contacting one or more substrates capable of forming a product by catalytic transformation with a catalyst comprising a MOF comprising comprise periodic repeats of a coordination complex comprising (i) an organic bridging ligand, and (ii) a metal-containing secondary building unit (SBU), wherein said SBU comprises a metal oxo cluster of a metal ion M and one or more triflate ligands. For example, the catalyst can be a MOF prepared by a method of the presently disclosed subject matter as described hereinabove (e.g., by replacing one or more terminal or bridging OH or OH$_2$ ligands) of a MOF SBU with a triflate ligand). In some embodiments, the metal ion M is selected from Zr, Al, Fe, and Cr. In some embodiments, the metal ion M is Zr or Al. In some embodiments, the organic bridging ligand is BTC or dcbpy. In some embodiments, the catalyst can be a catalytic composite material comprising the MOF attached at the surface of a support material, such as silicon dioxide, titania, or alumina particles. In some embodiments, the MOF comprises at least one organic bridging ligand (e.g., dcbpy) comprising a nitrogen-containing aryl or heteroaryl group (e.g., bipyridine) and the organic briding ligand is metallated with a second metal ion M$_2$ (e.g., Pd, Ir, or Ru).

In some embodiments, the catalytic transformation is a Diels-Alder reaction and the substrate comprises a conjugated diene and a substituted alkene (e.g., an α,β-unsaturated ketone or aldehyde). In some embodiments, the catalytic transformation is an epxoide ring-opening amination and the substrate comprises an epoxide and an amine (e.g., an aromatic amine). In some embodiments, the catalytic transformation is a Friedel Crafts acylation and the substrate is a substituted or unsubstituted arene and an anhydride. In some embodiments, the catalytic transformation is an alkene hydroalkoxylation reaction (e.g., an intramolecular alkene hydroalkoxylation) and the substrate is a hydroxy-substituted alkene. Thus, the products of the catalytic transformations can include cyclohexens, acylated arenes, amino alcohols, and cyclic ethers.

In some embodiments, the presently disclosed subject matter provides a method of performing a tandem C—O bond cleavage reaction, the method comprising contacting a substrate with the MOF catalyst or composite wherein the MOF catalyst comrpsies (i) an organic bridging ligand, and (ii) a metal-containing secondary building unit (SBU), wherein said SBU comprises a metal oxo cluster of a metal ion M and one or more triflate ligands; and further wherein the organic bridging ligand comprises a nitrogen-containing aryl or arylene group that is metallated with a second metal M$_2$, e.g., Pd, Ir, or Ru, and wherein the substrate is selected from an ether, an alcohol, a carboxylic acid, and an ester, thereby performing a tandem hydrodeoxygenation reaction, a tandem Lewis acid and photoredox catalysis of a decarboxylolefination of a carboxylic acid, or a reductive coupling of an alkenylpyridine with an aldehyde or imine. In some embodiments, the substrate of the organic transformations catalyzed by the presently disclosed MOFs or composites is an intermediate or product of a biomass conversion process. For example, in some embodiments, the catalysts or composites of the presently disclosed subject matter can be used in biomass hydrodeoxygenation.

The catalytic transformations can be conducted in a batch reactor, a continuous flow reactor, or in a super critical fluid reactor. In some embodiments, the MOF catalyst is provided as a composite with silicon dioxide particles, titania particles or alumina particles. In some embodiments, the composite is packed in a column or other reaction chamber of a continuous flow reactor into which a solvent or solvents can be pumped in and out and wherein the solvent or solvents can comprise a substrate or substrates dissolved therein.

The contacting of the MOF (or composite thereof) and the substrate(s) can take place in any suitable solvent, e.g., a solvent in which the substrate can be dissolved. In some embodiments, the solvent is an ether, such as tetrahydrofuran or dioxane; an alkane, such as a hexane (e.g., n-hexane), a heptane (e.g., n-heptane), or an octane (e.g., n-octane); a halogenated alkene, such as dichloromethane, dichloroethane, or chloroform; an aromatic solvent, such as benzene, toluene, or a xylene; DMF, dimethylsulfoxide (DMSO), an alcohol, such as methanol or ethanol; water, or mixtures thereof. In some embodiments, the solvent is an unconventional solvent, such as supercritical carbon dioxide. In some embodiments, no solvent is present (i.e., the reaction is performed "neat"). In some embodiments, the contacting takes place in the presence of a gas, such as hydrogen gas, and/or under pressure. In some embodiments, the contacting is done in conjunction with heating or cooling.

The presently disclosed catalysts can have high turnover number (TON). For example, in some embodiments, the presently disclosed MOF-based catalysts can have a TON of greater than about 50, greater than about 100, greater than about 200, greater than about 300, greater than about 400, greater than about 500, greater than about 750, greater than about 1000, greater than about 1500, greater than about 2000, or greater than about 2500. For instance, the catalysts can have a TON for tandem reactions of about 800, a TON for Diels-Alder reactions of about 1600, a TON for Friedel-Crafts acylations of about 326, or a TON for an epoxide-ring opening animation of about 2700.

In some embodiments, the yields of the catalytic transformations can be at least about 64%. In some embodiments, the yields can be about 80% or higher (e.g., about 80, 85, 90, 91, 92, 93, 94, 95, 96, 97, 98, or 99% or greater).

In some embodiments, the presently disclosed catalysts can be used at low catalyst loadings, e.g., at less than about 10 mole %, less than about 5 mole %, less than about 4 mole %, less than about 3 mole %, less than about 2 mole %, less than about 1 mole %, less than about 0.5 mole %, or less than about 0.2 mole % compared to the substrate. In some embodiments, the catalysts can be used at a catalyst loading of between about 0.1 mole % and about 5 mole %. In some embodiments, the catalysts can be used at a catalyst loading of between about 0.1 mole % and about 0.5 mole % (e.g., at about 0.1, 0.2, 0.3, 0.4, or about 0.5 mole %). In some embodiments, the catalyst loading can be about 1 mole % to about 5 mole % (e.g., 1.1, 1.5, 2.0, 2.5, 3.0, 3.5, 4.0, 4.5, or about 5.0 mole

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

AlOTf-Pd and Tandem C—O Bond Cleavage Reactions Catalyzed Thereby

MOF SBUs containing terminal hydroxides were triflated to be transformed into highly Lewis acidic heterogeneous catalysts. Multifunctional groups can also be installed in such Lewis acidic MOF catalysts for tandem reactions. More particularly, the aluminum-based MOF catalyst, AlOTf-Pd, containing both strong Lewis acidic Al-OTf sites and hydrogenation catalyst Pd nanoparticles were prepared as shown in FIG. 1. m-DUT-5 MOF (DUT=Dresden University of Technology) was first synthesized through solvothermal reaction between aluminum salts and a mixture of 2,2'-bipyridine-5,5'-dicarboxylic acid (dcbpy) and 1,4-benzenediacrylic acid.[34] The 1,4-benzenediacrylic acid ligand (20% in the MOF ligands) was then post-synthetically cleaved by ozonolysis to create terminal Al-OH/OH$_2$ sites within the MOF frameworks.[35] The terminal Al-OH/OH$_2$ sites were further activated by $(CH_3)_3SiOTf$ to generate highly Lewis acidic AlOTf sites by replacing the terminal hydroxides/waters with strongly electron-withdrawing OTf$^-$ groups. The resultant AlOTf-bpy MOF was further metalated on the bipyridine sites by $PdCl_2(CH_3CN)_2$ to generate AlOTf-bpy-Pd as the pre-catalyst, which was reduced in situ by the H$_2$ atmosphere during the catalytic reaction conditions to give the true catalytic active species AlOTf-Pd with entrapped Pd nanoparticles.

Biomass hydrodeoxygenation allows the conversion of biomass to feedstock molecules with lower oxygen content that have more desirable properties for many applications. Several multifunctional catalyst systems featuring both acidic sites for C—O bond cleavage and hydrogenation sites to generate saturated alkanes have been studied for catalytic biomass hydrodeoxygenation.[36-39] AlOTf-Pd displayed outstanding catalytic activity in tandem ether/alcohol C—O bond cleavage reactions to transform O-containing compounds into saturated alkane. At as low as 0.2 mol % loading (w.r.t. Lewis acidic sites), AlOTf-Pd efficiently catalyzed the C—O bond cleavage of 1,8-cineole to menthane quantitively after 24 h reaction under 50 bar of H$_2$ and 100° C. Highest TON was achieved when the catalyst loading was lowered to 0.1 mol %, with a total TON of 800. This catalyst significantly outperformed the homogeneous analogues. Moreover, compared to the reported homogeneous metal triflate+supported Pd catalyst system[37], AlOTf-Pd avoided the use of expensive Lewis acidic metal salts (e.g., Hf, Sc, Yb, etc). A wide scope of ethers and alcohols were tested as substrates under similar reaction conditions in the presence of AlOTf-Pd, with a reactivity trend found among tertiary, secondary, and primary substrates. See Table 1. For tertiary alcohols or ethers, e.g., 1,8-cineole and 1-methylcyclohexanol, the tandem C—O bond cleavage proceeded smoothly at temperature as low as 100° C. Higher temperatures, typically 150° C., were used for secondary alcohols or ethers to afford good conversions, while even higher temperatures (up to 200° C.) were used with primary alcohols (e.g., 1-heptanol). Notably, substrates with more active β-H, e.g. phenethoxybenzene and (2-methoxyethyl)benzene, tend to undergo C—O bond cleavage at milder conditions, producing ethylbenzene as the main product.

Scheme 1. Exemplary Tandem Ether/Alcohol C—O Bond Cleavage Catalyzed by AlOTf—Pd.

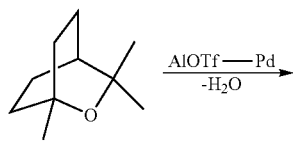

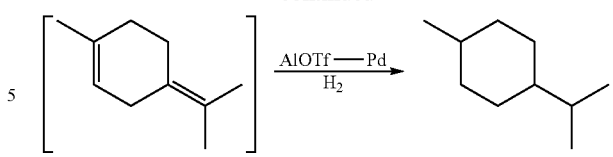

As shown in Scheme 1, above, in a nitrogen-filled glovebox, AlOTf-bpy-Pd (2.0 mg, 1.2 μmol AlOTf sites), 1,8-cineole (100 μL, 0.6 mmol), and 1.0 mL of 1,2-dichloroethane were transferred into a Parr reactor. The Parr reactor was then sealed under nitrogen, purged with hydrogen several times and charged with hydrogen to 50 bar. After stirring at 100° C. for 24 hours, the pressure was released and the MOF catalyst was removed from the reaction mixture via centrifugation. The supernatant was analyzed by GC-MS to give menthane (a mixture of cis/trans isomers) in >99% yield with 100% of substrate conversion.

TABLE 1

Substrate Scope of AlOTf-Pd Catalyzed Tandem Etheric/Alcohol C—O Bond Cleavage[a]

| Substrate | Catalyst Loading | Reaction Temperature/ Reaction Time | Product | Conversion (Yield) |
|---|---|---|---|---|
| 1-methylcyclohexanol | 0.1 mol % | 100° C./24 h | isopropylcyclohexane | 100% (>99%) |
| 1,8-cineole | 0.2 mol % / 0.1 mol % | 100° C./24 h / 100° C./24 h | 4-isopropyl-1-methylcyclohexane | 100% (>99%) / 80% (80%) |
| cyclohexanol | 0.1 mol % | 150° C./24 h | cyclohexane | 100% (>99%) |
| 2-octanol | 0.2 mol % | 150° C./24 h | octane | 100% (>99%) |
| 1-heptanol | 0.5 mol % | 200° C./24 h | heptane | 100% (92%) |
| phenethoxybenzene | 0.2 mol % / 0.2 mol % | 150° C./4 h / 150° C./24 h | ethylbenzene | 65% (64%)[b] / 100% (89%)[b] |
| (2-methoxyethyl)benzene | 0.2 mol % | 130° C./24 h | ethylbenzene | 70% (61%)[b] |

[a]Unless noted, all reactions performed with indicated amount of AlOTf-bpy-Pd, 0.6 mmol of substrate, 50 bar $H_2$, in 1.0 mL of 1,2-dichloroethane. Conversion and yield determined by GC-MS integral with mesitylene as the internal standard.
[b]Reaction performed in 1 bar $H_2$.

AlOTf-Pd is a highly active catalytic system for tandem ester C—O bond cleavage under certain reaction conditions, with similar reactivity trends (tertiary>secondary >primary) observed. See Table 2, below. Tertiary ester terpinyl acetate was efficiently cleaved to produce manthane with a TON of 440 at 100° C., while the C—O cleavage of secondary ester L-menthyl acetate required 150° C. and 0.5 mol % of catalyst to proceed. For primary octyl acetate, an even higher reaction temperature of 200° C. was used. Similarly, substrate with active β-H, e.g., phenethyl acetate, is easier to undergo C—O cleavage. Moreover, lactones (e.g., 5-hexanolide) can also go through tandem C—O cleavage to generate saturated carboxylate acids in good yields.

Scheme 2. AlOTf——Pd Catalyed Tandem Ester C—O Bond Cleavage.

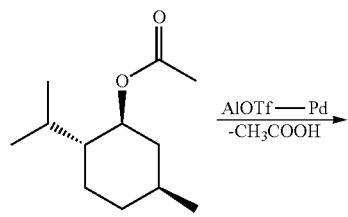

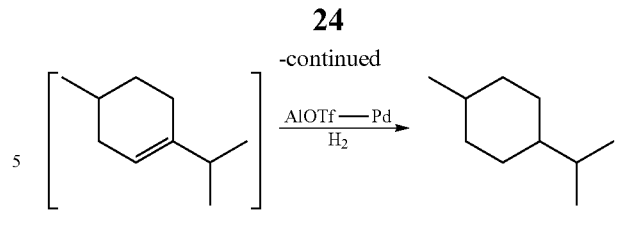

As shown in Scheme 2, above, in a nitrogen-filled glovebox, AlOTf-bpy-Pd (5.0 mg, 1.2 μmol AlOTf sites), L-menthyl acetate (129 μL, 0.6 mmol), and 1.0 mL of 1,2-dichloroethane were transferred into a Parr reactor. The Parr reactor was then sealed under nitrogen, purged with hydrogen several times and charged with hydrogen to 50 bar. After stirring at 150° C. for 24 hours, the pressure was released and the MOF catalyst was removed from the reaction mixture via centrifugation. The supernatant was analyzed by GC-MS to give menthane (a mixture of cis/trans isomers) in >99% yield with 100% of substrate conversion.

TABLE 2

Substrate Scope of AlOTf-Pd Catalyzed Ester C—O Bond Cleavage[a]

| Substrate | Catalyst Loading | Reaction Temperature/ Reaction Time | Product | Conversion (Yield) |
|---|---|---|---|---|
| terpinyl acetate | 0.2 mol % | 100° C./48 h | menthane | 93% (88%) |
| L-menthyl acetate | 0.5 mol %<br>0.1 mol % | 150° C./24 h<br>150° C./24 h | menthane | 100% (>99%)<br>45% (45%) |
| isopinocampheyl acetate | 0.5 mol % | 150° C./24 h | pinane | 84% (78%) |
| cyclohexyl acetate | 0.2 mol %<br>0.2 mol % | 150° C./24 h<br>170° C./24 h | cyclohexane | 58% (53%)<br>88% (66%) |
| cyclohexyl propanoate | 0.2 mol % | 170° C./24 h | cyclohexane | Ongoing |

TABLE 2-continued

Substrate Scope of AlOTf-Pd Catalyzed Ester C—O Bond Cleavage[a]

| Substrate | Catalyst Loading | Reaction Temperature/ Reaction Time | Product | Conversion (Yield) |
|---|---|---|---|---|
| (n-hexyl acetate) | 0.5 mol % | 200° C./24 h | (n-heptane) | 100% (79%) |
| (2-phenylethyl acetate) | 0.2 mol % | 130° C./6 h | (ethylbenzene) | 100% (94%)[b] |
| (δ-valerolactone, methyl) | 0.2 mol % | 130° C./24 h | (5-hydroxyhexanoic acid) | 100% (61%) |

[a]Unless noted, all reactions performed with indicated amount of AlOTf-bpy-Pd, 0.6 mmol of substrate, 50 bar $H_2$, in 1.0 mL of 1,2-dichloroethane. Conversion and yield determined by GC-MS integral with mesitylene as the internal standard.
[b]Reaction performed in 1 bar $H_2$.

Example 2

Synthesis and Characterization of ZrOTf-BTC

Materials and Methods: All of the reactions and manipulations were carried out under ambient atmosphere unless otherwise indicated. Tetrahydrofuran (THF) and toluene were purified by passing through a neutral alumina column under nitrogen gas ($N_2$). The substrates for catalytic reactions, including dienes, dienophiles, epoxides, anilines, alkenyl alcohols, imines and diazo compounds were purchased from Sigma-Aldrich (St. Louis, Missouri, United States of America) or Thermo Fisher Scientific (Waltham, Massachusetts, United States of America) and used as received. Powder X-ray diffraction (PXRD) data were collected on a Bruker D8 Venture diffractometer (Bruker Corporation, Billerica, Massachusetts, United States of America) using a Cu Kα radiation source (I=1.54178 Å). $N_2$ sorption experiments were performed on a Micromeritics TriStar II3020 instrument (Micromeritics Instruments Corporation, Norcross, Georgia, United States of America). Thermogravimetric analysis (TGA) was performed in air using a Shimadzu TGA-50 (Shimadzu Corporation, Kyoto, Japan) equipped with a platinum pan and heated at a rate of 1.5° C. per min up to 800° C. Electron paramagnetic resonance (EPR) spectra were collected with a Bruker Elexsys 500 X-band EPR spectrometer (Bruker Corporation, Billerica, Massachusetts, United States of America) at 100 K. Fluorescence data were measured using an RF-5301PC spectrofluorophotometer (Shimadzu Corporation, Kyoto, Japan). ICP-MS data were obtained with an Agilent 7700x ICP-MS (Agilent Technologies, Santa Clara, California, United States of America) and analyzed using an ICP-MS MassHunter version B01.03. Samples were diluted in a 2% $HNO_3$ matrix and analyzed with a $^{159}$Tb internal standard against a 12-point standard curve over a range from 0.1 parts-per-billion (ppb) to 500 ppb. The correlation was >0.9997 for all analyses of interest. Data collection was performed in Spectrum Mode with five replicates per sample and 100 sweeps per replicate.

$^1$H NMR spectra were recorded on a Bruker NMR 500 DRX spectrometer (Bruker Corporation, Billerica, Massachusetts, United States of America) at 500 MHz, and referenced against the proton resonance resulting from incomplete deuteration of $CDCl_3$ (δ 7.26) or benzene-$d_6$ (δ 7.16). The following abbreviations are used: s: singlet, d: doublet, t: triplet, q: quartet, m: multiplet, br: broad, app: apparent. High-resolution mass spectra were obtained using an Agilent 6224 Accurate-Mass time-of-flight (TOF) spectrometer (Agilent Technologies, Santa Clara, California, United States of America).

Synthesis of ZrOTf-BTC: ZrOH-BTC was synthesized from Zr-BTC (formate capped) by $HCl/H_2O$ activation as reported previously.[40] In a $N_2$-filled glove box, ZrOH-BTC (6.4 mmol of Zr) was weighed out in a 75 mL glass vessle and dispersed in 40 mL of toluene. Trimethylsilyl trifluoromethanesulfonate ($Me_3SiOTf$, 11.6 mL, 64 mmol) was then added to the suspension. The vessel was sealed with a Teflon cap and kept at 80° C. After 6 h, the suspension was cooled to room temperature, transferred into a glove box, and washed with dry toluene 5 times. The MOF was then Sohxlet extracted with hexane to remove the trapped HOTf species inside the MOF channel. 10 equivalents of $LiCH_2SiMe_3$ was added to the round-bottom receiving flask to quench extracted HOTf during Sohxlet extraction. After solvent exchange with dry benzene, ZrOTf-BTC was freeze-dried under vacuum overnight and stored inside the glovebox for further use.

Thermogravimetric analysis of ZrOTf-BTC: ZrOTf-BTC started to decompose at 220° C. in air. The weight loss in the 220-800° C. range is 63.8% based on TGA analysis. This weight loss is consistent with the formula change from $Zr_6O_4(OH)_4(BTC)_2(OTf)_6$ to $(ZrO_2)_{12}$ with an expected weight loss of 62.8%.

Quantification of $(Me_3Si)_2O$ Byproduct: After treating ZrOH-BTC with $Me_3SiOTf$ for 6 h, the reaction mixture was transferred into a $N_2$-filled glove box. 4.0 equiv. of mesitylene (with respect to (w.r.t.) Zr) was added to the mixture as internal standard. 200 μL of supernatant was diluted with 0.6 mL of benzene-$d_6$, then analyzed by $^1$H NMR. The chemical shifts of authentic $(Me_3Si)_2O$, $Me_3SiOTf$, and mesitylene $CH_3$ groups are δ=0.12, −0.04, and 2.16 ppm, respectively. The amount of $(Me_3Si)_{20}$ was determined to be 1.92 equiv. w.r.t. Zr, matching well with the expected value of 2.0 equiv.

Quantification of MOF Lewis Acidity via EPR of MOF-bound Superoxide Speices: Dimeric 1-benzyl-1,4-dihydronicotinamide [$(BNA)_2$] was synthesized using the literature procedure.[41] Superoxide radical anions were generated in situ through the photoreduction of oxygen by $(BNA)_2$ in an oxygen-saturated MeCN/toluene mixture solvent. In a typical experiment, 20% MeCN in toluene was used as a mixed solvent to dissolve $(BNA)_2$ in 4 mM concentration (17 mg in 10 mL). After brief sonication, the $(BNA)_2$ solution was bubbled with oxygen for 5 min to saturation. Afterwards, ZrOH-BTC or ZrOTf-BTC (20 μmol of Zr) was dispersed in 1.0 mL of the $O_2/(BNA)_2$ solution via sonication. The mixture was then transferred into an EPR tube for EPR analysis. EPR spectra were recorded on a Bruker Elexsys 500 X-band EPR spectrometer (Bruker Corporation, Billerica, Massachusetts, United States of America) under irradiation of a white-light lamp (Fiber-Lite MI-150) by focusing the lamp on the sample cell in the ESR cavity at 100 K. The sample was loaded into the cavity and held for 10 minutes to ensure superoxide generation and coordination to the MOF and the freezing of the dispersion. The EPR spectrum was collected at 9.63 GHz.

For ZrOTf-BTC, the coordinated superoxide showed a typical anisotropic signal with $g_{zz}$=2.0310, $g_{yy}$=2.009 and $g_{xx}$=2.002. The superoxide binding energy to Zr centers can be calculated using the following equation adopted from literature reports to be 0.98 eV.[42-43]

$$g_{zz} = g_e + 2\sqrt{\frac{\lambda^2}{\lambda^2 + \Delta E^2}}$$

where the free spin value $g_e$=2.0023, λ is the spin-orbit coupling constant of oxygen that is known to be 0.014 eV, and ΔE is the energy splitting of $\pi_g$ levels due to superoxide coordination to Zr.

Quantification of Lewis Acid Acidity by N-methylacridone Fluorescence: The fluorescent indicator N-methylacridone (NMA) was purchased from Sigma-Aldrich (St. Louis, Missouri, United States of America). The fluorescence measurement was performed using a Shimadzu RF-5301PC spectrofluorophotometer (Shimadzu Corporation, Kyoto, Japan) with excitation wavelength of 413 nm. NMA was dissolved in MeCN to form an NMA solution with a concentration of 10 μM to give a reference emission wavelength that was measured to be 433 nm.

For the measurement of MOF Lewis acidity, 0.8 mmol of ZrOH-BTC or ZrOTf-BTC (by amount of Zr) was added to a 2 dram vial in an $N_2$-filled glovebox. 4 mL of NMA solution (10 μM in MeCN) was then added to the vial. The resulting mixture was sonicated for 2 min until the MOF was well suspended, and then the suspension was transferred to a fluorescence cuvette for measurement using an excitation wavelength of 413 nm. The emission maxima for NMA-bound ZrOH-BTC and ZrOTf-BTC were measured to be 466 nm and 472 nm, respectively.

Example 3

Synthesis of ZrOTf-BTC@$SiO_2$ Composite as a Continuous Flow Catalyst

Scheme 3. Synthesis of Zr—BTC@$SiO_2$.

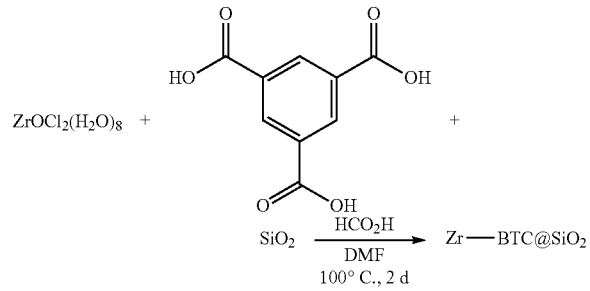

Figure 2:
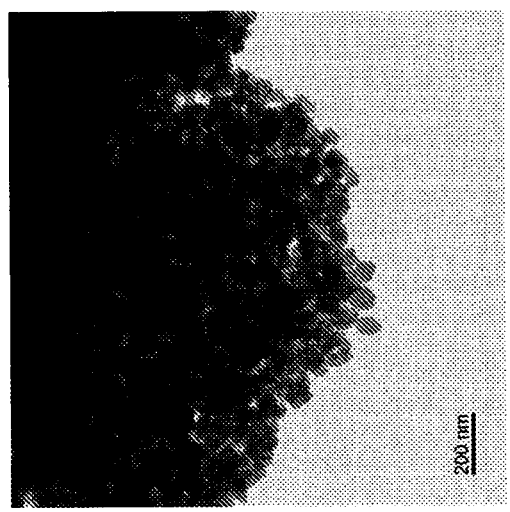
FIG. 2 is a transmission electron microscopy (TEM) image of zirconium-trimesic acid (Zr-BTC) metal-organic framework (MOF)/silica (Zr-BTC@$SiO_2$) composite particles showing the core-shell structure of the Zr-BTC MOF octahedral particles coating the surface of the silica.

As shown above in Scheme 3, $ZrOCl_2(H_2O)_8$ (1.61 g, 5.0 mmol) and trimesic acid ($H_3$BTC, 1.10 g, 5.25 mmol) were dissolved in DMF (50 mL) and $H_2O$ (50 mL), and then mixed with $SiO_2$ (6.0 g, 20 equiv.) in a 250 mL round-bottom flask. The mixture was heated to 100° C. on an oil bath for 2 days to afford Zr-BTC@$SiO_2$ as a white solid. The material was centrifuged out of suspension and then washed with DMF, THF, and benzene three times each to remove residual precursors and solvents before freeze-drying under vacuum. A SEM image of the Zr-BTC@$SiO_2$ is shown in FIG. 2.

Scheme 4. Synthesis for ZrOH—BTC@$SiO_2$ Composite.

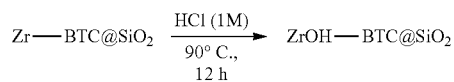

As shown in Scheme 4, above, Zr-BTC@$SiO_2$ (6.2 g) was suspended in 400 mL of HCl (1 M in $H_2O$) and heated in a 90° C. oven for 12 h. The mixture was centrifuged and sequentially washed with deionized $H_2O$, acetone, and THF three times each, and then freeze-dried in benzene to yield ZrOH-BTC@$SiO_2$ as a white powder (6.1 g). To ensure the successful activation of formate group, a small amount of the material was digested to quantify the amount of formate. $^1$H NMR analysis detected only 0.18 equiv. of $HCO_2H$ w.r.t. BTC, corresponding to only 0.06 $HCO_2^-$ per Zr center. $^1$H NMR of digested Zr-BTC@$SiO_2$ showed a formate: BTC ratio of 1:0.06 in the composite, indicating 94% removal of capping formats.

To quantify the ratio of MOF to $SiO_2$ in ZrOH-BTC@$SiO_2$, 5 μmol of mesitylene standard was added to 5 mg of the composite. The material was digested with $D_3PO_4$/DMSO-$d_6$ (0.3 mL/0.5 mL) and analyzed by $^1$H NMR. In three repetitive runs, 0.066±0.006 μmol of BTC was detected per 5 mg of composite material, corresponding to 0.20 μmol of Zr centers per 5.0 mg of ZrOH-BTC@$SiO_2$.

Scheme 5. Synthesis of ZrOTf—BTC@$SiO_2$ Catalyst.

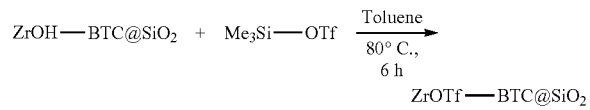

Figure 3:
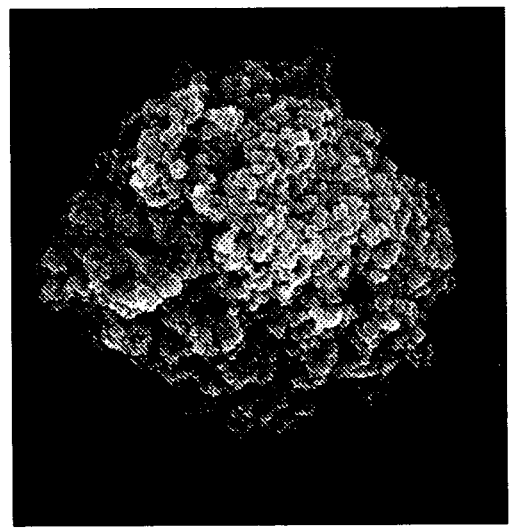
FIG. 3 is a scanning electron microscopy (SEM) image of a zirconium triflate-trimesic acid (ZrOTf-BTC) metal-organic framework (MOF)/silica (ZrOTf-BTC@$SiO_2$) composite particle, which shows the surface of silica coated with ZrOTf-BTC MOF particles that are approximated 50 nanometers (nm) in diameter.

As shown in Scheme 5, above, in a N$_2$-filled glove box, 2.5 g of ZrOH-BTC (0.1 mmol of Zr) was weighed out in a 75 mL glass vessel and dispersed in 40 mL of toluene. Trimethylsilyl trifluoromethanesulfonate (Me$_3$SiOTf, 906 µL, 5.0 mmol) was then added to the suspension. The vessel was sealed with Teflon cap and kept at 80° C. for 6 h before cooling to room temperature and washing with dry toluene for 5 times. After solvent exchange with dry benzene, ZrOTf-BTC@SiO$_2$ was freeze-dried under vacuum overnight and stored inside the glovebox for further use. PXRD patterns of ZrOTf-BTC@SiO$_2$, ZrOH-BTC@SiO$_2$, and Zr-BTC@SiO$_2$ are very similar to each other, indicating that the crystallinity of the material is maintained through the Me$_3$SiOTf treatment. The SEM image of a ZrOTf-BTC@SiO$_2$ particle, which shows the surface of silica coated with MOF particles that are ~50 nm in dimensions is shown in FIG. 3.

Packing of ZrOTf-BTC@SiO$_2$ into a stainless-steel column: The column for packing MOF@SiO$_2$ catalyst was purchased from Sigma-Aldrich (St. Louis, Missouri, United States of America). In a typical procedure, 1.25 g of ZrOTf-BTC@SiO$_2$ composite was slurry-packed between two metal filter plates in a stainless-steel tubing (ID 4.16 mm, length 15 cm, Sigma-Aldrich). ZrOTf-BTC@SiO$_2$ was dispersed in CH$_2$Cl$_2$, transferred into the one-end sealed tubing, then pressurized with N$_2$ to compact the composite and remove the trapped air bubbles. This transfer-compress process was repeated until the tubing was filled-up with the composite material. The end of the tube was then sealed and the column was stored for flow catalysis.

Example 4

ZrOTf-BTC(SiO$_2$ Catalyzed Diels-Alder Reactions in Batch Mode

Scheme 6. Exemplary ZrOTf—BTC Catalyzed Diels-Alder Reaction.

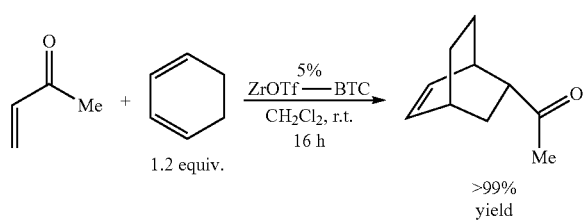

A typical procedure of ZrOTf-BTC catalyzed Diels-Alder reactions in batch mode is shown in Scheme 6, above. Under ambient atmosphere, but-3-en-2-one (81 µL, 1.0 mmol), cyclohexadiene (120 µL, 1.2 mmol), ZrOTf-BTC (50 µmol Zr), and CH$_2$Cl$_2$ (4.0 mL) was charged to a 2-dram vial. The reaction mixture was stirred at room temperature for 16 h, then the MOF catalyst was removed by centrifugation. The supernatant was evaporated on a rotavap to give the crude product bicyclo[2.2.2]oct-5-en-2-ylethanone in a quantitative yield (>99%, mesitylene added as internal standard). The residue was further purified by silica gel chromatography eluting with hexane/CH$_2$Cl$_2$ to afford the target molecule as a colorless oil (90% of isolated yield). The MOF crystallinity was maintained after the reaction run, and minimum metal leaching with 0.13% of Zr per run was detected by ICP-MS analysis. PXRD patterns showed retention of ZrOTf-BTC crystallinity after Diels-Alder reactions (when compared to PXRD of freshly prepared ZrOTf-BTC and simulated MOF-808 pattern).

Products prepared by ZrOTf-BTC catalyzed Diels-Alder reaction:

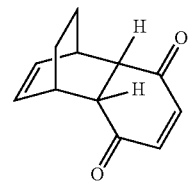

endo-tricyclo[6.2.2.0$^{2,7}$]dodeca-4,9-diene-3,6-dione. (CAS: 76035-69-3)$^1$H NMR (500 MHz, Chloroform-d) δ 6.64 (s, 2H), 6.21 (dd, J=4.5, 3.1 Hz, 2H), 3.21 (dq, J=4.6, 1.6 Hz, 2H), 2.98 (t, J=1.2 Hz, 2H), 1.70 (dt, J=8.8, 1.5 Hz, 2H), 1.40-1.34 (m, 2H). $^{13}$C NMR (126 MHz, Chloroform-d) δ 199.40, 142.02, 133.50, 49.37, 35.38, 24.77. HR-MS (ESI, positive mode): m/z calc'd for C$_{12}$H$_{13}$O$_2$ [M+H]$^+$10: 189.0916, found 189.0913.

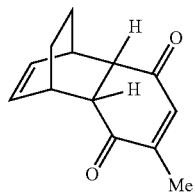

endo-4-methyl-tricyclo[6.2.2.0$^{2,7}$]dodeca-4,9-diene-3,6-dione. (CAS: 93139-46-9)$^1$H NMR (500 MHz, Chloroform-d) δ 6.53 (q, J=1.5 Hz, 1H), 6.22-6.12 (m, 2H), 3.20-3.15 (m, 2H), 2.98-2.92 (m, 2H), 1.92 (d, J=1.4 Hz, 3H), 1.70 15-1.66 (m, 2H), 1.38-1.30 (m, 2H). $^{13}$C NMR (126 MHz, Chloroform-d) δ 199.70, 199.03, 151.61, 139.61, 133.64, 133.14, 49.89, 49.24, 35.56, 35.31, 24.77, 24.72, 16.67. HR-MS (APCI, positive mode): m/z calc'd for C$_{13}$H$_{15}$O$_2$ [M+H]$^+$: 203.1072, found 203.1071.

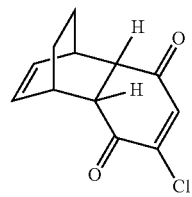

endo-4-chloro-tricyclo[6.2.2.0$^{2,7}$]dodeca-4,9-diene-3,6-dione. $^1$H NMR (500 MHz, Chloroform-d) δ 6.95 (s, 1H), 6.24 (dq, J=8.2, 6.4 Hz, 2H), 3.24 (ddt, J=19.7, 5.3, 2.6 Hz, 2H), 3.08 (ddd, J=36.7, 9.2, 2.6 Hz, 2H), 1.81-1.65 (m, 2H), 1.39 (tq, J=10.0, 3.2 Hz, 2H). $^{13}$C NMR (126 MHz, Chloroform-d) δ 196.60, 191.76, 149.61, 139.96, 133.86, 133.16, 50.19, 49.23, 35.99, 35.52, 24.74, 24.59. HR-MS (APCI, positive mode): m/z calc'd for C$_{12}$H$_{12}$O$_2$Cl [M+H]$^+$: 223.0526, found 223.0521.

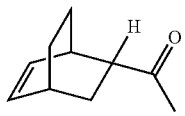

1-bicyclo[2.2.2]oct-5-en-2-yl-ethanone. (CAS: 93139-46-9) $^1$H NMR (500 MHz, Chloroform-d) δ 6.27 (ddd, J=8.1, 6.6, 1.3 Hz, 1H), 6.10 (ddd, J=8.0, 6.4, 1.3 Hz, 1H), 2.89 (ddtd, J=6.6, 3.4, 2.3, 1.3 Hz, 1H), 2.66 (ddd, J=8.8, 6.5, 2.2 Hz, 1H), 2.60 (dtt, J=5.6, 4.2, 3.0 Hz, 1H), 2.11 (s, 3H), 1.65 (ddt, J=7.9, 2.6, 1.4 Hz, 2H), 1.60 (ddt, J=14.1, 9.3, 2.7 Hz, 1H), 1.50 (dddd, J=12.5, 10.2, 3.8, 2.3 Hz, 1H), 1.32 (tt, J=11.5, 3.5 Hz, 1H), 1.28-1.23 (m, 1H). $^{13}$C NMR (126 MHz, Chloroform-d) δ 209.88, 135.21, 131.05, 51.56, 32.09, 29.56, 28.65, 28.34, 25.87, 24.52. HR-MS (APCI, positive mode): m/z calc'd for $C_{10}H_{15}O$ [M+H]$^+$: 151.1123, found 151.1121.

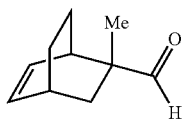 [SMILES: CC1(C=O)CC2C=CC1CC2]

2-formyl-2-methyl-bicyclo(2.2.2)octen-(5). (CAS: 60838-99-5) $^1$H NMR (500 MHz, Chloroform-d) δ 9.32 (s, 1H), 6.32-6.19 (m, 2H), 2.60 (dp, J=5.8, 2.2, 1.6 Hz, 1H), 2.48 (dq, J=5.4, 2.6 Hz, 1H), 2.01 (dt, J=12.9, 3.3 Hz, 1H), 1.90 (ddt, J=13.0, 10.1, 2.9 Hz, 1H), 1.53 (dddd, J=11.5, 9.1, 4.5, 2.2 Hz, 1H), 1.32-1.19 (m, 3H), 1.15 (s, 3H). $^{13}$C NMR (126 MHz, Chloroform-d) δ 205.71, 135.14, 133.55, 49.97, 36.08, 35.55, 30.53, 25.09, 21.22, 20.20. HR-MS (APCI, positive mode): m/z calc'd for $C_{10}H_{15}O$ [M+H]$^+$:151.1123, found 151.1118.

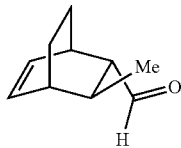 [SMILES: CC1C2C=CC(CC2)C1C=O]

endo-trans-3-methylbicyclo(2.2.2)oct-5-ene-2-carbaldehyde. (CAS: 2958-78-3) $^1$H NMR (500 MHz, Chloroform-d) δ 9.41 (d, J=2.0 Hz, 1H), 6.44 (ddd, J=8.1, 6.7, 1.3 Hz, 1H), 6.10 (ddd, J=7.9, 6.3, 1.2 Hz, 1H), 2.83 (ddt, J=4.4, 2.9, 1.7 Hz, 1H), 2.33 (ddd, J=6.8, 3.3, 1.1 Hz, 1H), 1.94 (dt, J=6.1, 2.0 Hz, 1H), 1.91-1.84 (m, 1H), 1.84-1.76 (m, 1H), 1.55 (tdd, J=9.8, 4.4, 2.6 Hz, 1H), 1.38-1.29 (m, 1H), 1.14 (dddt, J=10.1, 4.4, 3.0, 1.5 Hz, 1H), 1.10 (d, J=6.9 Hz, 3H). $^{13}$C NMR (126 MHz, Chloroform-d) δ 203.79, 137.78, 130.22, 59.73, 35.60, 32.29, 31.35, 25.64, 19.67, 18.42. HR-MS (APCI, positive mode): m/z calc'd for $C_{10}H_{15}O$ [M+H]$^+$: 151.1123, found 151.1119.

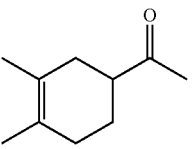

1-(3,4-dimethylcyclohex-3-enyl)ethanone. (CAS: 41723-54-0) $^1$H NMR (500 MHz, Chloroform-d) δ 2.60-2.50 (m, 1H), 2.16 (s, 3H), 2.13-2.08 (m, 1H), 2.06-1.97 (m, 3H), 1.93 (m, 1H), 1.63 (s, 3H), 1.60 (s, 3H), 1.57-1.46 (m, 1H). $^{13}$C NMR (126 MHz, Chloroform-d) δ 212.08, 125.56, 124.10, 48.44, 33.24, 31.38, 28.12, 25.47, 19.18, 18.97. HR-MS (APCI, positive mode): m/z calc'd for $C_{10}H_{15}O$ [M+H]$^+$:153.1279, found 153.1277.

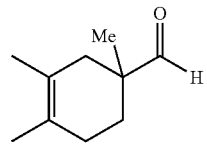

1,3,4-trimethyl-3-cyclohexene-1-carboxaldehyde. (CAS: 40702-26-9) $^1$H NMR (500 MHz, Chloroform-d) δ 9.45 (s, 1H), 2.28-2.21 (m, 1H), 2.02-1.91 (m, 2H), 1.84-1.79 (m, 1H), 1.78-1.73 (m, 1H), 1.64 (dq, J=1.9, 1.0 Hz, 3H), 1.59 (dq, J=1.9, 0.9 Hz, 3H), 1.46 (dt, J=13.6, 7.0 Hz, 1H), 1.02 (s, 3H). $^{13}$C NMR (126 MHz, Chloroform-d) δ 206.40, 125.26, 123.17, 45.42, 38.01, 29.39, 28.59, 20.88, 19.36, 18.95. HR-MS (APCI, positive mode): m/z calc'd for $C_{10}H_{15}O$ [M+H]$^+$:153.1279, found 153.1275.

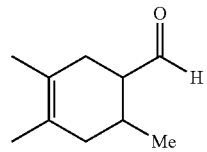

3,4,6-trimethyl-3-cyclohexene-1-carbaldehyde. (CAS: 13702-58-4) $^1$H NMR (500 MHz, Chloroform-d) δ 9.61 (d, J=3.2 Hz, 1H), 2.20-2.16 (m, 2H), 2.03-1.98 (m, 3H), 1.69-1.66 (m, 1H), 1.67-1.62 (m, 3H), 1.62-1.59 (m, 3H), 1.00 (d, J=6.5 Hz, 3H). $^{13}$C NMR (126 MHz, Chloroform-d) δ 205.54, 125.27, 122.75, 53.68, 39.06, 30.49, 28.94, 19.73, 19.03, 18.83. HR-MS (APCI, positive mode): m/z calc'd for $C_{10}H_{15}O$ [M+H]$^+$:153.1279, found 153.1272.

A "hot Filtration" test was performed to rule out the possibility of leached lewis acidic metal species or soluable Bronsted acidic species contributing to the Diels-Alder reaction reactivity. More particularly, 1.0 mol % of ZrOTf-BTC was first used to catalyze Diels-Alder reaction between cyclohexa-1,3-diene and 1,4-benzoquinone to give endo-tricyclo[6.2.2.0$^{2,7}$]dodeca-4,9-diene-3,6-dione in 96% of yield in 2 hours. Then, the MOF and supernatant were separated via centrifugation and used as catalysts, respectively, for the Diels-Alder reaction between cyclohexa-1,3-diene and 3-buten-2-one without further treatment. The recovered ZrOTf-BTC catalyst afforded 1-bicyclo[2.2.2]oct-5-en-2-yl-ethanone in 81% yield in 2 hours, while no desired cyclolation product was detected in the reaction catalyzed by the supernatant. This result excludes the possibility of leached Zr species or soluble Bronsted acids contributing to the catalytic reactivity.

Example 5

ZrOTf-BTC Catalyzed Diels-Alder Reactions in Flow Mode

A peristaltic pump (sold under the tradename MASTER-FLEX™, Cole-Parmer Instrument Company, Vernon Hills, Illinois, United States of America) was used to deliver the solution of reaction substrates to the column reactor. The substrate solution sequentially flowed through the substrate stock bottle, pump head, a short guard column (silica), and then the column reactor. The product solution was received in a glass bottle. The concentration and the flow rate of the substrate solution were optimized to maximize the turnover number. The yield of the reaction product was monitored periodically with $^1$H NMR using the mesitylene as internal standard.

Scheme 7. Exemplary ZrOTf—BTC Catalyzed Diels-Alder Reaction in Flow Mode.

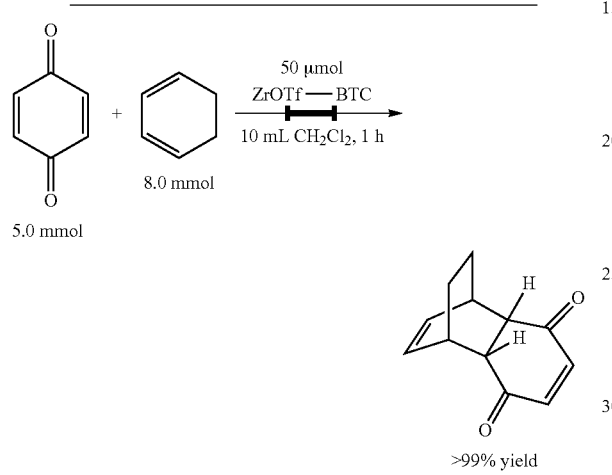

>99% yield

As shown in Scheme 7, above, for a one-hour flow catalysis of Diels-Alder reaction, a mixture of 1,4-benzoquinone (540 mg, 5.0 mmol) and cyclohexa-1,3-diene (800 µL, 8.0 mmol) was dissolved in $CH_2Cl_2$ (8.0 mL), and flowed through the ZrOTf-BTC@SiO$_2$ column at a rate of 10 mL·h$^{-1}$ at room temperature. After the flow, 2 mL of $CH_2Cl_2$ was used to wash the column to recover the remaining product. The collected solution was evaporated under rotovap to remove the solvent and excess cyclohexa-1,3-diene to obtain the cycloaddition product as an off-white solid in a quantitative yield.

Example 6

ZrOTf-BTC Catalyzed Epoxide Ring-Opening Reactions in Batch Mode

Scheme 8. Exemplary Epoxide Ring-Opening Catalyzed by ZrOTf—BRC.

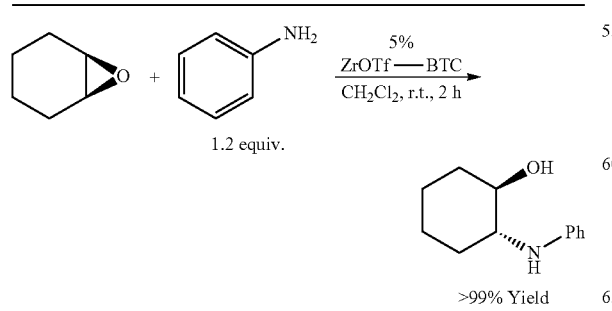

>99% Yield

A typical procedure of ZrOTf-BTC catalyzed epoxide ring opening reactions in batch mode is shown in Scheme 8, above. Under ambient atmosphere, cyclohexene oxide (100 µL, 1.0 mmol), mainline (110 µL, 1.2 mmol), ZrOTf-BTC (50 µmol Zr), and $CH_2Cl_2$ (4.0 mL) were charged to a 2-dram vial. The reaction mixture was stirred at room temperature for 2 h, then the MOF catalyst was removed by centrifugation. The supernatant was evaporated on a rotavap to give the crude product 2-(phenylamino)cyclohexan-1-ol in a quantitative yield (>99%, mesitylene added as internal standard). The residue was further purified by silica gel chromatography eluting with hexane/$CH_2Cl_2$ to afford the target molecule as a colorless oil (86% of isolated yield). The MOF crystallinity was maintained after the reaction run and minimum metal leaching with 0.14% of Zr per run was detected by ICP-MS analysis. PXRD patterns showed retention of ZrOTf-BTC crystallinity after epoxide ring-opening reactions (when compared to PXRD of freshly prepared ZrOTf-BTC and simulated MOF-808 pattern).

Products prepared by ZrOTf-BTC catalyzed epoxide ring-opening reactions:

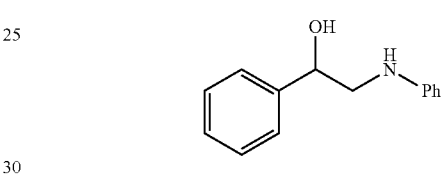

1-phenyl-2-phenylaminoethanol. (CAS: 99342-73-1)$^1$H NMR (500 MHz, Chloroform-d) δ 7.40-7.33 (m, 4H), 7.30-7.25 (m, 1H), 7.14-7.09 (m, 2H), 6.69 (tt, J=7.3, 1.2 Hz, 1H), 6.61-6.56 (m, 2H), 4.52 (dd, J=7.0, 4.2 Hz, 1H), 3.95 (dd, J=11.1, 4.2 Hz, 1H), 3.76 (dd, J=11.2, 7.0 Hz, 1H), 1.79 (br, 1H). $^{13}$C NMR (126 MHz, Chloroform-d) δ 147.24, 140.12, 129.19, 128.87, 127.65, 126.75, 117.91, 113.87, 67.40, 59.86. HR-MS (APCI, positive mode): m/z calc'd for $C_{14}H_{16}NO$ [M+H]$^+$:214.1232, found 214.1225.

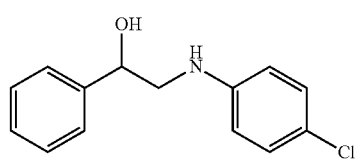 [SMILES: OC(CNc1ccc(Cl)cc1)c1ccccc1]

2-((4-chlorophenyl)amino)-1-phenylethan-1-ol. (CAS: 91851-16-0)$^1$H NMR (500 MHz, Chloroform-d) δ 7.42-7.32 (m, 4H), 7.31-7.27 (m, 1H), 7.03 (dd, J=9.1, 2.6 Hz, 2H), 6.47 (dd, J=9.1, 2.7 Hz, 2H), 4.58 (br, 1H), 4.46 (dd, J=6.8, 4.0 Hz, 1H), 3.96 (d, J=9.9 Hz, 1H), 3.76 (dd, J=11.1, 6.9 Hz, 1H), 1.66 (br, 1H). $^{13}$C NMR (126 MHz, Chloroform-d) δ 145.79, 139.62, 129.00, 128.96, 127.82, 126.70, 122.49, 114.94, 67.35, 59.94. HR-MS (APCI, positive mode): m/z calc'd for $C_{14}H_{15}ClNO$ [M+H]$^+$:248.0842, found 248.0831.

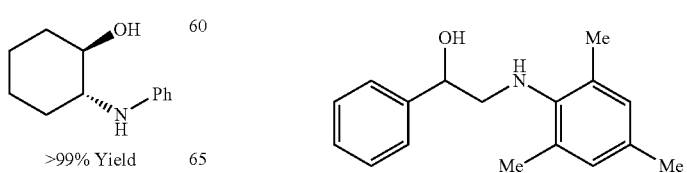

1-phenyl-2-(2,4,6-trimethylanilino)ethanol. ¹H NMR (500 MHz, Chloroform-d) δ 7.32 (m, 2H), 7.29-7.25 (m, 3H), 6.77 (s, 2H), 4.22 (dd, J=6.4, 4.8 Hz, 1H), 3.96 (dd, J=11.1, 6.4 Hz, 1H), 3.89 (dd, J=11.1, 4.9 Hz, 1H), 2.21 (s, 3H), 2.13 (s, 6H). ¹³C NMR (126 MHz, Chloroform-d) δ 141.79, 141.15, 131.28, 129.66, 129.55, 128.64, 127.59, 126.98, 65.85, 63.20, 20.54, 18.81. HR-MS (APCI, positive mode): m/z calc'd for $C_{17}H_{22}NO$ [M+H]⁺:256.1701, found 256.1712.

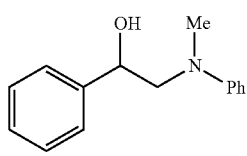 [SMILES: CN(CC(O)c1ccccc1)c1ccccc1]

2-(N-methyl-N-phenylamino)-1-phenylethanol. (CAS: 5455-72-1)¹H NMR (500 MHz, Chloroform-d) δ 7.34-7.23 (m, 5H), 7.19-7.11 (m, 2H), 7.01-6.92 (m, 2H), 6.88-6.79 (m, 1H), 5.10 (dd, J=9.1, 5.7 Hz, 1H), 4.22-4.06 (m, 2H), 2.72 (s, 3H), 2.23-2.11 (m, 1H). ¹³C NMR (126 MHz, Chloroform-d) δ 151.15, 137.44, 129.28, 128.59, 127.62, 127.16, 118.38, 114.81, 64.56, 61.63, 32.01. HR-MS (APCI, positive mode): m/z calc'd for $C_{15}H_{18}NO$ [M+H]⁺: 228.1388, found 228.1399.

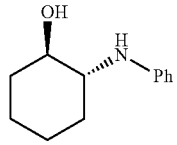 [SMILES: O[C@@H]1CCCC[C@H]1Nc1ccccc1]

2-(phenylamino)cyclohexan-1-ol. (CAS: 75907-11-8)¹H NMR (500 MHz, Chloroform-d) δ 7.23-7.12 (m, 2H), 6.85-6.67 (m, 3H), 3.35 (td, J=9.7, 4.4 Hz, 1H), 3.15 (ddd, J=11.1, 9.1, 4.2 Hz, 1H), 2.78 (br, 1H), 2.28-2.06 (m, 2H), 1.86-1.68 (m, 2H), 1.48-1.23 (m, 3H), 1.19-1.00 (m, 1H). ¹³C NMR (126 MHz, Chloroform-d) δ 147.83, 129.36, 118.38, 114.39, 74.56, 60.16, 33.14, 31.63, 25.05, 24.29. HR-MS (APCI, positive mode): m/z calc'd for $C_{12}H_{18}NO$ [M+H]⁺: 192.1388, found 192.1393.

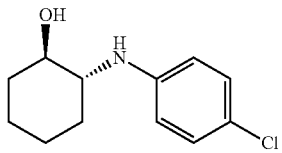 [SMILES: O[C@@H]1CCCC[C@H]1Nc1ccc(Cl)cc1]

2-(4-chlorophenylamino)cyclohexanol. (CAS: 210408-09-6)¹H NMR (500 MHz, Chloroform-d) δ 7.12 (d, J=8.8 Hz, 2H), 6.63 (d, J=8.9 Hz, 2H), 3.47-3.29 (m, 2H), 3.19-3.03 (m, 1H), 2.61 (br, 1H), 2.20-2.05 (m, 2H), 1.87-1.67 (m, 2H), 1.50-1.23 (m, 3H), 1.14-0.98 (m, 1H). ¹³C NMR (126 MHz, Chloroform-d) δ 146.45, 129.16, 122.84, 115.42, 74.55, 60.37, 33.24, 31.54, 24.97, 24.25. HR-MS (APCI, positive mode): m/z calc'd for $C_{12}H_{17}ClNO$ [M+H]⁺20: 226.0999, found 226.1008.

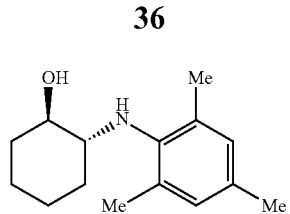

2-(mesitylamino)cyclohexanol. ¹H NMR (500 MHz, Chloroform-d) δ 6.83 (s, 2H), 3.63 (s, 1H), 3.40 (td, J=9.9, 4.4 Hz, 1H), 2.80 (ddd, J=10.9, 9.3, 3.9 Hz, 1H), 2.68 (br, 1H), 2.27 (s, 6H), 2.23 (s, 3H), 2.16-2.11 (m, 1H), 1.85-1.81 (m, 1H), 1.76-1.70 (m, 1H), 1.68-1.62 (m, 1H), 1.39-1.24 (m, 2H), 1.16-1.03 (m, 2H). ¹³C NMR (126 MHz, Chloroform-d) δ 141.32, 131.65, 129.93, 129.76, 75.08, 63.64, 33.06, 32.36, 25.32, 24.32, 20.56, 19.09. HR-MS (APCI, positive mode): m/z calc'd for $C_{15}H_{24}NO$ [M+H]⁺: 234.1858, found 234.1877.

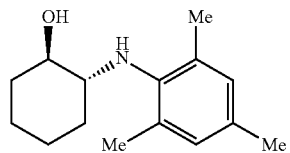 [SMILES: Cc1cc(C)c(N[C@@H]2CCCC[C@H]2O)c(C)c1]

2-(N-methyl-N-phenylamino)cyclohexanol. (CAS: 109128-84-9)¹H NMR (500 MHz, Chloroform-d) δ 7.28 (tt, J=7.3, 6.5, 2.1 Hz, 2H), 7.02-6.94 (m, 2H), 6.84 (td, J=7.2, 1.1 Hz, 1H), 3.69 (td, J=10.1, 4.5 Hz, 1H), 3.43 (ddd, J=11.8, 9.7, 3.7 Hz, 1H), 2.79 (s, 3H), 2.29-2.18 (m, 1H), 1.83-1.70 (m, 3H), 1.50-1.38 (m, 2H), 1.36-1.24 (m, 3H). ¹³C NMR (126 MHz, Chloroform-d) δ 151.42, 129.08, 118.53, 115.61, 70.01, 67.02, 33.35, 31.10, 26.04, 25.48, 24.34. HR-MS (APCI, positive mode): m/z calc'd for $C_{13}H_{20}NO$ [M+H]⁺: 206.1545, found 206.1566.

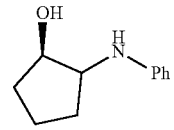 [SMILES: O[C@@H]1CCCC1Nc1ccccc1]

2-(phenylamino)cyclopentanol. (CAS: 109128-84-9)¹H NMR (500 MHz, Chloroform-d) δ 7.22-7.16 (m, 2H), 6.72 (tt, J=7.3, 1.1 Hz, 1H), 6.69-6.65 (m, 2H), 4.06 (dt, J=6.1, 4.4 Hz, 1H), 3.61 (td, J=6.7, 4.1 Hz, 1H), 2.32-2.24 (m, 1H), 1.99 (ddt, J=13.1, 8.7, 6.5 Hz, 1H), 1.88-1.70 (m, 2H), 1.64 (ddt, J=13.6, 8.6, 5.1 Hz, 1H), 1.41 (dddd, J=13.2, 8.7, 7.1, 6.0 Hz, 1H). ¹³C NMR (126 MHz, Chloroform-d) δ 147.72, 129.30, 117.53, 113.34, 78.21, 62.07, 32.85, 31.17, 21.01. HR-MS (APCI, positive mode): m/z calc'd for $C_{11}H_{16}NO$ [M+H]⁺:178.1232, found 178.1247.

A "hot filtration" test was performed to rule out the possibility of leached Lewis acidic metal species or soluable Bronsted acidic species contributing to the epoxide ring-opening reaction reactivity. More particularly, 1.0 mol % of ZrOTf-BTC was first used to catalyze reaction between styrene oxide and aniline to give 1-phenyl-2-phenylamino-ethanol in 62% yield in 2 hours. Then, the MOF and supernatant were separated via centrifugation and used as catalysts, respectively, for the ring-opening reaction between cyclohexene oxide and aniline without further treatment. The recovered ZrOTf-BTC catalyst afforded 2-(phenylamino)cyclohexan-1-ol in 95% yield in 5 hours, while only less then 1% cyclolation product was detected in the reaction catalyzed by the supernatant. This result excludes the possibility of leached Zr species or soluable Brönsted acids contributing to the catalytic reactivity.

Example 7

Epoxide Ring-Opening Reactions Catalyzed by ZrOTf-BTC in Flow Mode

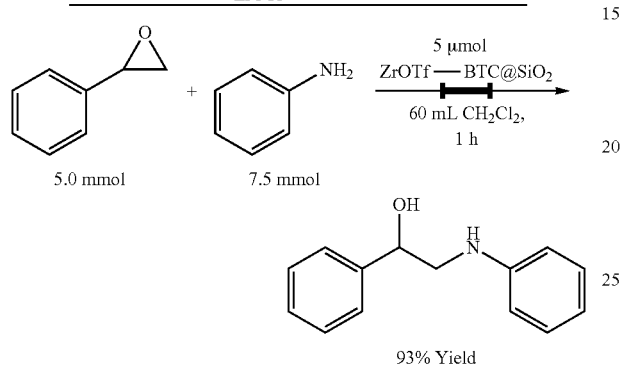

Scheme 9. Exemplary Epoxide Ring-Opening Catalyzed by ZrOTf—BTC.

As shown in Scheme 9, above, for a one-hour flow catalysis of epoxide ring-opening reaction, styrene oxide (570 μL, 5.0 mmol) and aniline (690 μL, 7.5 mmol) were dissolved in $CH_2Cl_2$ (50 mL). The solution was flowed through the ZrOTf-BTC@SiO$_2$ column at a rate of 60 mL·h$^{-1}$ at room temperature. After the flow, 10 mL of $CH_2Cl_2$ was used to wash the column to recover the remaining product. The collected solution was evaporated on a rotovap to remove the solvent, then 1 equiv. of mesitylene was added as an internal standard. The mixture was analyzed with $^1$H NMR to give 1-phenyl-2-(phenylamino)ethanol in a quantitative yield.

Example 8

Epoxide Ring-Opening Reactions Catalyzed by ZrOTf-BTC in Batch Mode

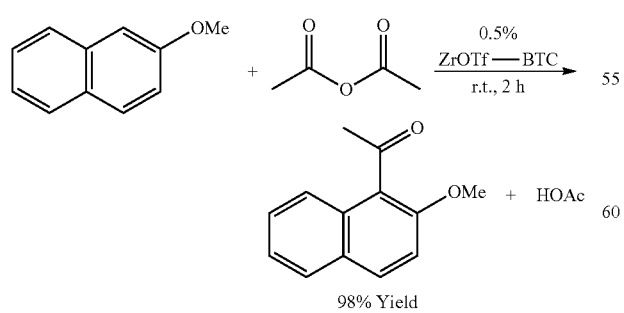

Scheme 10. Exemplary Friedel-Crafts Acylation Catalyzed by ZrOTf—BTC.

A typical procedure of ZrOTf-BTC catalyzed Friedel-Crafts acylations in batch mode is shown in Scheme 10, above. Under ambient atmosphere, 2-methoxynapthalene (158 mg, 1.0 mmol), acetic anhydride (1.0 mL, neat), and ZrOTf-BTC (5 μmol Zr) were charged to a 2-dram vial. The reaction mixture was stirred at room temperature for 2 h, then the MOF catalyst was removed by centrifugation. The residue was further washed several times with NaHCO$_3$(aq) to remove the excess acetic anhydride and HOAc, before purified by silica gel chromatography (hexane/CH$_2$Cl$_2$). Target molecule was achieved as a white solid with 98% isolated yield. The MOF crystallinity was maintained after the reaction run and minimum metal leaching with 0.23% of Zr per run was detected by ICP-MS analysis. PXRD patterns showed retention of ZrOTf-BTC crystallinity after Friedel-Crafts acylations (when compared to PXRD of freshly prepared ZrOTf-BTC and simulated MOF-808 pattern).

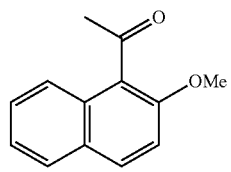

1-acetyl-2-methoxynaphthalene. (CAS: 5672-94-6)$^1$H NMR (500 MHz, Chloroform-d) δ 7.89 (d, J=8.8 Hz, 1H), 7.81-7.78 (m, 1H), 7.76 (dd, J=8.6, 1.0 Hz, 1H), 7.48 (ddd, J=8.5, 6.8, 1.4 Hz, 1H), 7.37 (ddd, J=8.0, 6.8, 1.1 Hz, 1H), 7.28 (d, J=9.1 Hz, 1H), 3.97 (s, 3H), 2.65 (s, 3H). $^{13}$C NMR (126 MHz, Chloroform-d) δ 205.22, 153.96, 131.48, 130.31, 128.85, 128.17, 127.69, 125.09, 124.10, 123.64, 112.77, 56.41, 32.73. HR-MS (APCI, positive mode): m/z calc'd for $C_{13}H_{13}O_2$ [M+H]$^+$:201.0916, found 201.0920.

Additional products prepared by analogous ZrOTf-BTC catalyzed Friedel-Crafts acylation reactions.

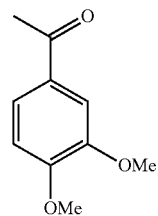

1-(3,4-dimethoxyphenyl)ethanone. (CAS: 1131-62-0)$^1$H NMR (500 MHz, Chloroform-d) δ 7.56 (dd, J=8.3, 2.0 Hz, 1H), 7.51 (d, J=2.1 Hz, 1H), 6.87 (d, J=8.4 Hz, 1H), 3.93 (s, 3H), 3.92 (s, 3H), 2.56 (s, 3H). $^{13}$C NMR (126 MHz, Chloroform-d) δ 196.85, 153.27, 148.96, 130.46, 123.29, 110.01, 109.91, 56.06, 55.96, 26.21. HR-MS (APCI, positive mode): m/z calc'd for $C_{10}H_{13}O_3$ [M+H]$^+$: 181.0865, found 181.0876.

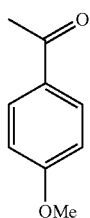

1-(4-methoxyphenyl)ethanone. (CAS: 100-06-1)$^1$H NMR (500 MHz, Chloroform-d) δ 7.96-7.92 (m, 2H), 6.95-6.91 (m, 2H), 3.87 (s, 3H), 2.55 (s, 3H). $^{13}$C NMR (126 MHz, Chloroform-d) δ 196.83, 163.49, 130.61, 130.34, 113.69, 55.49, 26.38. HR-MS (APCI, positive mode): m/z calc'd for $C_9H_{11}O_2$ [M+H]$^+$:151.0759, found 151.0760.

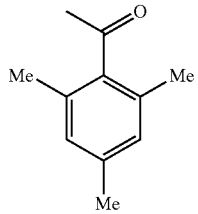

2,4,6-Trimethylacetophenone. (CAS: 1667-01-2)$^1$H NMR (500 MHz, Chloroform-d) δ 6.87-6.81 (m, 2H), 2.46 (s, 3H), 2.28 (s, 3H), 2.22 (s, 6H). $^{13}$C NMR (126 MHz, Chloroform-d) δ 208.69, 139.90, 138.35, 132.33, 128.52, 32.27, 21.05, 19.15. HR-MS (APCI, positive mode): m/z calc'd for $C_{11}H_{15}O$ [M+H]$^+$: 163.1123, found 163.1126.

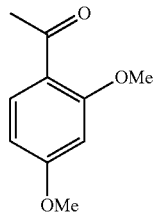

1-(2,4-dimethoxyphenyl)ethanone. (CAS: 829-20-9)$^1$H NMR (500 MHz, Chloroform-d) δ 7.83 (d, J=8.8 Hz, 1H), 6.52 (dd, J=8.7, 2.3 Hz, 1H), 6.45 (d, J=2.3 Hz, 1H), 3.89 (s, 3H), 3.85 (s, 3H), 2.57 (s, 3H). $^{13}$C NMR (126 MHz, Chloroform-d) δ 197.80, 164.54, 161.10, 132.72, 121.16, 105.01, 98.32, 55.55, 55.46, 31.88. HR-MS (APCI, positive mode): m/z calc'd for $C_{10}H_{13}O_3$ [M+H]$^+$: 181.0865, found 181.0858.

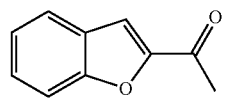

1-(benzo[b]furan-2-yl)ethanone. (CAS: 1646-26-0)$^1$H NMR (500 MHz, Chloroform-d) δ 7.71 (ddd, J=7.9, 1.3, 0.8 Hz, 1H), 7.58 (dq, J=8.4, 0.9 Hz, 1H), 7.50 (d, J=1.0 Hz, 1H), 7.48 (ddd, J=8.5, 7.2, 1.3 Hz, 1H), 7.31 (ddd, J=8.0, 7.2, 1.0 Hz, 1H), 2.61 (s, 3H). $^{13}$C NMR (126 MHz, Chloroform-d) δ 188.69, 155.70, 152.68, 128.30, 127.08, 123.94, 123.32, 113.07, 112.50, 26.49. HR-MS (APCI, positive mode): m/z calc'd for $C_{10}H_9O_2$ [M+H]$^+$:161.0603, found 161.0600.

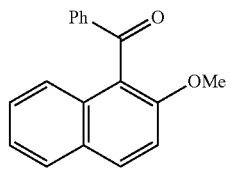

1-benzoyl-2-methoxynaphthalene. (CAS: 14344-14-0)$^1$H NMR (500 MHz, Chloroform-d) δ 7.99-7.95 (m, 1H), 7.85 (td, J=7.9, 1.7 Hz, 3H), 7.59-7.54 (m, 1H), 7.53-7.50 (m, 1H), 7.45-7.41 (m, 2H), 7.40-7.33 (m, 3H), 3.83 (s, 3H). $^{13}$C NMR (126 MHz, Chloroform-d) δ 197.82, 154.09, 137.93, 133.50, 131.72, 131.20, 129.65, 128.80, 128.60, 128.14, 127.42, 124.12, 124.09, 113.11, 56.56. HR-MS (APCI, positive mode): m/z calc'd for $C_{18}H_{15}O_2$ [M+H]$^+$:263.1072, found 263.1068.

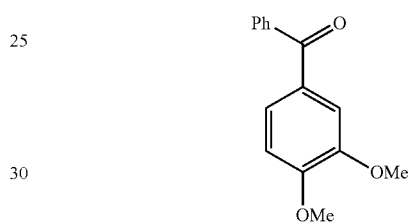

3,4-dimethoxybenzophenone. (CAS: 4038-14-6)$^1$H NMR (500 MHz, Chloroform-d) δ 7.82-7.75 (m, 2H), 7.59 (ddq, J=7.4, 6.6, 1.2 Hz, 1H), 7.52 (d, J=2.0 Hz, 1H), 7.51-7.48 (m, 3H), 7.40 (ddd, J=8.3, 2.0, 0.7 Hz, 1H), 6.91 (d, J=8.3 Hz, 1H), 3.98 (d, J=0.7 Hz, 3H), 3.96 (d, J=0.7 Hz, 3H). $^{13}$C NMR (126 MHz, Chloroform-d) δ 195.63, 153.02, 149.01, 138.28, 131.91, 130.21, 129.74, 128.19, 125.55, 112.09, 109.71, 56.11, 56.06. HR-MS (APCI, positive mode): m/z calc'd for $C_{15}H_{15}O_3$ [M+H]$^+$:243.1021, found 243.1019.

A "hot filtration" test was performed to rule out the possibility of leached Lewis acidic metal species or soluable Brönsted acidic species contributing to the Friedel-Crafts acylations reactivity. More particularly, 1.0 mol % of ZrOTf-BTC was first used to catalyze acylation reaction of 2-methoxynaphthalene in neat Ac$_2$O to give 1-acetyl-2-methoxynaphthalene in 97% of yield in 2 hours. Then, the MOF and supernatant were separated via centrifugation and used as catalysts, respectively, for the Friedel-Crafts acylations of 1,2-dimethoxybenzene without further treatment. The recovered ZrOTf-BTC catalyst afforded 1-(3,4-dimethoxyphenyl)ethanone in 42% yield in 2 hours, while no acylation product was detected in the reaction catalyzed by the supernatant. This result excludes the possibility of leached Zr species or soluable Brönsted acids contributing to the catalytic reactivity.

Example 9

ZrOTf-BTC Catalyzed Freidel-Crafts Acylations in Flow Mode

Scheme 11. Exemplary Freidel-Crafts Acylation Catalyzed by ZrOTf—BTC in Flow Mode.

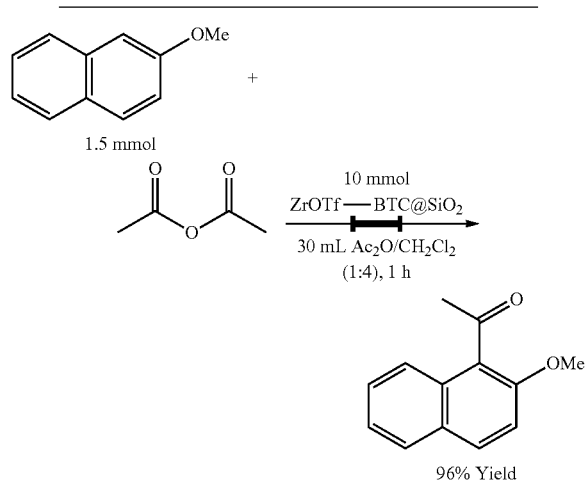

As shown in Scheme 11, above, for a one-hour flow catalysis of Friedel-Crafts acylations, 2-methoxynaphthlene (237 mg, 1.5 mmol) was dissolved in a mixed solution of $Ac_2O/CH_2Cl_2$ (1:4, 30 mL). The solution was flowed through the ZrOTf-BTC@$SiO_2$ column at a rate of 30 mL·h$^{-1}$ at room temperature. The product-containing solution was collected in several 5 mL vials and was evaporated on a rotovap to remove the solvent, then 1 equiv. of mesitylene was added as an internal standard. The mixture was analyzed with $^1$H NMR to give 1-acetyl-2-methoxynaphthalene in a quantitative yield.

Example 10

ZrOTf-BTC Catalyzed Intramolecular Hydroalkoxylation

Scheme 12. Exemplary Intramolecular Hydroalkoxidation Reaction Catalyzed by ZrOTf—BTC.

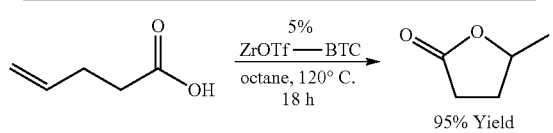

As shown in Scheme 12, above, ZrOTf-BTC (10 µmol Zr), pent-4-enoic acid (100 mg, 1.0 mmol), and octane (2.0 mL) were charged to a pressure resistant vial and sealed under ambient atmosphere. The reaction mixture was stirred at 120° C. for 18 h. After cool down, the reaction slurry was then centrifugated to remove MOF catalyst. The supernatant was analyzed by $^1$H NMR to give the 4-methylbutyrolactone product in 95% yield. The crude product was further purified by silica gel chromatography eluting with pentane/$Et_2O$ to afford the target molecule as a colorless oil (87% isolated yield). The MOF crystallinity was maintained after the reaction run and minimum metal leaching with 0.20% of Zr per run was detected by ICP-MS analysis. PXRD patterns showed retention of ZrOTf-BTC crystallinity after intramolecular hydroalkoxidation reactions (when compared to PXRD of freshly prepared ZrOTf-BTC and simulated MOF-808 pattern).

Products prepared by ZrOTf-BTC catalyzed intramolecular hydroalkoxidation reactions:

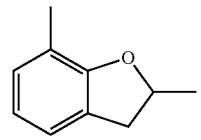

2-methyl-2,3-dihydro-1-benzofuran. (CAS: 1746-11-8) $^1$H NMR (500 MHz, Chloroform-d) 7.18-7.14 (m, 1H), 7.11 (dddt, J=8.2, 7.5, 1.5, 0.8 Hz, 1H), 6.83 (td, J=7.4, 1.0 Hz, 1H), 6.76 (dq, J=8.0, 0.5 Hz, 1H), 4.92 (ddq, J=8.8, 7.7, 6.3 Hz, 1H), 3.31 (dd, J=15.4, 8.8, 1H), 2.82 (dd, J=15.3, 7.6, 1H), 1.47 (d, J=6.2 Hz, 3H). $^{13}$C NMR (126 MHz, Chloroform-d) δ 159.50, 127.96, 124.98, 120.17, 109.34, 79.50, 37.14, 21.78. HR-MS (APCI, positive mode): m/z calc'd for $CH_{11}O$ [M+H]$^+$:135.0810, found 135.0802.

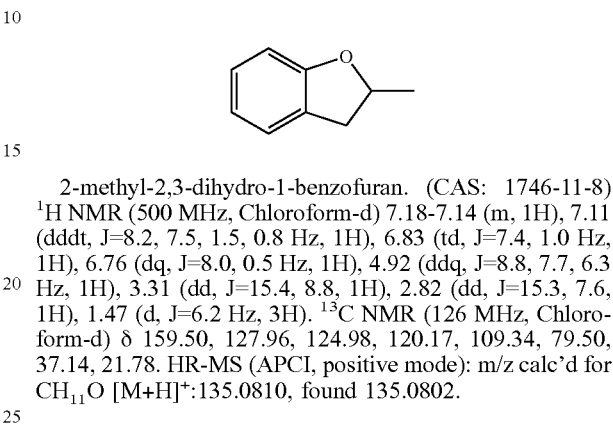

2,7-dimethyl-2,3-dihydrobenzofuran. (CAS: 3199-41-5) $^1$H NMR (500 MHz, Chloroform-d) δ 7.00 (d, J=7.3 Hz, 1H), 6.94 (ddq, J=7.4, 1.5, 0.7 Hz, 1H), 6.75 (t, J=7.4 Hz, 1H), 4.91 (ddq, J=8.8, 7.8, 6.3 Hz, 1H), 3.31 (ddt, J=15.3, 8.8, 0.9 Hz, 1H), 2.82 (ddt, J=15.3, 7.8, 1.0 Hz, 1H), 2.21 (s, 3H), 1.48 (d, J=6.3 Hz, 3H). $^{13}$C NMR (126 MHz, Chloroform-d) δ 158.00, 129.15, 126.27, 122.29, 120.00, 119.48, 79.13, 37.49, 21.90, 15.32. HR-MS (APCI, positive mode): m/z calc'd for $C_{10}H_{13}O$ [M+H]$^+$:149.0966, found 149.0956.

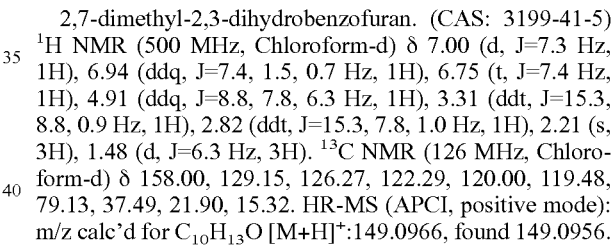

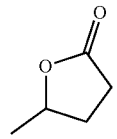

γ-valerolactone. (CAS: 108-29-2) $^1$H NMR (500 MHz, Chloroform-d) δ 4.63 (dp, J=7.9, 6.3 Hz, 1H), 2.53 (ddd, J=9.3, 6.9, 2.4 Hz, 2H), 2.39-2.30 (m, 1H), 1.81 (dtd, J=12.7, 9.4, 7.9 Hz, 1H), 1.40 (d, J=6.2 Hz, 3H). $^{13}$C NMR (126 MHz, Chloroform-d) δ 177.27, 77.27, 29.69, 29.09, 21.06. HR-MS (APCI, positive mode): m/z calc'd for $C_5H_9O_2$ [M+H]$^+$:101.0603, found 101.0600.

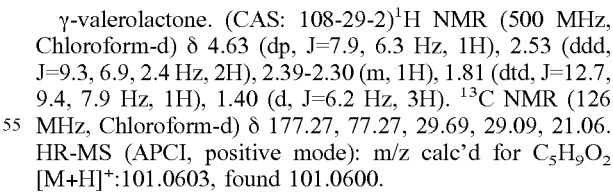
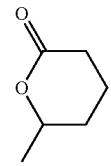

δ-hexalactone. (CAS: 823-22-3)$^1$H NMR (500 MHz, Chloroform-d) δ 4.41 (dtd, J=7.9, 6.8, 5.8 Hz, 1H), 2.51 (dd, J=9.6, 7.0 Hz, 2H), 2.30 (dq, J=12.7, 6.8 Hz, 1H), 1.84 (dtd, J=12.8, 9.5, 7.9 Hz, 1H), 1.74 (dq, J=14.6, 7.3 Hz, 1H), 1.62 (dqd, J=13.5, 7.5, 5.8 Hz, 1H), 1.02-0.94 (m, 3H). $^{13}$C NMR (126 MHz, Chloroform-d) δ 177.31, 82.18, 28.83, 28.45, 27.45, 9.40. HR-MS (APCI, positive mode): m/z calc'd for $C_6H_{11}O_2$ [M+H]$^+$:115.0759, found 115.0759.

Example 11

Recycle of ZrOTf-BTC Catalyst in Intramolecular Hydroalkoxidation Reaction

ZrOTf-BTC (50 μmol Zr), 4-penten-1-ol (103 μL, 1.0 mmol), and decane (2.0 mL) were added to a 2-dram vial under ambient atmosphere. The reaction mixture was stirred at 120° C. for 18 h for the reaction. The reaction slurry was then centrifugated to recover the MOF catalyst. The supernatant was analyzed by $^1$H NMR to give the 2-methyltetrahydrofuran product in quantitative yield.

The recovered MOF was washed with decane 3 times before being used for another round of catalysis, then added to a new solution of 4-penten-1-ol (103 μL, 1.0 mmol) in decane (2.0 mL). The reaction mixture was stirred at 120° C. for 18 h for the reaction to complete, and then recycled and monitored using the same procedure. The catalyst was recycled and reused for at least 5 times without a significant drop in catalytic activity.

Example 12

Discussion of Examples 2-11

Figure 4A:
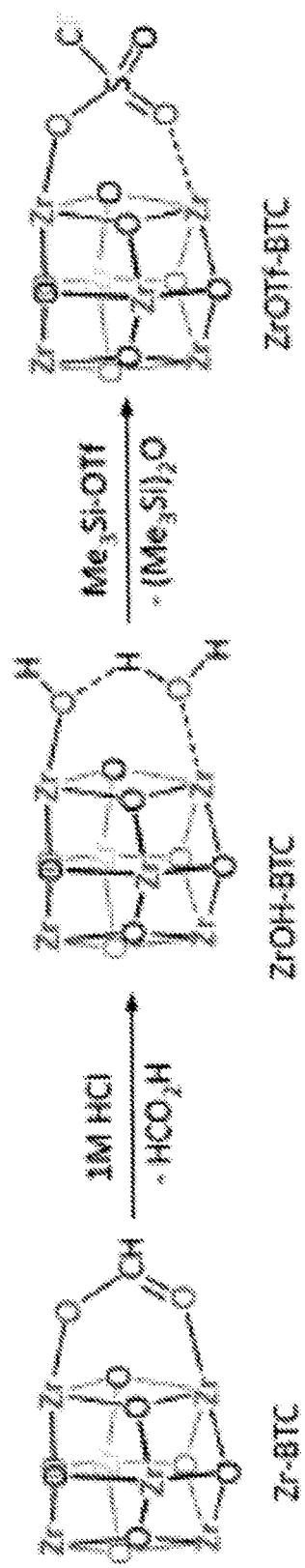
FIG. 4A is a schematic diagram showing the synthesis of zirconium triflate-trimesic acid (ZrOTf-BTC) metal-organic framework (MOF) through stepwise activation of a zirconium-trimesic acid (Zr-BTC) MOF with 1 molar (M) hydrochloric acid (HCl) and trimethylsilyl trifluoromethanesulfonate ($Me_3SiOTf$). For simplicity, only the structure of the metal secondary building unit is shown.

Synthesis and characterization of ZrOTf-BTC: A strategy to install metal triflate active sites at MOF nodes through post-synthetic triflation of metal hydroxide groups was developed. See FIG. 4A. Zr-BTC was synthesized following a literature procedure by a solvothermal reaction of trimesic acid and $ZrOCl_2 \cdot 8H_2O$ in a mixture of N,N-dimethylformamide (DMF) and formic acid.[44] The inorganic node of Zr-BTC has the composition of $Zr_6(\mu_3-O)_4(\mu_3-OH)_4(RCO_2)(HCO_2)_6$, where six formate groups cap all the peripheral sites around the $Zr_6$ octahedron. Zr-BTC was subsequently activated with 1 M aqueous HCl at 100° C. for 18 h to replace the formate groups with six pairs of Zr-coordinated hydroxide and water groups to afford ZrOH-BTC with the inorganic node composition of $Zr_6(\mu_3-O)_4(\mu_3-OH)_4(RCO_2)_6[(OH)(OH_2)]$. ZrOH-BTC was then treated with trimethylsilyl triflate ($Me_3SiOTf$) in benzene at 80° C. for 8 h to afford ZrOTf-BTC. As the oxophilic $Me_3Si$ group forms a stronger bond with the —OH moiety than with the -OTf moiety, $Me_3SiOTf$ readily removes OH$^-$ from ZrOH-BTC to generate ZrOTf-BTC with the node composition of $Zr_6(\mu_3-O)_4(\mu_3-OH)_4(RCO_2)_6[OTf]_6$. The $Me_3SiOH$ byproduct generated through this activation reacted with excess $Me_3SiOTf$ to form $(Me_3Si)_2O$. The amount of $(Me_3Si)_2O$ was quantified to be 0.90 equiv. by weight with respect to (w.r.t.) Zr by $^1$H NMR, agreeing well with the proposed activation process.

Figure 4C:
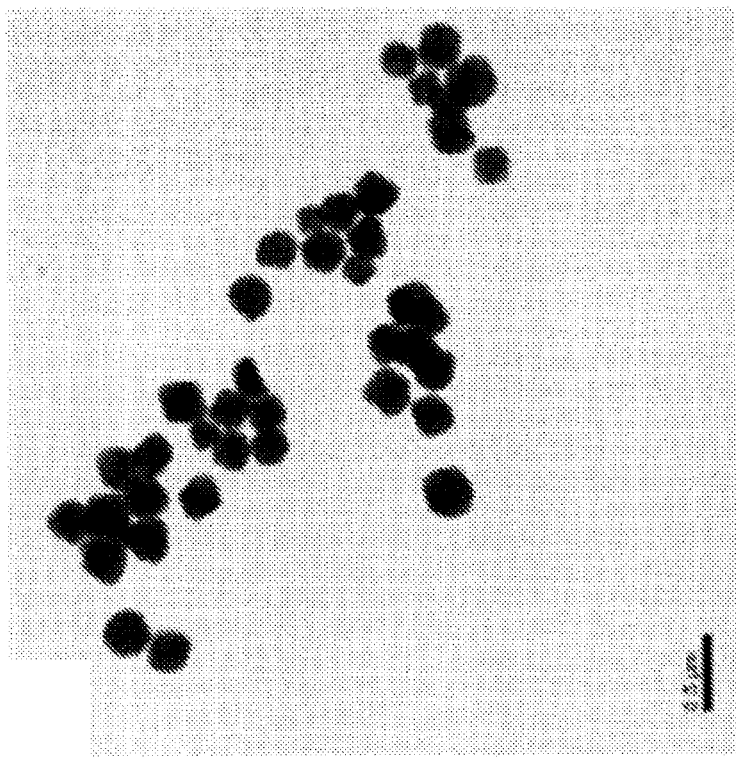
FIG. 4C is a transmission electron spectroscopy (TEM) images of a zirconium triflate-trimesic acid (ZrOTf-BTC) metal-organic framework showing octahedral morphology with an average diameter of 200 nanometers (nm).
Figure 4B:
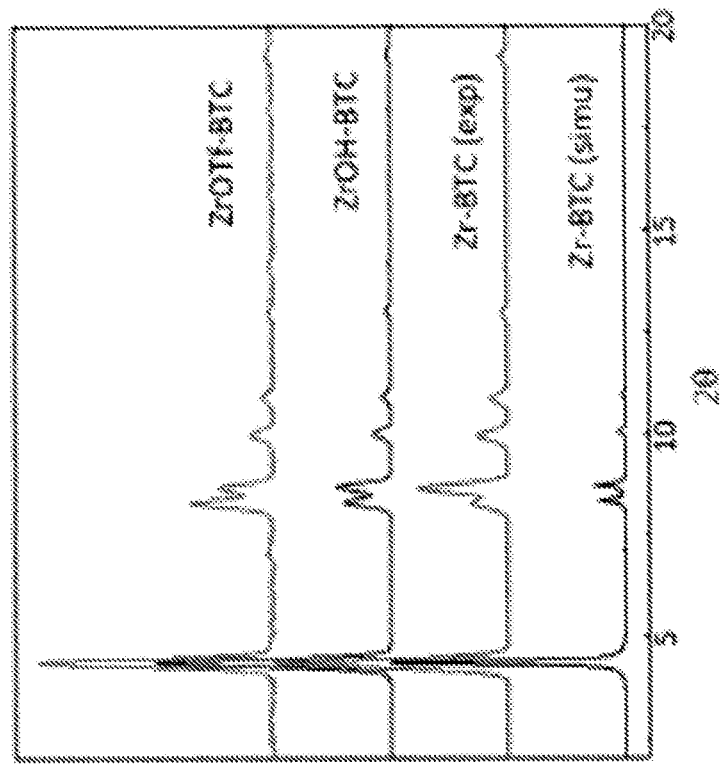
FIG. 4B is a graph showing the similarity between powder x-ray diffraction (PXRD) patterns of zirconium triflate-trimesic acid (ZrOTf-BTC) metal-organic framework (MOF) (ZrOTf-BTC, top), a zirconium-trimesic acid (Zr-BTC) MOF (Zr-BTC, second from bottom), and a zirconium hydroxide-trimesic acid (ZrOH-BTC) MOF (ZrOH-BTC, second from top) indicating the maintenance of MOF crystallinity throughout post-synthetic treatments. For comparison, a simulated PXRD pattern of Zr-BTC is also shown (bottom).
Figure 4E:
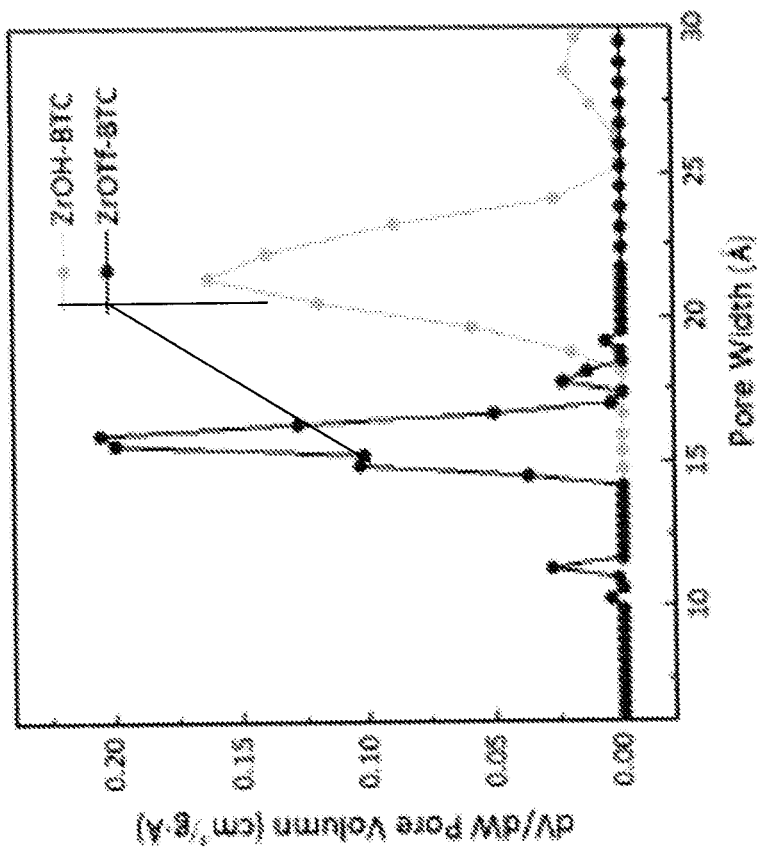
FIG. 4E is a graph showing the pore size distribution of zirconium triflate-trimesic acid (ZrOTf-BTC) metal-organic framework (MOF) particles (ZrOTf-BTC, darker line) showing a uniform pore size of 16 angstroms (Å), which is smaller than that of zirconium hydroxide-trimesic acid (ZrOH-BTC) MOF particles (ZrOH-BTC, 21 Å, lighter line) due to the presence of six triflate groups per hexagonal pore in ZrOTf-BTC.
Figure 4D:
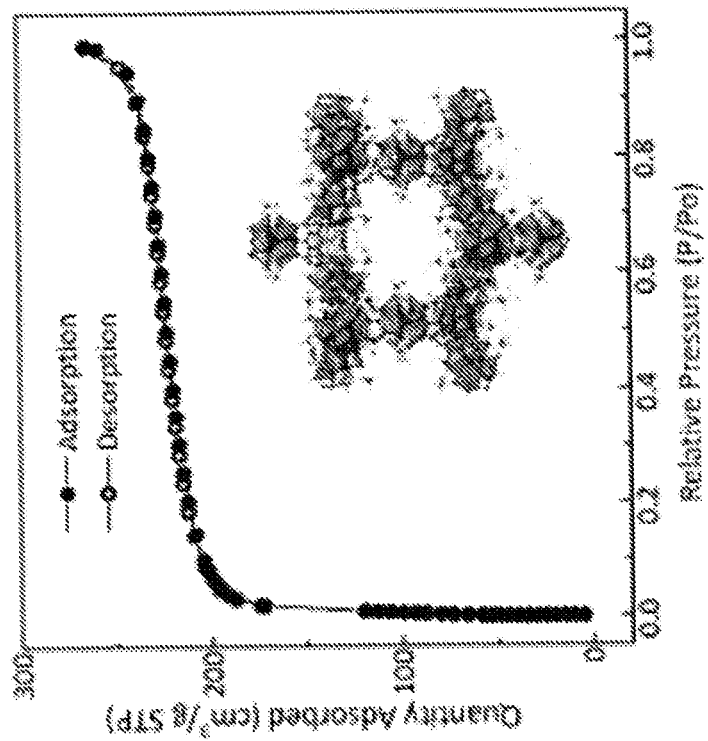
FIG. 4D is a graph showing the nitrogen ($N_2$) sorption isotherms of a zirconium triflate-trimesic acid (ZrOTf-BTC) metal-organic framework with a calculated Brunuaer-Emmett-Teller (BET) surface area of 779 square meters per gram ($m^2/g$).

Thermogravimetric analysis (TGA) of ZrOTf-BTC showed a weight loss of 63.8% in the 220-800° C. range, consistent with the expected weight loss of 62.8% for the conversion of $Zr_6(\mu_3-O)_4(\mu_3-OH)_4(BTC)_2(OTf)_6$ to $(ZrO_2)_{12}$. Powder X-ray diffraction (PXRD) studies showed that ZrOTf-BTC remains crystalline and maintains the structure of ZrOH-BTC. See FIG. 4B. Transmission Electron Microscope (TEM) images of ZrOTf-BTC displayed highly crystalline octahedral particles of ~200 nm in dimensions. See FIG. 4C. The porosity of ZrOTf-BTC was confirmed by $N_2$ sorption isotherms, with a Brunauer-Emmett-Teller (BET) surface area of 779 m$^2$/g. See FIG. 4D. Pore size analysis by nonlinear density functional-theory (NL-DFT) showed a uniform pore at ~16 Å that is attributable to the large hexagonal cages of the MOF. The pore size of ZrOTf-BTC is smaller than that of ZrOH-BTC (21 Å) due to the presence of six large triflate groups per SBU. See FIG. 4E.

Figure 5A:
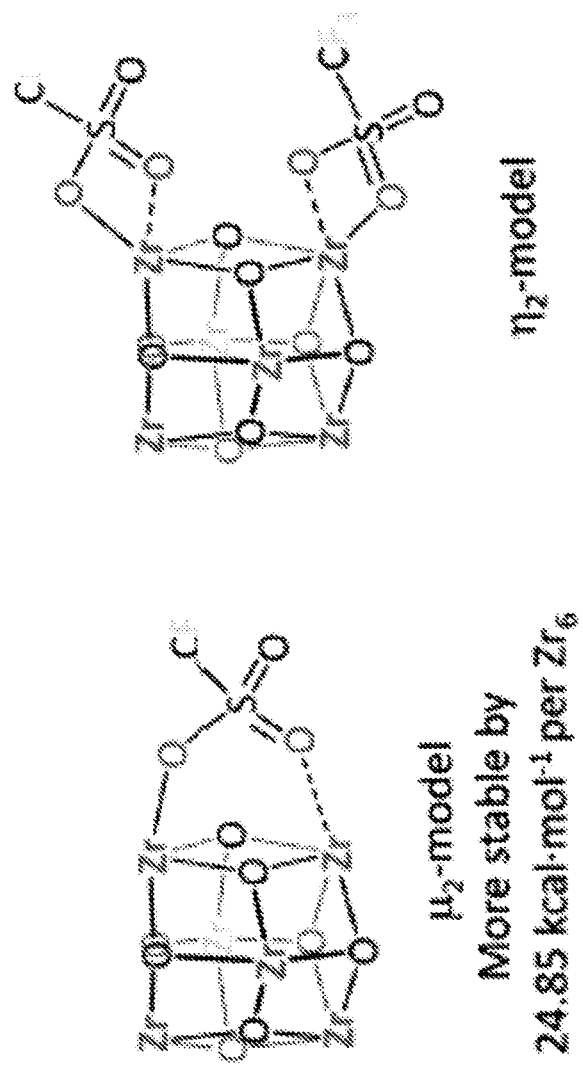
FIG. 5A is a schematic diagram showing the discrete Fourier transform (DFT) optimized structures of zirconium triflate-trimesic acid (ZrOTf-BTC) with $Zr_2(\mu_2\text{-OTf})$ (left) and $Zr(\eta^2\text{-OTf})$ (right) coordination modes. The $\mu_2$-model is more stable than the $\eta_2$-model by 24.85 kilocalories per mole (kcal·$mol^{-1}$) per $Zr_6O_4(OH)_4(OTf)_6$ node. For simplicity, only the structure of the metal secondary building unit is shown.
Figure 5C:
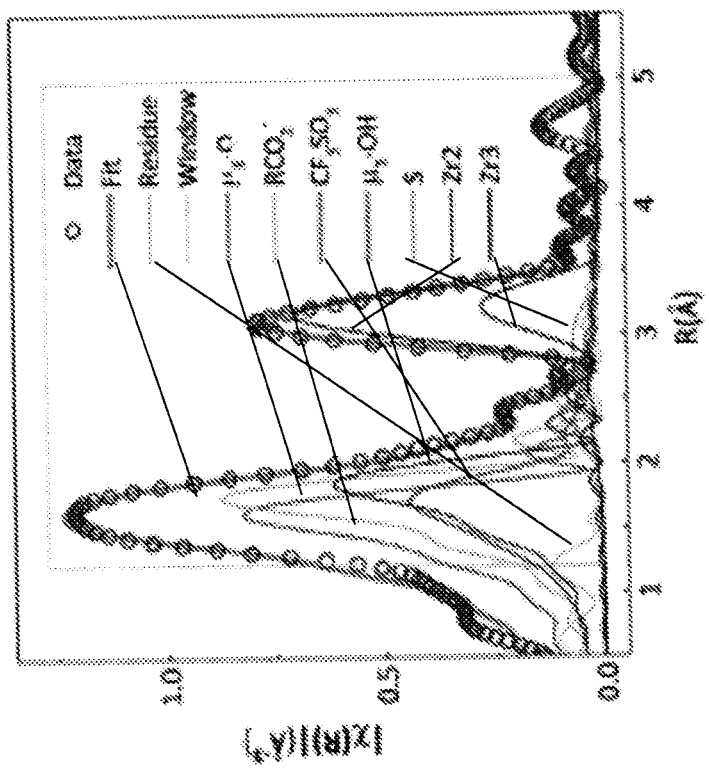
FIG. 5C is a graph showing the fitting of zirconium triflate-trimesic acid (ZrOTf-BTC) extended x-ray absorption fine structure (EXAFS) data using the $\mu_2$-model. The R-factor for the fitting is 0.007.
Figure 5B:
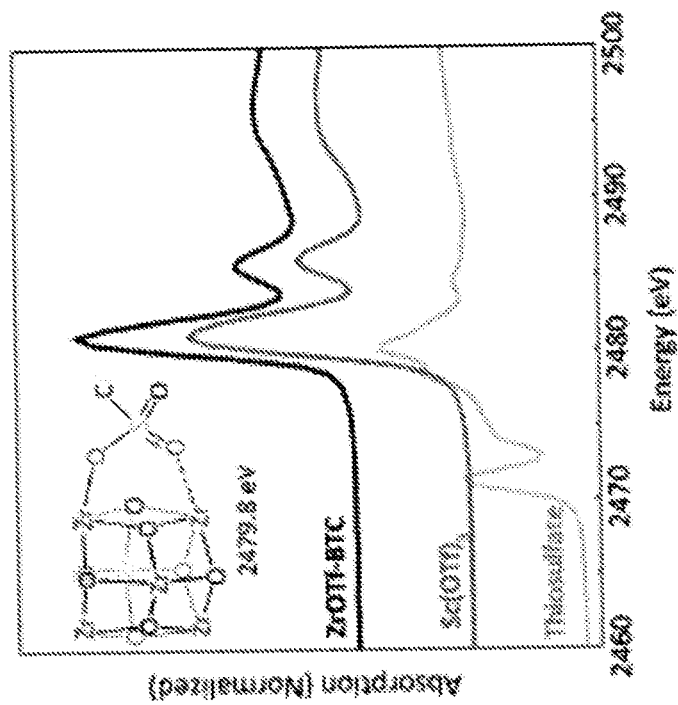
FIG. 5B is a graph showing the sulfur X-ray absorption near edge structure (XANES) spectra of ZrOTf-BTC (top), sodium thiosulfate (bottom), and $Sc(OTf)_3$ (middle) indicating the presence of triflate groups in ZrOTf-BTC.

Computational and spectroscopic studies of Zr-OTf active sites: A range of computational and spectroscopic techniques, including density functional theory (DFT), extended X-ray absorption fine-structure (EXAFS) and X-ray near-edge spectroscopy (XANES), was used to elucidate the Zr coordination environment in ZrOTf-BTC. The first question what was addressed is whether triflate groups are incorporated into the MOF. Sulfur K-edge XANES analysis was performed to prove the presence of triflate groups. The sulfur centers in ZrOTf-BTC displayed significant edge-step, with the K-edge energy of at 2479.8 eV This energy is much higher than that of sodium thiosulfate ($Na_2S_2O_3$) standard and matched well to the edge energy of $Sc(OTf)_3$, indicating the presence of triflate groups in ZrOTf-BTC. See FIG. 5B.

The next question that was addressed was how triflate groups are coordinated to Zr centers. Two possible modes of triflate coordination were envisioned (see FIG. 5A): OTf bridging two proximal Zr centers (the $\mu_2$-model) or OTf chelation to a single Zr center (the $\eta^2$-model). Both of these coordination modes are commonly observed in the crystal structures of molecular metal-OTf complexes. Both structures were optimized using DFT at the B3LYP level of theory, and their free energies were calculated to compare their relative stability. The optimized structure for the $\mu_2$-model showed an average Zr—O$^{OTf}$ bond distance of 2.269 Å, which is similar to reported Zr—O$^{OTf}$ bond distances in molecular $Zr_2(OTf)$ complexes.[45-46] The optimized structure for the $\eta^2$-model showed an average Zr—O$^{OTf}$ bond distance of 2.299 Å, which is longer than that of the $\mu_2$ model by 0.030 Å. Bond distance analysis thus showed stronger bonding between $\mu_2$-triflates and Zr centers. Free energy calculations also indicated the $\mu_2$ model is thermodynamically more stable, with 24.85 kcal-mol-1 lower free energy than the $\eta^2$-model per six Zr centers. The DFT optimized $\mu_2$ model fitted well to the Zr k-edge EXAFS spectrum of ZrOTf-BTC, with an R-factor of 0.007. See FIG. 5C. The fitted Zr-OTf bond distances have an average value of 2.20 Å, similar to that calculated by DFT (2.269 Å). The ZrOTf-BTC spectrum was also be fitted with the DFT optimized $\eta^2$ model, but the fitting afforded significant shortening of the Zr-$\eta^2$-OTf bond distance by 0.090 Å to 2.209 Å when compared to the DFT optimized Zr—O$^{OTf}$ distance. EXAFS studies thus favor the $\mu_2$ coordination mode as well.

Quantification of ZrOTf-BTC Lewis acidity by spectroscopic methods: The Lewis acidity of ZrOTf-BTC was quantified using two spectroscopic methods that were recently developed, including electron paramagnetic resonance (EPR) spectroscopy of MOF-bound superoxides ($O_2^{*-}$) and fluorescence spectroscopy of MOF-bound N-methylacridone (NMA).[21] ZrOTf-BTC was shown to be more Lewis acidic than ZrOH-BTC and the previously reported $Zr_6$-fBDC based on the Lewis acidity measurement using both techniques.

Figure 6A:
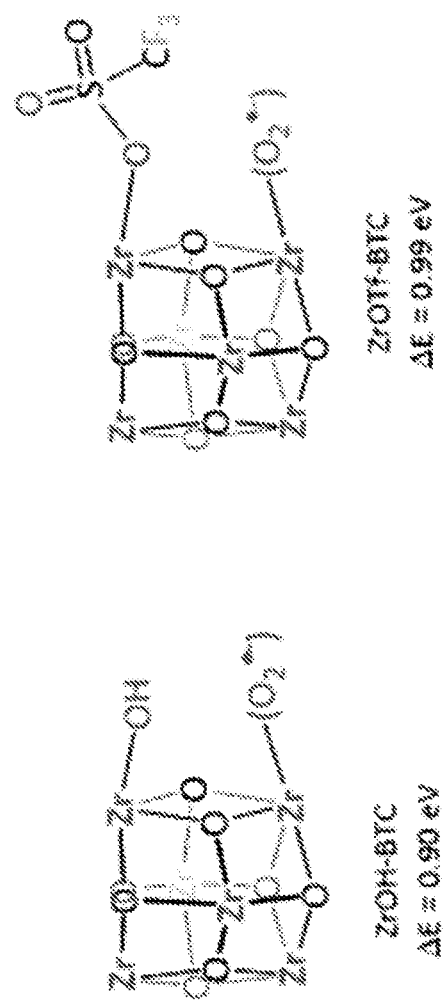
FIG. 6A is a schematic drawing showing proposed chemical structures for superoxide-coordinated zirconium hydroxide-trimesic acid (ZrOH-BTC) (left) and zirconium triflate-trimesic acid (ZrOTf-BTC) (right). For simplicity, only the structure of the metal secondary building unit is shown.
Figure 6C:
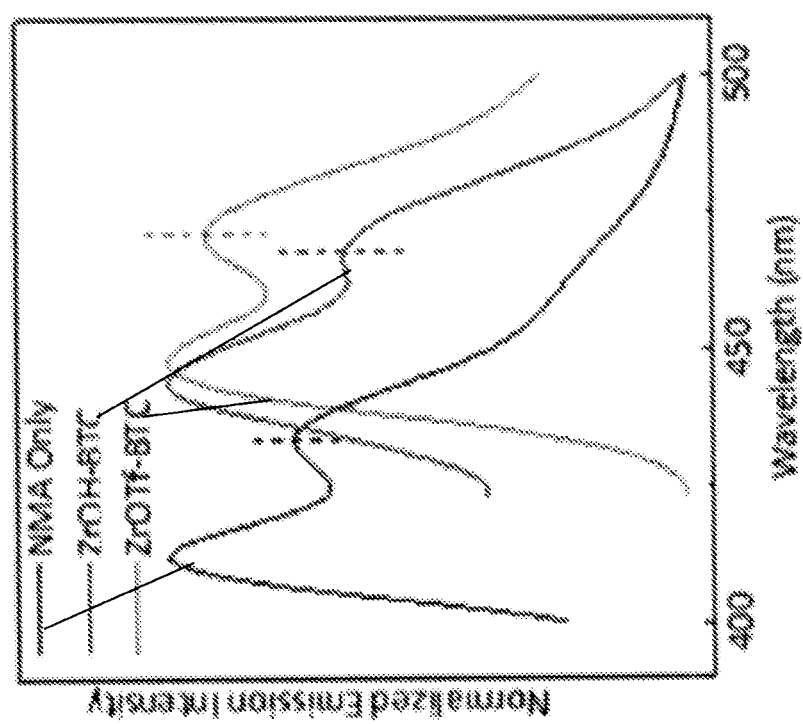
FIG. 6C is a graph showing the fluorescence spectra of N-methylacridone (NMA)-coordinated zirconium triflate-trimesic acid (ZrOTf-BTC, right), NMA-coordinated zirconium hydroxide-trimesic acid (ZrOH-BTC, middle), and free NMA (left).
Figure 6B:
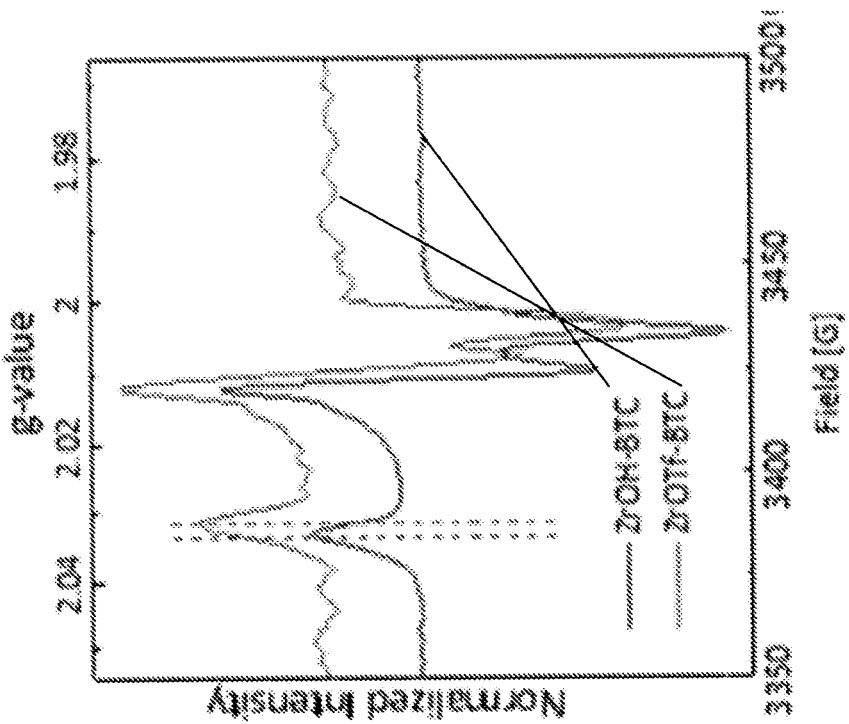
FIG. 6B is a graph showing the electron paramagnetic resonance (EPR) spectra of superoxide-coordinated zirconium triflate-trimesic acid (ZrOTf-BTC-($O_2^{*-}$)) (top) and superoxide-coordinated zirconium hydroxide-trimesic acid (ZrOH-BDC-($O_2^{*-}$)) (bottom), showing different $g_{zz}$ values owing to different Lewis acidity of ZrOTf-BTC and ZrOH-BTC. The EPR spectrum for ZrOTf-BTC is vertically shifted for clarity.

$O_2^{*-}$ probe was generated in situ by the 1 e$^-$ photo-reduction of $O_2$, which readily binds to Lewis acidic Zrcenters by displacing the weakly coordinating triflates to form the EPR-active $Zr(O_2^{*-})$ species.[47] See FIG. 6A. Coordination to Lewis acids significantly shifts the EPR signature of $O_2^{*-}$, especially the $g_{zz}$-tensor that is determined by the energy splitting ($\Delta E$) between the $\pi_x^*$ and $\pi_y^*$ orbitals.[48] ZrOTf-BTC bound $O_2^{*-}$ exhibited a $g_{zz}$ of 2.0310, which corresponds to a $\Delta E$ of 0.99 eV (see FIG. 6B), comparable with the benchmark homogeneous Lewis acid catalyst $Sc(OTf)_3$, which displays a $\Delta E$ of 1.00 eV.[49] The non-triflated ZrOH-BTC has much lower Lewis acidity than ZrOTf-BTC, with a measured $\Delta E$ of 0.90 eV. The Lewis acidity of ZrOTf-BTC is also much higher than the previously reported Zr-fBDC, which has the measured $\Delta E$ of 0.93 eV. The 0.06 eV increase in Lewis acidity makes ZrOTf-BTC a much more active catalyst than Zr-fBDC in Diels-Alder reactions. Furthermore, ZrOTf-BTC has a much higher Lewis acid site density than Zr-fBDC.

NMA fluorescence was also used to probe the Lewis acidity of ZrOTf-BTC. Free NMA has an emission maximum ($\lambda_{max}$) at 433.0 nm. Upon coordination to ZrOTf-BTC, the Zr(NMA)-BTC complex displayed a $\lambda_{max}$ at 471.0 nm. See FIG. 6C. The energy shift of NMA emission is established to be linearly correlated to the Lewis acidity of metal centers.[29,49] Following the empirical equation that was described previously, the $\Delta E$ of ZrOTf-BTC was calculated to be 0.98 eV, which is almost identical to the value measured from superoxide EPR. In comparison, ZrOH-BTC only shifted the NMA emission $\lambda_{max}$ to 467.0 nm, with a calculated $\Delta E$ of 0.89 eV. Identical NMA fluorescence test with homogeneous $Sc(OTf)_3$ also gave a $\Delta E$ of 0.98 eV. Triflation of metal-hydroxides thus provides an effective strategy to enhance MOF Lewis acidity and to generate porous solid acids with Lewis acidity comparable to $Sc(OTf)_3$.

Synthesis and characterization of ZrOTf-BTC@SiO$_2$: Although Lewis acids have broad applications in organic synthesis, little progress has been made in immobilizing Lewis acids for flow synthesis.[50-51] $BF_3$ and $Sc(OTf)_3$ are commonly used to catalyze organic transformations, but they are difficult to incorporate into heterogeneous supports without sacrificing acidity.[52-53] As a result, most flow processes used Lewis acids in stoichiometry, causing significant waste of catalysts and quenching reagents and corrosion of reaction vessels. Owing to their tunable structures and high porosity, MOFs and related organic-inorganic hybrid materials represent an attractive class of solid catalysts for flow catalysis.[54-57] ZrOTf-BTC was studied as an effective fixed-bed Lewis acid catalyst to achieve flow catalysis of a broad scope of reactions.

Figure 7A:
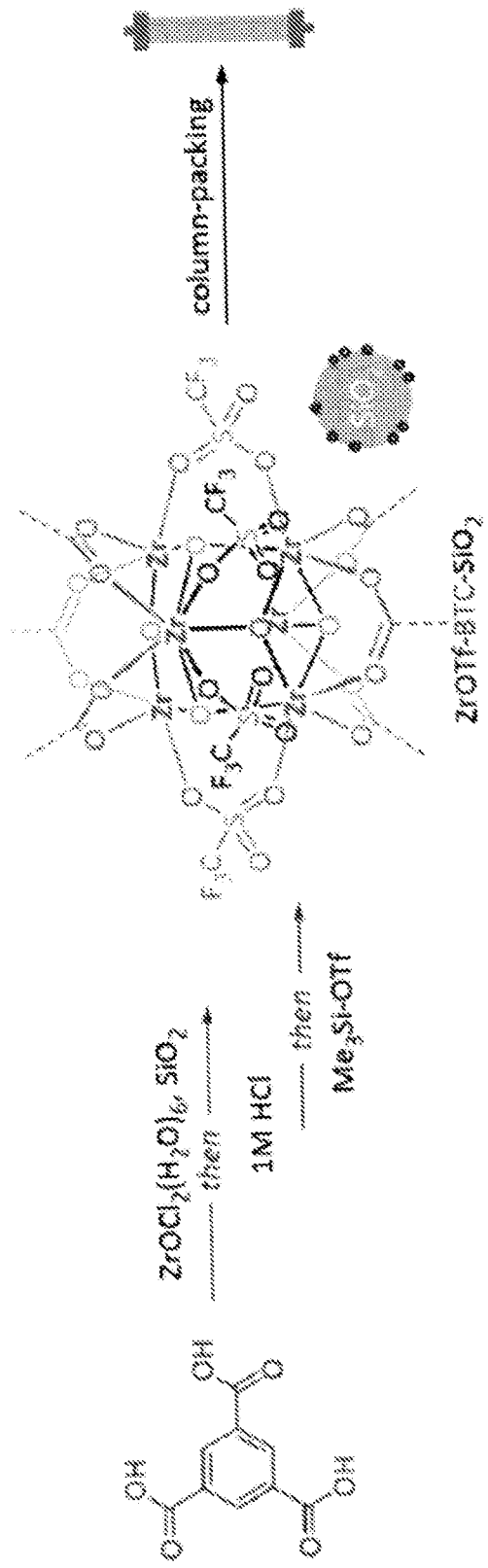
FIG. 7A is a schematic diagram showing the synthesis of zirconium triflate-trimesic acid metal organic framework/silica (ZrOTf-BTC@$SiO_2$) composite and its packing into a column reactor.

Due to the tight packing of MOF particles and the slow substrate diffusion rate through the nano-sized MOF channels, packing pure MOFs into a column can lead to very high column pressure. Growing MOFs into much larger sizes or simply mix the MOF with inert filler can reduce the column pressure, but organic substrates cannot easily access the interiors of such MOF particles due to the increased diffusion barrier. To overcome this, ZrOTf-BTC was directly grown on silica to afford the ZrOTf-BTC@SiO$_2$ composite material. Zr-BTC@SiO$_2$ was first prepared analogously to Zr-BTC except with the addition of 30 weight equiv. of SiO$_2$. See FIG. 7A. Surface silanol groups on SiO$_2$ served as the nucleation sites for the formation of octahedron-shaped Zr-BTC particles of an average dimension of ~50 nm. See FIG. 2. Due to enhanced nucleation on silica surface, the MOF particles in the composite material are smaller than pure MOF particles and are densely packed on silica.

Figure 7C:
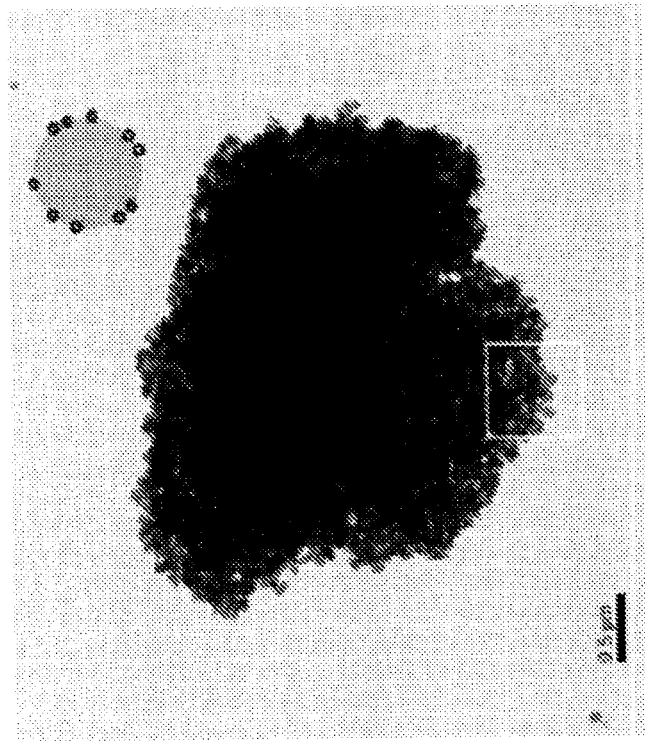
FIG. 7C is a transmission electron microscopy (TEM) image of a zirconium triflate-trimesic acid metal-organic framewok (MOF)/silica (ZrOTf-BTC@$SiO_2$) composite particle. The scale bar in the bottom left corresponds to 0.5 microns (μm). The portion of the particle surrounded by the white box is shown further magnified in FIG. 7D.
Figure 7B:
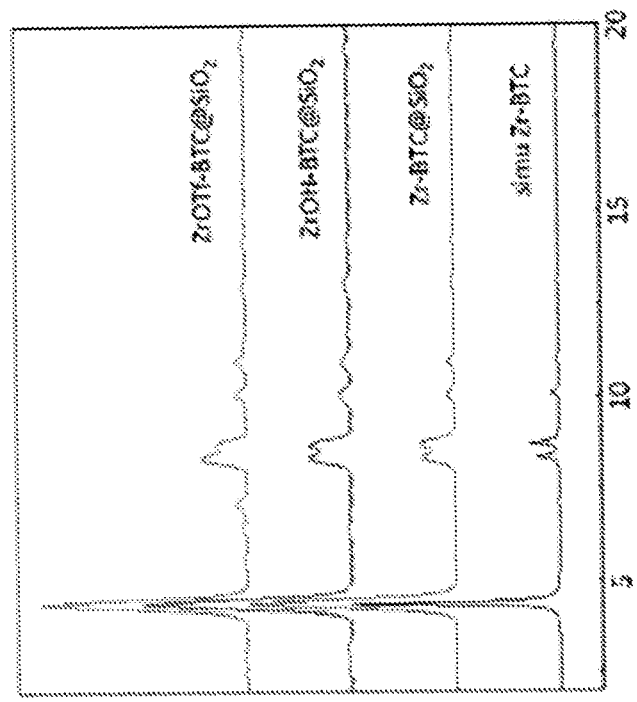
FIG. 7B is a graph showing the powder x-ray diffraction PXRD patterns of zirconium triflate-trimesic acid metal organic framework (MOF)/silica composite (ZrOTf-BTC@$SiO_2$, top), zirconium hydroxide-trimesic acid MOF/silica composite (ZrOH-BTC@$SiO_2$, second from top), and zirconium-trimesic acid MOF/silica composite (Zr-BTC@$SiO_2$, second from bottom) compared to the simulated PXRD pattern for zirconium-trimesic acid MOF (Zr-BTC, bottom), indicating the crystallinity of composite materials.
Figure 7E:
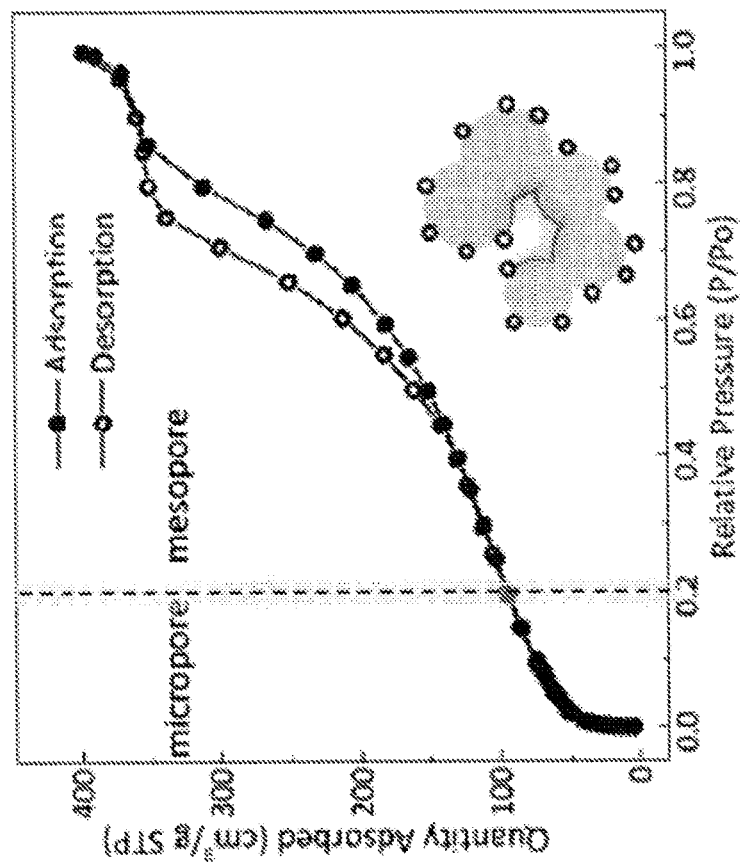
FIG. 7E is a graph showing the nitrogen ($N_2$) sorption isotherms of zirconium triflate-trimesic acid metal-organic framework (MOF)/silica (ZrOTf-BTC@$SiO_2$) composite, which display two steps of sorption in the micropore and mesopore regions. The calculated Brunuaer-Emmett-Teller (BET) surface area is 321 square meters per gram ($m^2/g$) for the ZrOTf-BTC@$SiO_2$.
Figure 7D:
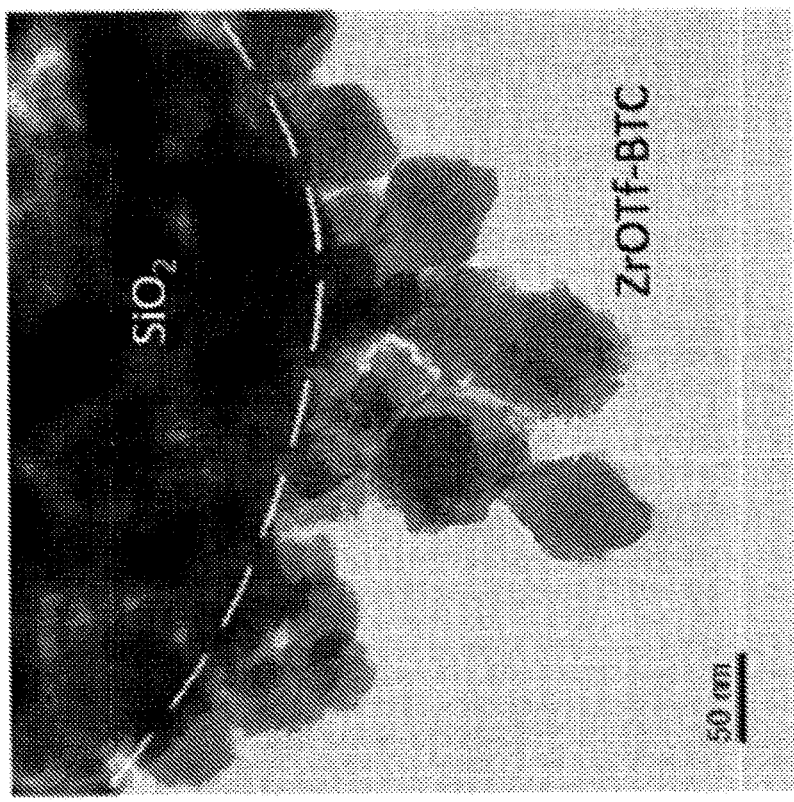
FIG. 7D is a magnified portion of the transmission electron microscopy (TEM) image described in FIG. 7C, showing a surface region of the coated silica particle and the octahedral morphology of metal-organic framework (MOF) particles of about 50 nanometers (nm) in dimensions. The scale bar in the lower left corresponds to 50 nm.
Figure 7F:
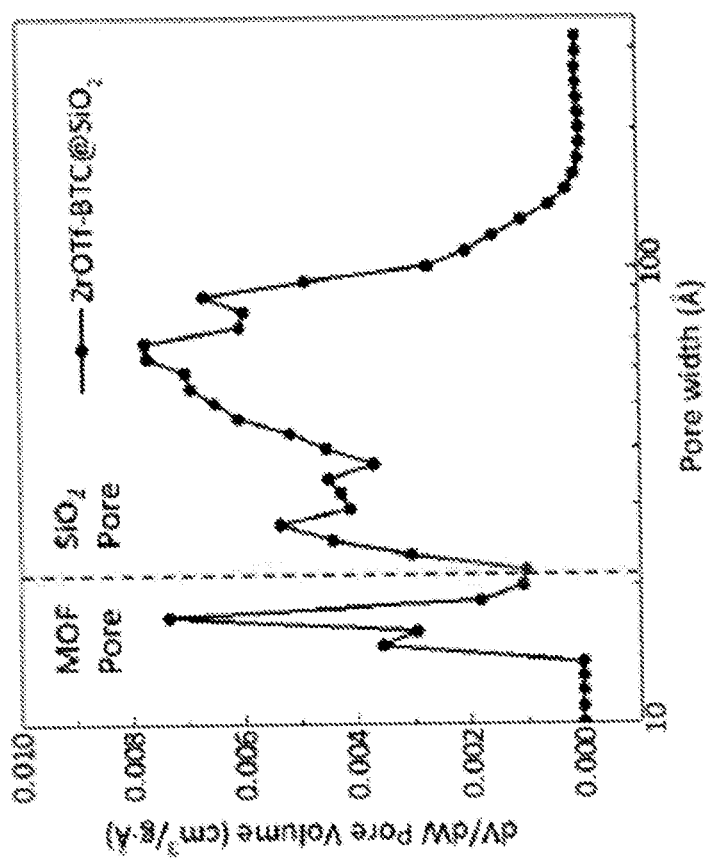
FIG. 7F is a graph of pore size distributions of zirconium triflate-trimesic acid metal-organic framework (MOF)/silica (ZrOTf-BTC@$SiO_2$) composite showing a uniform micropore with a diameter of 16 angstroms (Å) and a series of mesopores in the range of 20-100 Å.

Zr-BTC@SiO$_2$ was treated with 1 M HCl to remove formate capping groups and then triflated with $Me_3SiOTf$ to form ZrOTf-BTC@SiO$_2$ as an off-white powder. TEM imaging showed that ZrOTf-BTC@SiO$_2$ possessed core-shell structures with the MOF particles displaying high crystallinity and octahedral morphology. See FIGS. 7C and 7D. SEM imaging also showed a dense coating of ZrOTf-BTC particles on the silica surface. See FIG. 3. ZrOTf-BTC@SiO$_2$ exhibited the same PXRD pattern as Zr-BTC, indicating that the MOF in the composite maintained the identical structure to pristine MOF. See FIG. 7B. $N_2$ sorption isotherms of ZrOTf-BTC@SiO$_2$ gave a BET surface area of 321 m$^2$/g. The composite material showed a sharp $N_2$ sorption at $P/P_0<0.2$, which can be attributed to micropore filling of ZrOTf-BTC, and a broad adsorption with hysteresis at $P/P_0=0.2-0.9$, which is attributable to mesopore sorption by silica particles. Pore size analysis by NL-DFT indicated the presence of a uniform micropore at 1.6 nm and abroad range of larger pores at 2-10 nm. See FIGS. 7E and 7F. The Zr coordination environment was studied by EXAFS. By using the $\mu_2$-triflate and Zr coordination sphere of $Zr(OTf)_2(\mu_3—O)_2(\mu_3—OH)_2(RCO_2)_2$, the Zr K-edge EXAFS data of ZrOTf-BTC-SiO$_2$ was well fitted with an average Zr-OTf bond distance of 2.217 Å. The Zr active sites in ZrOTf-BTC@SiO$_2$ thus adopts identical coordination environment as those in ZrOTf-BTC. The ZrOTf-BTC@SiO$_2$ powder was slurry-packed with $CH_2Cl_2$ into a stainless-steel column for flow catalysis studies. The amount of ZrOTf-BTC was quantified to be 40 μmol Zr per gram by 1H NMR analysis of the digested material.

ZrOTf-BTC catalyzed Diels-Alder reactions: The Diels-Alder reaction is a very efficient strategy for constructing six-membered ring structures with regioselectivity and stereoselectivity.[16,58] This reaction generally requires the addition of an acid catalyst to reduce reaction temperature and time. Unlike homogeneous Lewis acidic metal complexes, MOF-based Lewis acids offer significant advantages including easy separation from reaction mixtures and catalyst recovery/reuse. Moreover, uniform active sites of MOF catalysts generally afford higher reaction selectivity. For the reaction of 1,4-benzoquinone with cyclohexa-1,3-diene, the cyclization product was obtained in quantitative yield within 1 h at only 1.0 mol % ZrOTf-BTC loading under room temperature. See Table 3, below. No obvious change was observed in the MOF crystallinity by PXRD, whereas only minimum Zr (0.13%) leached into the supernatant after each reaction run by ICP-MS analysis. When the catalyst loading was reduced to 0.1 mol %, the cyclization product was obtained in 76% yield in 10 h, affording a TON of 760. The Diel-Alder reaction is significantly more challenging with electron-rich dienophiles such as α,β-unsaturated ketones and aldehydes due to their much higher LUMO energy. Impressively, at 5.0 mol % catalyst loading, ZrOTf-BTC catalyzed the cyclization of a series of challenging dienophiles, including 3-buten-2-one, methacrolein and crotonaldehyde, with both cyclohexa-1,3-diene and 2,3-dimethylbuta-1,3-diene in high yields.

TABLE 3

Catalyst Evaluation and Substrate Scope of ZrOTf-BTC Catalyzed Diels-Alder Reactions.

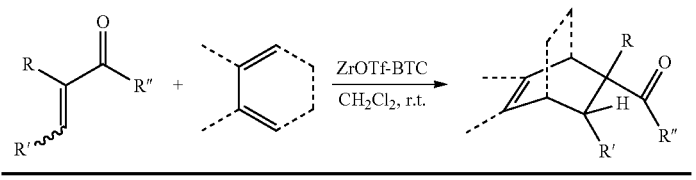

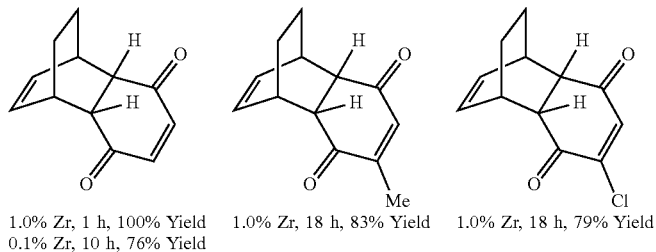

1.0% Zr, 1 h, 100% Yield  1.0% Zr, 18 h, 83% Yield  1.0% Zr, 18 h, 79% Yield
0.1% Zr, 10 h, 76% Yield

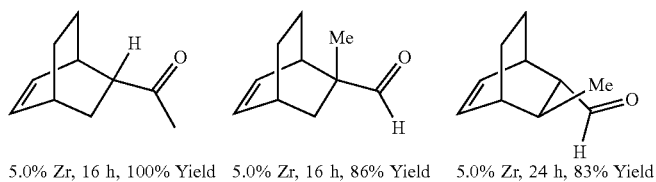

5.0% Zr, 16 h, 100% Yield  5.0% Zr, 16 h, 86% Yield  5.0% Zr, 24 h, 83% Yield

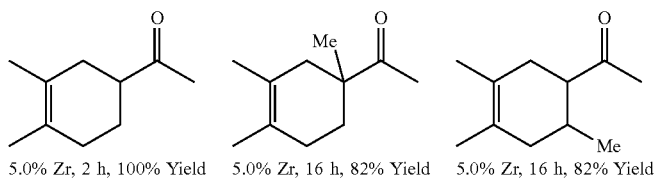

5.0% Zr, 2 h, 100% Yield  5.0% Zr, 16 h, 82% Yield  5.0% Zr, 16 h, 82% Yield

Reaction conditions: dienophile (1 equiv., 1 mmol), diene (1.2 equiv.), ZrOTf-BTC (0.1-5.0 mol %), $CH_2Cl_2$ (4.0 mL), 25° C. Reaction yields were determined by $^1H$ NMR using mesitylene as internal standard.

The heterogeneity of ZrOTf-BTC in the Diels-Alder reaction was confirmed by the "hot filtration" test. After a reaction run, the MOF and supernatant were separated and separately used as catalyst for another reaction run. While the catalytic activity was maintained in the solid MOF, no activity was observed for the supernatant. This "hot filtration" test rules out the possibility of leached Zr salts or soluble Brönsted acids contributing to the catalytic reactivity.

Figure 8:
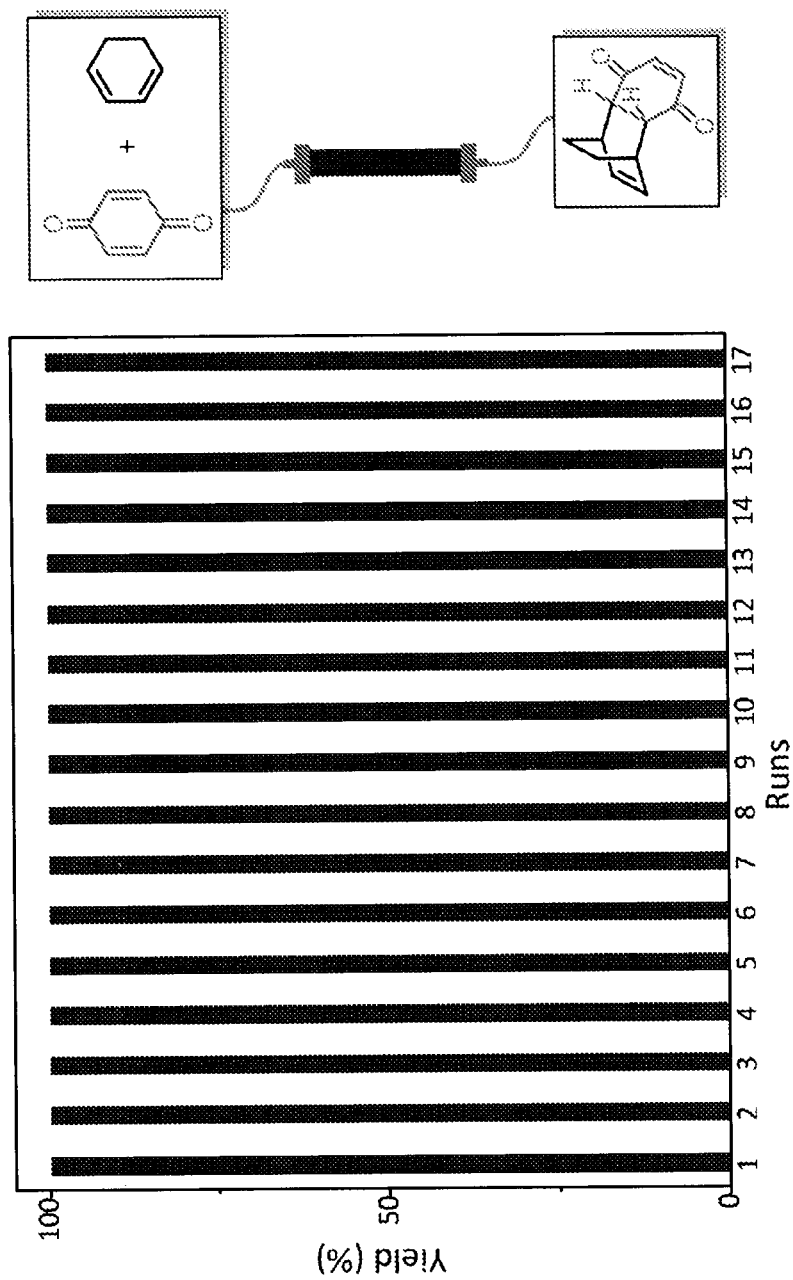
FIG. 8 is a graph showing the yields (as a percent (%) yield) of zirconium triflate-trimesic acid metal-organic framework (MOF)/silica (ZrOTf-BTC@SiO$_2$) composite-catalyzed Diels-Alder reactions in a continuous flow mode over 17 runs.

The Diels-Alder reaction using the ZrOTf-BTC@SiO$_2$ packed column as a continuous flow catalyst was then studied. A CH$_2$Cl$_2$ solution of benzoquinone (limiting reagent) and cyclohexa-1,3-diene (0.5 M) in a molar ratio of 1:1.6 was flowed through the column at a rate of 10 mL·h$^{-1}$ to achieve complete conversion of benzoquinone and to produce the cyclization product in quantitative yield. The turnover frequency (TOF) of the flow process was calculated to be 100 h$^{-1}$. The flow reaction was run for a TON of 1700 in 17 h without a drop in the reaction yield. See FIG. 8.

ZrOTf-BTC catalyzed epoxide ring-opening amination: Epoxides are an important class of industrial chemicals for conversion into a broad range of commodity and fine chemicals.[59-60] For instance, the nucleophilic ring-opening with amines affords β-amino alcohols, which are useful intermediates for organic synthesis.[51,61] Several homogeneous catalysts, including metal triflates and metal halides have been used for this reaction.[62-65] However, very few heterogeneous catalysts have been tested for this reaction to achieve catalyst reuse and flow catalysis. ZrOTf-BTC is a very active catalyst for epoxide ring-opening with anilines. At 5.0 mol % ZrOTf-BTC loading, many different epoxides, including styrene oxide, cyclohexene oxide and cyclopentene oxide, reacted with aniline to form corresponding amino alcohols without heating. See Table 4, below. A broad range of aniline derivatives, including electron-deficient aniline (4-chloroaniline) and electron-rich aniline (2,4,6-trimethylaniline), and sterically hindered secondary anilines (N-methylaniline) can all be used for the ring-opening of epoxides to afford amino alcohols in high yields.

TABLE 4

Catalyst evaluation and substrate scope of ZrOTf-BTC catalyzed epoxide ring-opening reactions.[a]

$$\text{R}\overset{O}{\underset{R'}{\triangle}} + \text{Ar}-\text{NH}_2 \xrightarrow[\text{CH}_2\text{Cl}_2, \text{r.t.}]{\text{ZrOTf-BTC}} \underset{R\;\;\;R'}{\text{HO}\;\;\;\text{HN}-\text{Ar}}$$

| Product | Conditions |
|---|---|
| Ph-CH(OH)-CH₂-NH-Ph | 1% ZrOTf-BTC, 2 h, 64%; 5% ZrOTf-BTC, 2 h, 100% |
| Ph-CH(OH)-CH₂-NH-(4-Cl-C₆H₄) | 1% ZrOTf-BTC, 18 h, 100% |
| Ph-CH(OH)-CH₂-NH-(2,4,6-Me₃-C₆H₂) | 1% ZrOTf-BTC, 18 h, 63% |
| Ph-CH(OH)-CH(Me)-NH-Ph | 1% ZrOTf-BTC, 18 h, 73% |
| trans-cyclohexane-OH,NHPh | 1% ZrOTf-BTC, 2 h, 75%; 5% ZrOTf-BTC, 2 h, 100% |
| trans-cyclohexane-OH,NH-(4-Cl-C₆H₄) | 1% ZrOTf-BTC, 6 h, 100% |
| trans-cyclohexane-OH,NH-(2,4,6-Me₃-C₆H₂) | 1% ZrOTf-BTC, 18 h, 67% |
| trans-cyclohexane-OH,N(Me)Ph | 1% ZrOTf-BTC, 18 h, 81% |
| trans-cyclopentane-OH,NHPh | 1% ZrOTf-BTC, 2 h, 63%; 5% ZrOTf-BTC, 2 h, 93% |

[a]Reaction conditions: epoxides (1 equiv., 1.0 mmol), anilines (1.2 equiv., 1.2 mmol), ZrOTf-BTC (1.0-5.0 mol %), CH₂Cl₂ (4.0 mL), 25° C. Reaction yields were determined by $^1$H NMR using mesitylene as internal standard.

Figure 9:
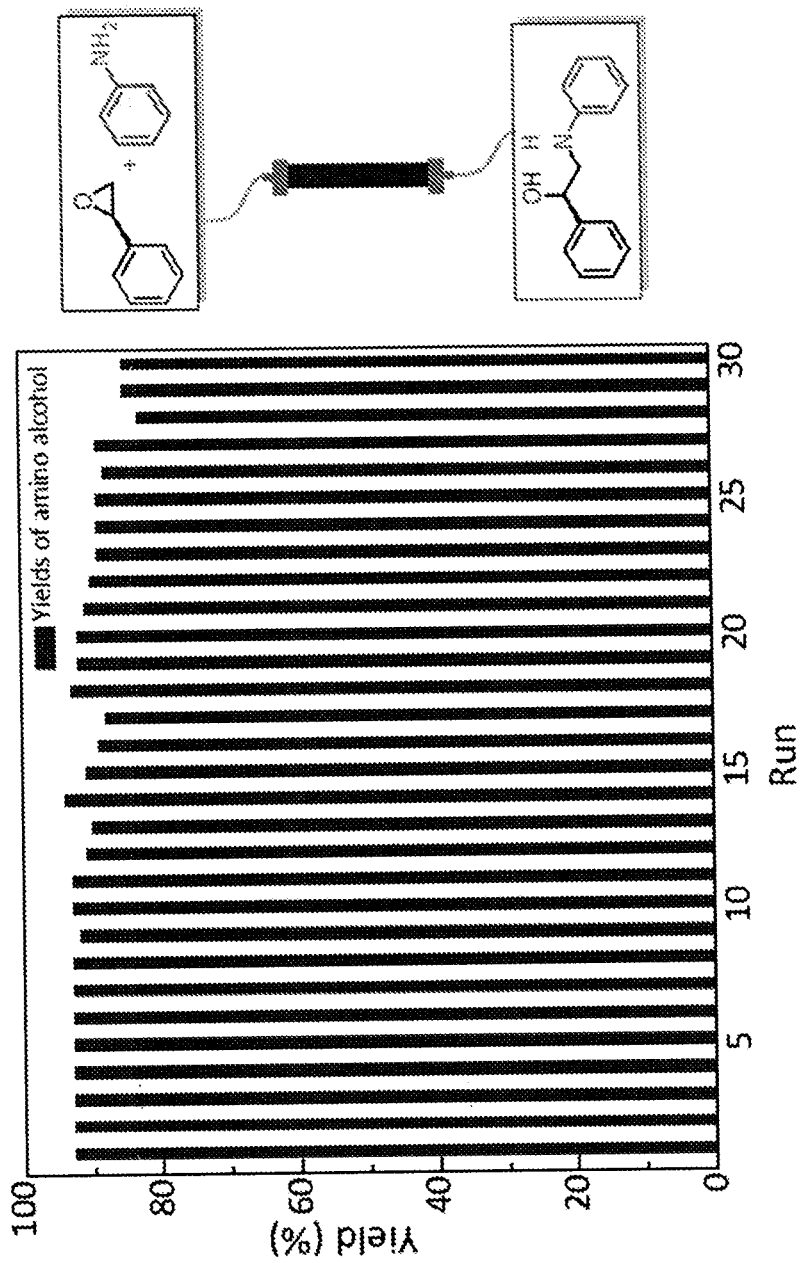
FIG. 9 is a graph showing the yields (percent (%) yield) of zirconium triflate-trimesic acid metal-organic framework (MOF)/silica (ZrOTf-BTC@SiO$_2$) composite-catalyzed epoxide ring-opening reactions with aniline in a continuous flow mode over 30 runs.

The epoxide ring-opening reaction also worked well under flow conditions. Styrene oxide (limiting reagent) and aniline solution in CH$_2$Cl$_2$ (0.5 M) were flowed through ZrOTf-BTC@SiO$_2$ column at a rate of 60 mL·h$^{-1}$ to form the amino alcohol product in 93% yield. High yields (83-93%) of product were consistently obtained in 30 runs to afford a total TON of >2700 in 30 h. See FIG. 9.

ZrOTf-BTC catalyzed Friedel-Crafts acylation reactions: As one of the most convenient and useful strategies for the construction of aryl ketone moieties in a wide range of pharmaceuticals and agricultural chemicals, Friedel-Crafts acylation has drawn continuous research interests.[66] Conventional Lewis acids for Friedel-Crafts acylation include traditional metal halides (e.g., ZnCl$_2$, AlCl$_3$, TiCl$_4$) and metal triflates (e.g., Sc(OTf)$_3$, Hf(OTf)$_4$).[67-69] However, due to the coordination between the Lewis acid and the produced aromatic ketone, stoichiometric amount of metal halides are usually required in these reactions. Furthermore, since the workup procedure typically requires aqueous treatment, the recovery of these homogeneous Lewis acidic metal salts and the generation of large amounts of wastes are long-standing challenges. As a result, significant efforts have been devoted to the development of heterogenous Lewis acid catalyst for Friedel-Crafts acylation.

At 1.0 mol % of loading, ZrOTf-BTC catalyzed Friedel-Crafts acylation between 2-methoxynaphthalene and neat acetic anhydride in 2 h at room temperature to afford 1-acetyl-2-methoxynaphthalene in 98% isolated yield. See Table 5, below. This level of activity is much higher than those of most Lewis acid catalysts including homogeneous metal triflates and solid acid catalysts. Several substituted arenes, including anisole, dimethoxybenzene, mesitylene, and benzofuran, underwent acylation in the presence of 1-5 mol % of ZrOTf-BTC at room temperature to afford desired products in 63-83% yields. Furthermore, 5.0 mol % ZrOTf-BTC catalyzed Friedel-Crafts acylation with benzoic anhydride in CH$_2$Cl$_2$ to afford 1-benzoyl-2-methoxynaphthalene in 81% yield.

TABLE 5

ZrOTf-BTC catalyzed Friedel-Crafts acylation reactions.[a]

R = Me, 1.0% Zr, 2 h, 98%
R = Ph, 5.0% Zr, 18 h, 81%

R = Me, 1.0% Zr, 18 h, 83%
R = Ph, 5.0% Zr, 18 h, 57%

5.0% Zr, 18 h, 67%

2.0% Zr, 18 h, 63%

2.0% Zr, 48 h, 65%

5.0% Zr, 18 h, 83%

[a]Reaction conditions: arene (1 equiv., 1.0 mmol), acetic anhydride (1.0 mL, excess) or benzoic anhydride (3 equiv., 3.0 mmol, in 2.0 mL $CH_2Cl_2$), ZrOTf-BTC (1.0-5.0 mol %), 25° C. Isolated yields are listed.

Figure 10:
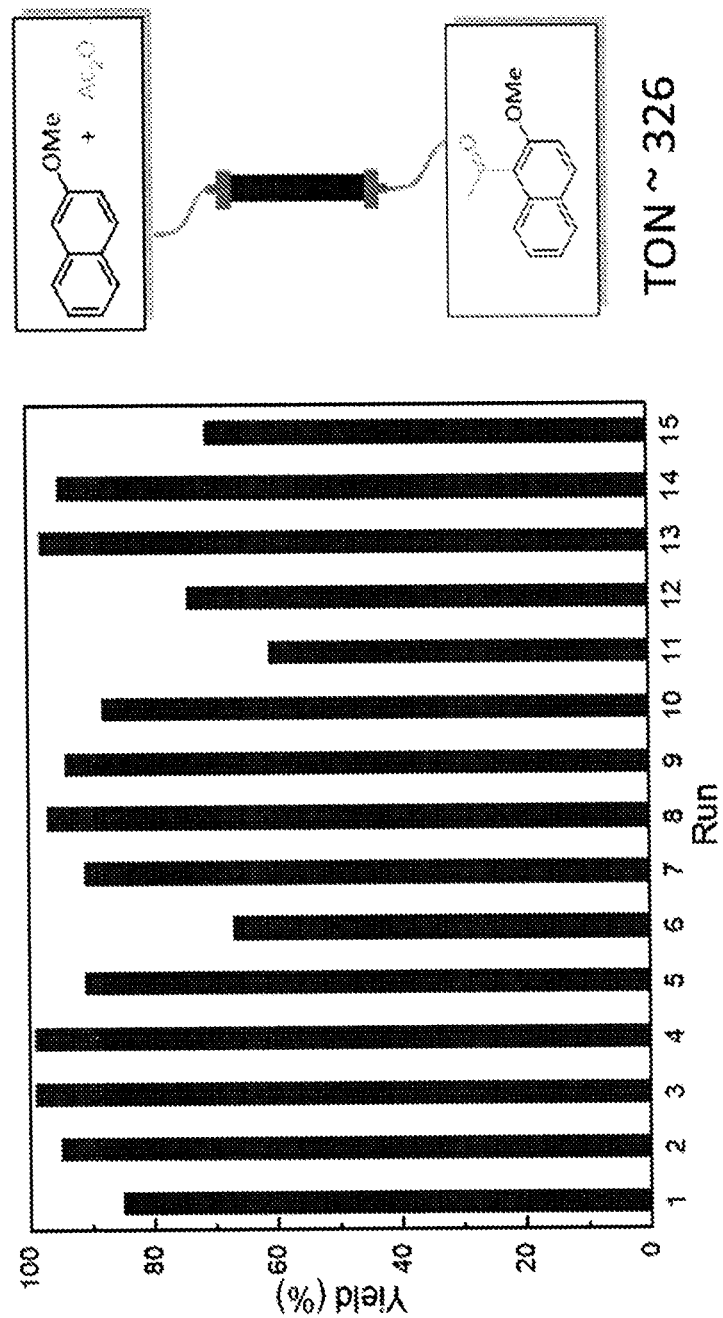
FIG. 10 is a graph showing the yields (as a percent (%) yield) of zirconium triflate-trimesic acid metal-organic framework (MOF)/silica (ZrOTf-BTC@SiO$_2$) composite-catalyzed Friedel-Crafts acylation reactions between 2-methoxynaphthalene and acetic anhydride in the continuous flow mode.

The catalytic performance of Friedel-Crafts acylation was also tested in the continuous flow mode. When a solution of 2-methoxynaphthalene (0.05 M) in $Ac_2O/CH_2Cl_2$ (1:4, v/v) was flowed through ZrOTf-BTC@$SiO_2$ column at a rate of 30 mL·$h^{-1}$, 1-acetyl-2-methoxynaphthalene was formed as the desired product in excellent yields (85-99%) in the first 5 runs (5 mL solution per run). The yield dropped to 65% in the six run but the catalytic performance was restored by simply washing the column with a $CH_3CN/CH_2Cl_2$ (1:9, v/v) solution. 15 consecutive runs afforded a total TON of 326 and a TOF of 130 $h^{-1}$ (the column was washed after the $6^{th}$ and $11^{th}$ run). The catalyst performance in the flow mode significantly outperformed that of the batch mode. See FIG. 10.

ZrOTf-BTC catalyzed alkene hydroalkoxylation reactions: ZrOTf-BTC is also a highly active catalyst for alkene hydroalkoxylation reactions. Oxygen-containing cyclic compounds are abundant in polyether antibiotics and other biologically active natural products as well as in chemical feedstocks.[70-71] The addition of alcohols across C=C bonds is the most straightforward synthetic route to cyclic ethers.[72-73] This reaction pathway is widely adopted by biological systems to synthesize cyclic ether-containing natural products.[74-75] Some homogeneous catalysts are effective for this reaction, but many of them require activated alkenes (e.g. alkenes, dienes, and Michael acceptors).[76-79] This is believed to be the first example of MOF-catalyzed alkene hydroalkoxylation using highly acidic ZrOTf-BTC.

For the cyclization of 4-penten-1-ol, 2.0 mol % of ZrOTf-BTC afforded 2-methyltetrahydrofuran in quantitative yield after heating at 135° C. under inert atmosphere for 18 h. See Table 6, below. 5-hexen-1-ol was also hydroalkoxylated in 91% yield at 4.0 mol % ZrOTf-BTC to afford 2-methyltetrahydropyran and 2-ethyltetrahydrofuran in a 3:1 ratio. Besides aliphatic alcohols, alkene substrates containing phenol groups such as 2-allylphenol and 2-allyl-6-methylphenol were also catalytically cyclized with ZrOTf-BTC at a lower temperature of 100° C. Alkene-containing carboxylic acids such as pent-4-enoic acid and hex-5-enoic acid were also hydroalkoxylated to form corresponding lactones in excellent yields (91-95%) at 1.0 mol % catalyst loading.

TABLE 6

ZrOTf-BTC catalyzed intramolecular alkene hydroalkoxylation.

2% Zr, 135° C., 100%

4% Zr, 135° C., 93% (1:3)

TABLE 6-continued

ZrOTf-BTC catalyzed intramolecular alkene hydroalkoxylation.

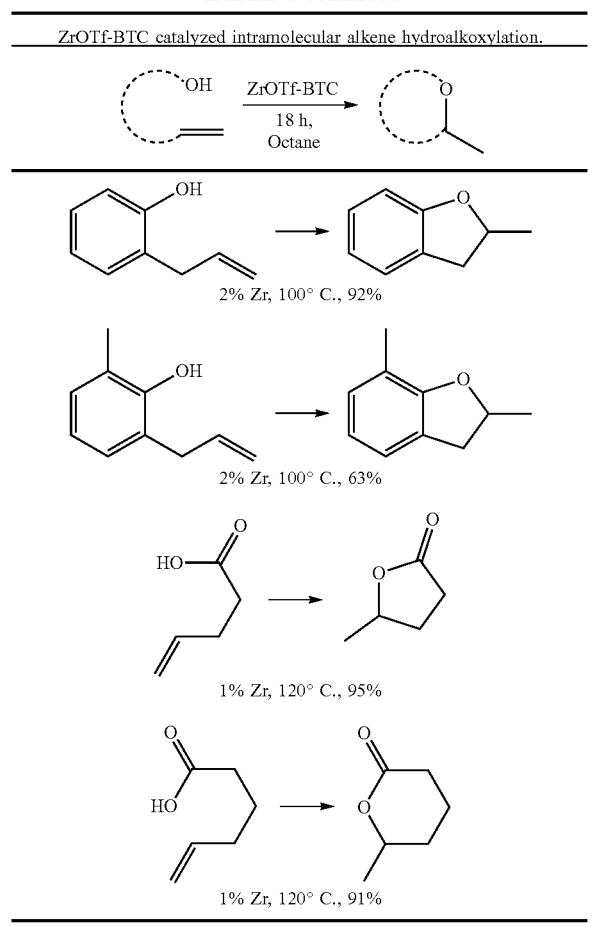

Reaction conditions: substrate (1.0 mmol), ZrOTf-BTC (1.0-4.0 mol %), octane (2.0 mL), 100-135° C., 18 h, inert atmosphere. Reaction yields were determined by ¹H NMR using mesitylene as internal standard.

Figure 11:
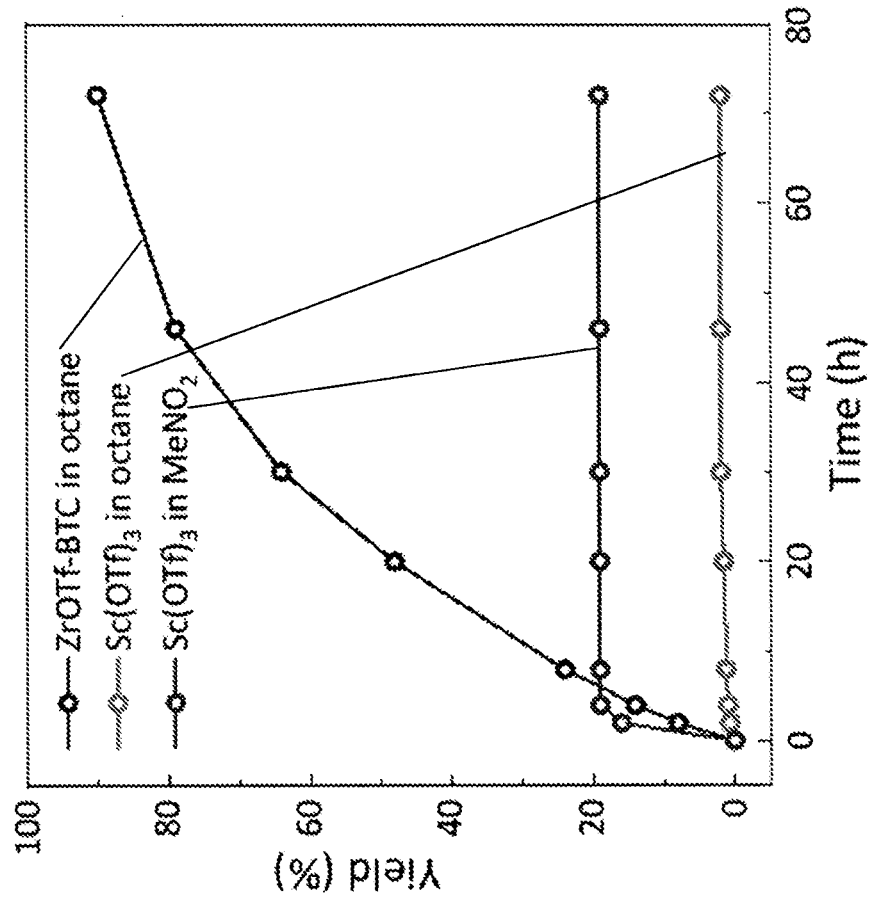
FIG. 11 is a graph comparing the catalytic performance of zirconium triflate-trimesic acid (ZrOTf-BTC) and scandium triflate (Sc(OTf)$_3$) for alkene hydroalkoxylation. The catalyst loadings are both 0.2 mole percent (mol %).
Figure 11:
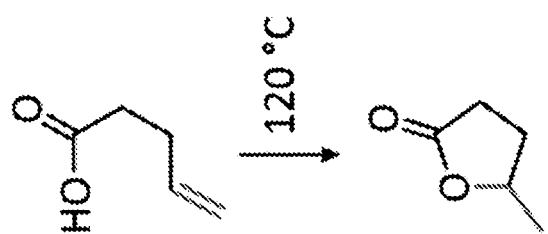

To further demonstrate the advantage of ZrOTf-BTC over conventional Sc(OTf)$_3$ in catalyzing alkene hydroalkoxylation reactions, catalytic hydroalkoxylation of pent-4-enoic acid was conducted at 0.2 mol % loading of ZrOTf-BTC and Sc(OTf)$_3$. As shown in FIG. 11, ZrOTf-BTC catalyzed the hydroalkoxylation of pent-4-enoic acid in octane to afford 90% of γ-valerolactone in 72 h, while very little product was detected in the presence of Sc(OTf)$_3$ under the same condition. The lack of catalytic activity of Sc(OTf)$_3$ is likely due to its poor solubility in non-polar octane. Changing the solvent to polar MeNO$_2$ afforded 2-methyltetrahydrofuran in 20% yield at 0.2 mol % Sc(OTf)$_3$ in 5 h. However, no further substrate conversion was observed beyond 5 h, suggesting the deactivation of Sc(OTf)$_3$ in polar solvent at elevated temperature. ZrOTf-BTC thus shows much longer lifetime than Sc(OTf)$_3$ in alkene hydroalkoxylation. Additionally, as a heterogeneous catalyst, ZrOTf-BTC was easily recovered from the reaction mixture via centrifugation and reused at least 5 times without significant activity decrease. ZrOTf-BTC thus shows significant advantage over traditional homogeneous Lewis acid catalysts in catalytic activity, lifetime, and catalyst recovery and reuse.

Summary: A strongly Lewis acidic MOF, ZrOTf-BTC, was prepared through two-step SBU transformations of MOF-808. The Lewis acidity of the Zr-triflate active site was quantified through spectroscopic methods to be comparable to the homogeneous benchmark Sc(OTf)$_3$. ZrOTf-BTC was shown to be a highly active solid Lewis acid catalyst for a broad range of organic transformations, including Diels-Alder reaction, epoxide ring-opening, Friedel-Crafts acylation, and alkene hydroalkoxylation reactions. The catalytic performance of ZrOTf-BTC is superior over Sc(OTf)$_3$ in terms of catalyst activity, lifetime, and reusability. ZrOTf-BTC@SiO$_2$ composite was developed for continuous flow catalysis. ZrOTf-BTC@SiO$_2$ displayed exceptionally high turnover numbers (TONs) of 1600 for Diels-Alder reaction, 2700 for epoxide ring-opening reaction, and 326 for Friedel-Crafts acylation under flow conditions. Thus, the creation of strongly Lewis acidic sites in MOFs via triflation and the utility of MOF@SiO$_2$ composite in continuous flow catalysis of important organic transformations has been demonstrated.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

[1] Moulton et al. From molecules to crystal engineering: supramolecular isomerism and polymorphism in network solids. *Chem. Rev.* 2001, 101, 1629-1658.

[2] Evans et al. Crystal Engineering of NLO Materials Based on Metal-Organic Coordination Networks. *Acc. Chem. Res.* 2002, 35, 511-522.

[3] Lan et al. A luminescent microporous metal-organic framework for the fast and reversible detection of high explosives. *Angew. Chem. Int. Ed. Engl.* 2009, 48, 2334-2338.

[4] Uemura et al. Polymerization reactions in porous coordination polymers. *Chem. Rev.* 2009, 38(5), 1-9.

[5] Das et al. Functional mixed metal-organic frameworks with metalloligands. *Angew. Chem. Int. Ed. Engl.* 2011, 50, 10510-10520.

[6] Wiers et al. A solid lithium electrolyte via addition of lithium isopropoxide to a metal-organic framework with open metal sites. *J. Am. Chem. Soc.* 2011, 133(37), 14522-14525.

[7] Kreno et al. Metal Organic Framework Materials as Chemical Sensors. *Chem. Rev.* 2012, 112, 1105-1125.

[8] Li et al. Metal-organic frameworks for separations. *Chem. Rev.* 2012, 112, 869-932.

[9] Furukawa et al. The Chemistry and Applications of Metal-Organic Frameworks. *Science* 2013, 341, 974-986.

[10] Shustova et al. Selective turn-on ammonia sensing enabled by high-temperature fluorescence in metal-organic frameworks with open metal sites. *J. Am. Chem. Soc.* 2013, 135, 13326-13329.

[11] Kesanli et al. Chiral porous coordination networks: rational design and applications in enantioselective processes. *Coord. Chem. Rev.* 2003, 246, 305-326.

[12] Yamamoto, H., *Lewis acids in organic synthesis*. Wiley-VCH Verlag GmbH: 2000; Vol. 1.

[13] Corma, A.; Garcia, H. Lewis Acids as Catalysts in Oxidation Reactions: From Homogeneous to Heterogeneous Systems. *Chem. Rev.* 2002, 102 (10), 3837-3892.

[14] Corma, A.; Garcia, H. Lewis Acids: From Conventional Homogeneous to Green Homogeneous and Heterogeneous Catalysis. *Chem. Rev.* 2003, 103 (11), 4307-4366.

[15] Houk, K. N.; Strozier, R. W. Lewis acid catalysis of Diels-Alder reactions. *J. Am. Chem. Soc.* 1973, 95 (12), 4094-4096.

[16] Nicolaou, K. C.; Snyder, S. A.; Montagnon, T.; Vassilikogiannakis, G. The Diels-Alder Reaction in Total Synthesis. *Angew. Chem. Int. Ed.* 2002, 41 (10), 1668-1698.

[17] Mori, K.; Hara, T.; Mizugaki, T.; Ebitani, K.; Kaneda, K. Hydroxyapatite-Bound Cationic Ruthenium Complexes as Novel Heterogeneous Lewis Acid Catalysts for Diels-Alder and Aldol Reactions. *J. Am. Chem. Soc.* 2003, 125 (38), 11460-11461.

[18] Corma, A.; Renz, M. Sn-Beta zeolite as diastereoselective water-resistant heterogeneous Lewis-acid catalyst for carbon-carbon bond formation in the intramolecular carbonyl-ene reaction. *Chem. Commun.* 2004, (5), 550-551.

[19] Nakajima, K.; Baba, Y.; Noma, R.; Kitano, M.; N. Kondo, J.; Hayashi, S.; Hara, M. $Nb_2O_5.nH_2O$ as a Heterogeneous Catalyst with Water-Tolerant Lewis Acid Sites. *J. Am. Chem. Soc.* 2011, 133 (12), 4224-4227.

[20] Blackwell, J. A.; Carr, P. W. A Chromatographic Study of the Lewis Acid-Base Chemistry of Zirconia Surfaces. *J. Liq. Chromatogr.* 1991, 14 (15), 2875-2889.

[21] Lunsford, J. H.; Sang, H.; Campbell, S. M.; Liang, C.-H.; Anthony, R. G. An NMR study of acid sites on sulfated-zirconia catalysts using trimethylphosphine as a probe. *Catal. Lett.* 1994, 27 (3), 305-314.

[22] Lee, J.; Farha, O. K.; Roberts, J.; Scheidt, K. A.; Nguyen, S. T.; Hupp, J. T. Metal-organic framework materials as catalysts. *Chem. Soc. Rev.* 2009, 38 (5), 1450-1459.

[23] Comito, R. J.; Fritzsching, K. J.; Sundell, B. J.; Schmidt-Rohr, K.; Dincă, M. Single-Site Heterogeneous Catalysts for Olefin Polymerization Enabled by Cation Exchange in a Metal-Organic Framework. *J. Am. Chem. Soc.* 2016, 138 (32), 10232-10237.

[24] Ji, P.; Feng, X.; Veroneau, S. S.; Song, Y.; Lin, W. Trivalent Zirconium and Hafnium Metal-Organic Frameworks for Catalytic 1,4-Dearomative Additions of Pyridines and Quinolines. *J. Am. Chem. Soc.* 2017, 139 (44), 15600-15603.

[25] Drake, T.; Ji, P.; Lin, W. Site Isolation in Metal-Organic Frameworks Enables Novel Transition Metal Catalysis. *Acc. Chem. Res.* 2018, 51 (9), 2129-2138.

[26] Feng, X.; Song, Y.; Li, Z.; Kaufmann, M.; Pi, Y.; Chen, J. S.; Xu, Z.; Li, Z.; Wang, C.; Lin, W. Metal-Organic Framework Stabilizes a Low-Coordinate Iridium Complex for Catalytic Methane Borylation. *J. Am. Chem. Soc.* 2019, DOI: 10.1021/jacs.1029b04285.

[27] He, W. L.; Zhao, M.; Wu, C. D. A Versatile Metalloporphyrinic Framework Platform for Highly Efficient Bioinspired, Photo- and Asymmetric Catalysis. *Angew. Chem. Int. Ed.* 2019, 58 (1), 168-172.

[28] Vermoortele, F.; Vandichel, M.; Van de Voorde, B.; Ameloot, R.; Waroquier, M.; Van Speybroeck, V.; De Vos, D. E. Electronic Effects of Linker Substitution on Lewis Acid Catalysis with Metal-Organic Frameworks. *Angew. Chem. Int. Ed.* 2012, 51 (20), 4887-4890.

[29] Ji, P.; Drake, T.; Murakami, A.; Oliveres, P.; Skone, J. H.; Lin, W. Tuning Lewis Acidity of Metal-Organic Frameworks via Perfluorination of Bridging Ligands: Spectroscopic, Theoretical, and Catalytic Studies. *J. Am. Chem. Soc.* 2018, 140 (33), 10553-10561.

[30] Mondloch, J. E.; Katz, M. J.; Isley Iii, W. C.; Ghosh, P.; Liao, P.; Bury, W.; Wagner, G. W.; Hall, M. G.; DeCoste, J. B.; Peterson, G. W.; Snurr, R. Q.; Cramer, C. J.; Hupp, J. T.; Farha, O. K. Destruction of chemical warfare agents using metal-organic frameworks. *Nat. Mater.* 2015, 14, 512.

[31] Moon, S.-Y.; Liu, Y.; Hupp, J. T.; Farha, O. K. Instantaneous Hydrolysis of Nerve-Agent Simulants with a Six-Connected Zirconium-Based Metal-Organic Framework. *Angew. Chem. Int. Ed.* 2015, 54 (23), 6795-6799.

[32] Yang, D.; Ortuño, M. A.; Bernales, V.; Cramer, C. J.; Gagliardi, L.; Gates, B. C. Structure and Dynamics of Zr6O8 Metal-Organic Framework Node Surfaces Probed with Ethanol Dehydration as a Catalytic Test Reaction. *J. Am. Chem. Soc.* 2018, 140 (10), 3751-3759.

[33] Horike, S.; Dincă, M.; Tamaki, K.; Long, J. R. Size-Selective Lewis Acid Catalysis in a Microporous Metal-Organic Framework with Exposed $Mn^{2+}$ Coordination Sites. *J. Am. Chem. Soc.* 2008, 130 (18), 5854-5855.

[34] Senkovska, I.; Hoffmann, F.; Fröba, M.; Getzschmann, J.; Böhlmann, W.; Kaskel, S. New highly porous aluminium based metal-organic frameworks: Al(OH)(ndc) (ndc=2,6-naphthalene dicarboxylate) and Al(OH)(bpdc) (bpdc=4,4'-biphenyl dicarboxylate). *Microporous Mesoporous Mater.* 2009, 122 (1), 93-98.

[35] Guillerm, V.; Xu, H.; Albalad, J.; Imaz, I.; Maspoch, D. Postsynthetic Selective Ligand Cleavage by Solid-Gas Phase Ozonolysis Fuses Micropores into Mesopores in Metal-Organic Frameworks. *J. Am. Chem. Soc.* 2018, 140 (44), 15022-15030.

[36] Alonso, D. M.; Wettstein, S. G.; Dumesic, J. A. Bimetallic catalysts for upgrading of biomass to fuels and chemicals. *Chem. Soc. Rev.* 2012, 41 (24), 8075-8098.

[37] Li, Z.; Assary, R. S.; Atesin, A. C.; Curtiss, L. A.; Marks, T. J. Rapid Ether and Alcohol C—O Bond Hydrogenolysis Catalyzed by Tandem High-Valent Metal Triflate+Supported Pd Catalysts. *J. Am. Chem. Soc.* 2014, 136 (1), 104-107.

[38] Lohr, T. L.; Li, Z.; Assary, R. S.; Curtiss, L. A.; Marks, T. J. Thermodynamically Leveraged Tandem Catalysis for Ester RC(O)O—R' Bond Hydrogenolysis. Scope and Mechanism. *ACS Catalysis* 2015, 5 (6), 3675-3679.

[39] Zhao, C.; Kou, Y.; Lemonidou, A. A.; Li, X.; Lercher, J. A. Highly Selective Catalytic Conversion of Phenolic Bio-Oil to Alkanes. *Angew. Chem. Int. Ed.* 2009, 48 (22), 3987-3990.

[40] Ji, P.; Solomon, J. B.; Lin, Z.; Johnson, A.; Jordan, R. F.; Lin, W. Transformation of Metal-Organic Framework Secondary Building Units into Hexanuclear Zr-Alkyl Catalysts for Ethylene Polymerization. *J. Am. Chem. Soc.* 2017, 139 (33), 11325-11328.

[41] Yutaka, O.; Miyoko, K. One-electron Reduction of 1-Benzyl-3-carbamoylpyridinium as a NAD+Model. *Bull. Chem. Soc. Jpn.* 1979, 52 (9), 2674-2677.

[42] Ohkubo, K.; Menon, S. C.; Orita, A.; Otera, J.; Fukuzumi, S. Quantitative Evaluation of Lewis Acidity of Metal Ions with Different Ligands and Counterions in Relation to the Promoting Effects of Lewis Acids on Electron Transfer Reduction of Oxygen. *J. Org. Chem.* 2003, 68 (12), 4720-4726.

[43] Sobańska, K.; Krasowska, A.; Mazur, T.; Podolska-Serafin, K.; Pietrzyk, P.; Sojka, Z. Diagnostic Features of EPR Spectra of Superoxide Intermediates on Catalytic Surfaces and Molecular Interpretation of Their g and A Tensors. *Top. Catal.* 2015, 58 (12), 796-810.

[44] Furukawa, H.; Gándara, F.; Zhang, Y.-B.; Jiang, J.; Queen, W. L.; Hudson, M. R.; Yaghi, O. M. Water Adsorption in Porous Metal-Organic Frameworks and Related Materials. *J. Am. Chem. Soc.* 2014, 136 (11), 4369-4381.

[45] Herrmann, H.; Gehrmann, T.; Wadepohl, H.; Gade, L. H. Zirconium and hafnium (1-pyridinio)imido complexes: functionalized terminal hydrazinediido analogues. *Dalton Trans.* 2008, (44), 6231-6241.

[46] Kristian, K. E.; limura, M.; Cummings, S. A.; Norton, J. R.; Janak, K. E.; Pang, K. Mechanism of the Reaction of Alkynes with a "Constrained Geometry" Zirconaaziridine. PMe3 Dissociates More Rapidly from the Constrained Geometry Complex than from its Cp2 Analogue. *Organometallics* 2009, 28 (2), 493-498.

[47] Fukuzumi, S.; Patz, M.; Suenobu, T.; Kuwahara, Y.; Itoh, S. ESR Spectra of Superoxide Anion-Scandium Complexes Detectable in Fluid Solution. *J. Am. Chem. Soc.* 1999, 121 (7), 1605-1606.

[48] Sobanska, K.; Krasowska, A.; Mazur, T.; Podolska-Serafin, K.; Pietrzyk, P.; Sojka, Z. Diagnostic Features of EPR Spectra of Superoxide Intermediates on Catalytic Surfaces and Molecular Interpretation of Their g and A Tensors. *Top. Catal.* 2015, 58 (12), 796-810.

[49] Ohkubo, K.; Menon, S. C.; Orita, A.; Otera, J.; Fukuzumi, S. Quantitative Evaluation of Lewis Acidity of Metal Ions with Different Ligands and Counterions in Relation to the Promoting Effects of Lewis Acids on Electron Transfer Reduction of Oxygen. *J. Org. Chem.* 2003, 68 (12), 4720-4726.

[50] Román-Leshkov, Y.; Davis, M. E. Activation of Carbonyl-Containing Molecules with Solid Lewis Acids in Aqueous Media. *ACS Catal.* 2011, 1 (11), 1566-1580.

[51] Tang, B.; Song, W.-C.; Li, S.-Y.; Yang, E.-C.; Zhao, X.-J. Post-synthesis of Zr-MOR as a robust solid acid catalyst for the ring-opening aminolysis of epoxides. *New J. Chem.* 2018, 42 (16), 13503-13511.

[52] Kobayashi, S.; Nagayama, S. A Microencapsulated Lewis Acid. A New Type of Polymer-Supported Lewis Acid Catalyst of Wide Utility in Organic Synthesis. *J. Am. Chem. Soc.* 1998, 120 (12), 2985-2986.

[53] Tanaka, K.; Fukase, K. Acid-mediated reactions under microfluidic conditions: A new strategy for practical synthesis of biofunctional natural products. *Beilstein J. Org. Chem.* 2009, 5, 40.

[54] Zeng, L.; Liao, P.; Liu, H.; Liu, L.; Liang, Z.; Zhang, J.; Chen, L.; Su, C.-Y. Impregnation of metal ions into porphyrin-based imine gels to modulate guest uptake and to assemble a catalytic microfluidic reactor. *J. Mater. Chem. A* 2016, 4 (21), 8328-8336.

[55] Chen, X.; Jiang, H.; Hou, B.; Gong, W.; Liu, Y.; Cui, Y. Boosting Chemical Stability, Catalytic Activity, and Enantioselectivity of Metal-Organic Frameworks for Batch and Flow Reactions. *J. Am. Chem. Soc.* 2017, 139 (38), 13476-13482.

[56] Park, H. D.; Dince, M.; Román-Leshkov, Y. Continuous-Flow Production of Succinic Anhydrides via Catalytic β-Lactone Carbonylation by Co(CO)4cCr-MIL-101. *J. Am. Chem. Soc.* 2018, 140 (34), 10669-10672.

[57] Zhang, J.; Chen, J.; Peng, S.; Peng, S.; Zhang, Z.; Tong, Y.; Miller, P. W.; Yan, X.-P. Emerging porous materials in confined spaces: from chromatographic applications to flow chemistry. *Chem. Soc. Rev.* 2019, 48 (9), 2566-2595. *J. Am. Chem. Soc.* 1952, 74 (17), 4223-4251.

[58] Gorzynski Smith, J. Synthetically Useful Reactions of Epoxides. *Synthesis* 1984, 1984 (08), 629-656.

[59] Jacobsen, E. N. Asymmetric Catalysis of Epoxide Ring-Opening Reactions. *Acc. Chem. Res.* 2000, 33 (6), 421-431.

[61] Ager, D. J.; Prakash, I.; Schaad, D. R. 1,2-Amino Alcohols and Their Heterocyclic Derivatives as Chiral Auxiliaries in Asymmetric Synthesis. *Chem. Rev.* 1996, 96 (2), 835-876.

[62] Chakraborti, A. K.; Kondaskar, A. ZrCl4 as a new and efficient catalyst for the opening of epoxide rings by amines. *Tetrahedron Lett.* 2003, 44 (45), 8315-8319.

[63] Kamal, A.; Ramu, R.; Azhar, M. A.; Khanna, G. B. R. Copper(II) tetrafluoroborate-catalyzed ring-opening of epoxides by amines. *Tetrahedron Lett.* 2005, 46 (15), 2675-2677.

[64] Procopio, A.; Gaspari, M.; Nardi, M.; Oliverio, M.; Rosati, O. Highly efficient and versatile chemoselective addition of amines to epoxides in water catalyzed by erbium(III) triflate. *Tetrahedron Lett.* 2008, 49 (14), 2289-2293.

[65] Shinde, S. S.; Said, M. S.; Surwase, T. B.; Kumar, P. Mild regiospecific alcoholysis and aminolysis of epoxides catalyzed by zirconium(IV) oxynitrate. *Tetrahedron Lett.* 2015, 56 (43), 5916-5919.

[66] Sartori, G.; Maggi, R., *Advances in Friedel-Crafts acylation reactions: catalytic and green processes.* CRC Press: 2009.

[67] Iwao, H.; Mitsuhiro, M.; Shu, K. Hafnium(IV) Trifluoromethanesulfonate, An Efficient Catalyst for the Friedel-Crafts Acylation and Alkylation Reactions. *Bull. Chem. Soc. Jpn.* 1995, 68 (7), 2053-2060.

[68] Atsushi, K.; Shuichi, M.; Jun-ichi, M.; Takehiro, T.; Shu, K. Friedel-Crafts Reactions Catalyzed by Rare Earth Metal Trifluoromethanesulfonates. *Bull. Chem. Soc. Jpn.* 2000, 73 (10), 2325-2333.

[69] Dzudza, A.; Marks, T. J. Lanthanide Triflate-Catalyzed Arene Acylation. Relation to Classical Friedel-Crafts Acylation. *J. Org. Chem.* 2008, 73 (11), 4004-4016.

[70] Elliott, M. C. Saturated oxygen heterocycles. *J. Chem. Soc., Perkin Trans.* 12002, (21), 2301-2323.

[71] Blunt, J. W.; Carroll, A. R.; Copp, B. R.; Davis, R. A.; Keyzers, R. A.; Prinsep, M. R. Marine natural products. *Nat. Prod. Rep.* 2018, 35 (1), 8-53.

[72] Wolfe, J. P.; Rossi, M. A. Stereoselective Synthesis of Tetrahydrofurans via the Palladium-Catalyzed Reaction of Aryl Bromides with γ-Hydroxy Alkenes: Evidence for an Unusual Intramolecular Olefin Insertion into a Pd(Ar) (OR) Intermediate. *J. Am. Chem. Soc.* 2004, 126 (6), 1620-1621.

[73] Miller, Y.; Miao, L.; Hosseini, A. S.; Chemler, S. R. Copper-Catalyzed Intramolecular Alkene Carboetherification: Synthesis of Fused-Ring and Bridged-Ring Tetrahydrofurans. *J. Am. Chem. Soc.* 2012, 134 (29), 12149-12156.

[74] Gao, S.-S.; Garcia-Borràs, M.; Barber, J. S.; Hai, Y.; Duan, A.; Garg, N. K.; Houk, K. N.; Tang, Y. Enzyme-Catalyzed Intramolecular Enantioselective Hydroalkoxylation. *J. Am. Chem. Soc.* 2017, 139 (10), 3639-3642.

[75] Walsh, C. T.; Tang, Y. Recent Advances in Enzymatic Complexity Generation: Cyclization Reactions. *Biochemistry* 2018, 57 (22), 3087-3104.

[76] Miller, K. J.; Kitagawa, T. T.; Abu-Omar, M. M. Kinetics and Mechanisms of Methyl Vinyl Ketone Hydroalkoxylation Catalyzed by Palladium(II) Complexes. *Organometallics* 2001, 20 (21), 4403-4412.

[77] Boiteau, J.-G.; Van de Weghe, P.; Eustache, J. A New, Ring Closing Metathesis-Based Synthesis of (−)-Fumagillol. *Org. Lett.* 2001, 3 (17), 2737-2740.

[78] Utsunomiya, M.; Kawatsura, M.; Hartwig, J. F. Palladium-Catalyzed Equilibrium Addition of Acidic OH Groups across Dienes. *Angew. Chem.* 2003, 115 (47), 6045-6048.

[79] Barluenga, J.; Diéguez, A.; Rodriguez, F.; Fañanás, F. J.; Sordo, T.; Campomanes, P. [W(CO)$_5$]-Catalyzed endo- or exo-Cycloisomerization Reactions of 1,1-Disubstituted 4-Pentyn-1-ols: Experimental and Theoretical Studies. *Chem. Eur. J.* 2005, 11 (19), 5735-5741.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for preparing a catalyst, said method comprising:
   (a) providing a parent metal-organic framework (MOF), wherein the parent MOF comprises periodic repeats of a coordination complex comprising (i) an organic bridging ligand, wherein the organic bridging ligand is trimesic acid (BTC) or 2,2'-bipyridine-5,5'-dicarboxylate (dcbpy); and (ii) a metal-containing secondary building unit (SBU), wherein said metal-containing SBU comprises a metal oxo cluster comprising a metal ion M and one or more terminal or bridging OH or $OH_2$ ligands, wherein the metal ion M is selected from a zirconium (Zr) ion, an iron (Fe) ion, a chromium (Cr) ion, and an aluminum (Al) ion; and
   (b) reacting the parent MOF with a silyl triflate to replace one or more of the one or more terminal or bridging OH or $OH_2$ ligands with a triflate ligand.

2. The method of claim 1, wherein the SBU is selected from the group consisting of a Zr-oxo cluster and an Al-oxo cluster.

3. The method of claim 1, wherein the organic bridging ligand is trimesic acid (BTC).

4. The method of claim 1, wherein the parent MOF is provided by contacting a parent precursor MOF with a strong acid, wherein the parent precursor MOF comprises periodic repeats of a coordination complex comprising: (i) the organic bridging ligand and (ii) a metal-containing SBU comprising a metal oxo cluster comprising the metal ion M and a monocarboxylate ligand; and wherein contacting the parent precursor MOF with the strong acid replaces the monocarboxylate ligand with an OH or $OH_2$ ligand.

5. The method of claim 1, wherein the organic bridging ligand comprises a nitrogen-containing aryl or arylene group that can coordinatively bond to a metal ion, wherein said organic bridging ligand is dcbpy and the nitrogen-containing aryl or arylene group that can coordinatively bond to a metal ion is bipyridine.

6. The method of claim 5, wherein the parent MOF is provided by contacting a parent precursor MOF with ozone, wherein the parent precursor MOF comprises coordination complexes between a metal-containing SBU comprising a metal oxo cluster, and at least two different organic bridging ligands, wherein one of the organic bridging ligands is dcbpy and the other organic bridging ligand is 1,4-benzenediacrylic acid; and wherein contacting the parent precursor MOF with the ozone replaces a coordinative bond between a 1,4-benzenediacrylic acid ligand and metal ion M of the SBUs with a coordinative bond between the metal ion M of the SBU and a hydroxide ligand.

7. The method of claim 5, wherein the method further comprises contacting the MOF with a metal complex comprising a second metal ion $M_2$, thereby metalating the nitrogen-containing aryl or arylene group of the organic bridging ligand with the second metal ion $M_2$.

8. The method of claim 1, wherein the catalyst is provided as a catalytic composite material and wherein providing the parent MOF comprises providing a parent composite material by:
   (a1) contacting (i) BTC, (ii) a metal salt comprising the metal ion M, and (iii) silicon dioxide ($SiO_2$), alumina ($Al_2O_3$), or titania ($TiO_2$) particles in a mixture of N,N-dimethylformamide and a monocarboxylic acid to form a parent precursor composite material, wherein the parent precursor composite material comprises particles of a parent precursor MOF attached to a surface of the $SiO_2$, $Al_2O_3$, or $TiO_2$ particles, wherein said parent precursor MOF comprises periodic repeats of a coordination complex comprising BTC and metal-containing SBUs, wherein the metal-containing SBUs each comprise a metal oxo cluster comprising the metal ion M and further comprising a monocarboxylate ligand; and
   (a2) reacting the parent precursor composite material with a strong acid to replace the monocarboxylate ligand with a hydroxide ligand, thereby forming the parent composite material comprising the parent MOF; and
   wherein reacting the parent MOF with a silyl triflate comprises reacting the parent composite material with a silyl triflate, thereby replacing the hydroxide ligand with a triflate ligand.

9. The method of claim 1, wherein the catalyst is provided as a catalytic composite material and wherein providing the parent MOF comprises providing a parent composite material by:
   (a1) contacting dcbpy, 1,4-benzenediacrylic acid, and an aluminum salt in the presence silicon dioxide ($SiO_2$), alumina ($Al_2O_3$), or titania ($TiO_2$) particles to form a parent precursor composite material, wherein the parent precursor composite material comprises particles of a parent precursor MOF attached to a surface of the $SiO_2$, $Al_2O_3$, or $TiO_2$ particles, wherein said parent precursor MOF comprises coordination complexes between an Al-oxo cluster SBU and both the dcbpy and the 1,4-benzenediacrylic acid, and
   (a2) reacting the parent precursor composite material with ozone to replace coordinative bonds between the 1,4-benzenediacrylic acid and Al ions of the SBU with coordinative bonds between the Al ions and a hydroxide ligand, thereby forming a parent composite material comprising the parent MOF; and
   wherein reacting the parent MOF with a silyl triflate comprises reacting the parent composite material with (i) a silyl triflate, thereby replacing the hydroxide ligand with a triflate ligand; and (ii) a metal complex thereby metalating the bipyridine group of the dcbpy ligand.

10. A MOF catalyst prepared according to the method of claim 1.

* * * * *